(12) United States Patent
Phillips

(10) Patent No.: US 6,540,691 B1
(45) Date of Patent: *Apr. 1, 2003

(54) BREATH TEST FOR THE DETECTION OF VARIOUS DISEASES

(76) Inventor: Michael Phillips, 1 Horizon Rd., Suite 1415, Fort Lee, NJ (US) 07024

(*) Notice: Subject to any disclaimer, the term of this patent is extended or adjusted under 35 U.S.C. 154(b) by 0 days.

This patent is subject to a terminal disclaimer.

(21) Appl. No.: 09/869,938

(22) PCT Filed: Jan. 12, 2000

(86) PCT No.: PCT/US00/00707

§ 371 (c)(1), (2), (4) Date: Sep. 18, 2001

(87) PCT Pub. No.: WO00/41623

PCT Pub. Date: Jul. 20, 2000

Related U.S. Application Data

(63) Continuation-in-part of application No. 09/229,020, filed on Jan. 12, 1999, now Pat. No. 6,221,026, and a continuation of application No. 09/436,798, filed on Nov. 8, 1999, now Pat. No. 6,254,547.
(60) Provisional application No. 60/143,242, filed on Jul. 9, 1999.

(51) Int. Cl.[7] .................................................. A61B 5/00
(52) U.S. Cl. ........................... 600/532; 73/23.3; 422/84
(58) Field of Search ..................... 600/532; 73/23.3; 422/84

(56) References Cited

U.S. PATENT DOCUMENTS

| | | | |
|---|---|---|---|
| 5,386,832 A | 2/1995 | Wagner et al. | 128/665 |
| 5,465,728 A | 11/1995 | Phillips | 128/730 |
| 5,515,859 A | 5/1996 | Paz | 128/719 |
| 5,996,586 A | 12/1999 | Phillips | 128/898 |
| 6,254,547 B1 * | 3/2001 | Phillips | 600/532 |
| 6,221,026 B1 * | 4/2001 | Phillips | 600/532 |

OTHER PUBLICATIONS

Phillips M. and Greenberg J., "Detection of Endogenous Ethanol and Other Compounds in the Breath by Gas Chromatography With On–Column Concentration of Sample" Analytical Biochemistry, 1987; 163:165–169.

Phillips, M., "Method For the Collection and Assay of Volatile Organic Compounds in the Breath" Analytical Biochemistry, 1997; 247:272–278.

Phillips M., " Breath Tests in Medicine" Scientific American 1992; 267(1): 74–79.

Phillips, M., Sabas M. & Greenberg J., "Alveolar Gradient of Pentanein Normal Human Breath" Free Radical Res. Commun. 1994; 20:333–337.

* cited by examiner

Primary Examiner—Robert L. Nasser
(74) Attorney, Agent, or Firm—Pitney, Hardin, Kipp & Szuch, LLP

(57) ABSTRACT

The alkane profile (FIGS. 12–14) comprising the alveolar gradients of n-alkane in breath having 4 carbons to 20 carbons, and the methyl alkane profile (FIGS. 30–34) are determined for the diagnosis of disease in mammals, including humans.

4 Claims, 52 Drawing Sheets

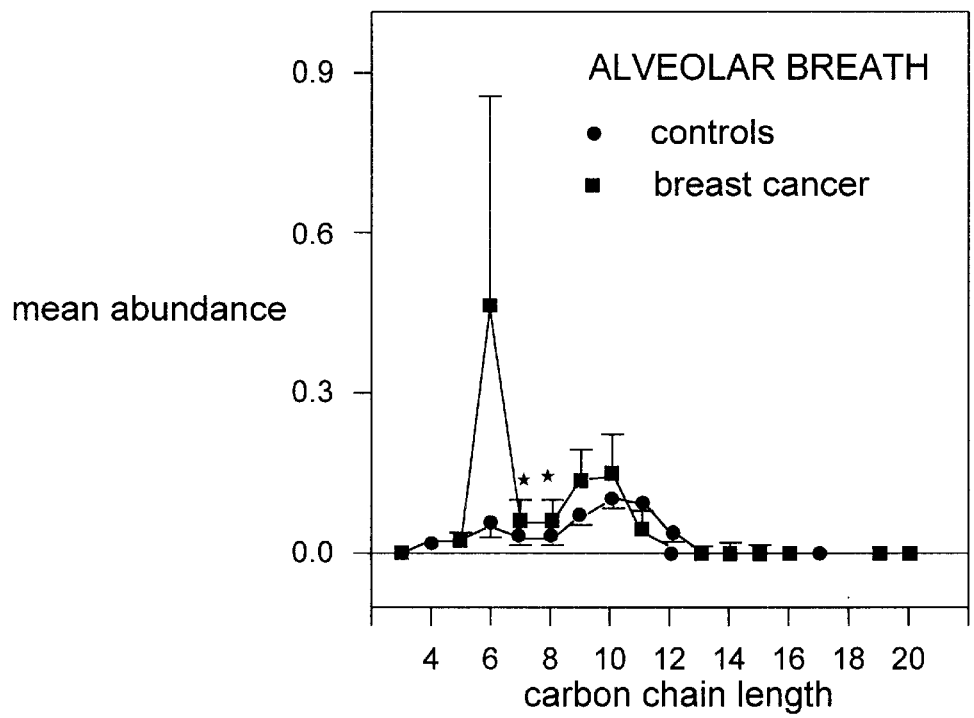
F I G. 12
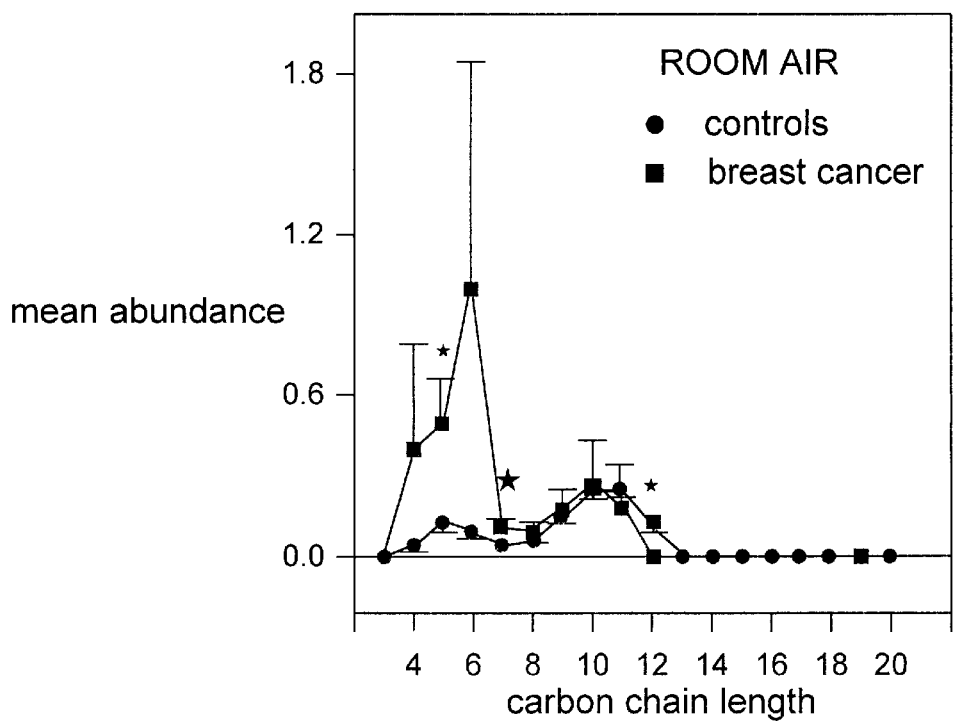
F I G. 13

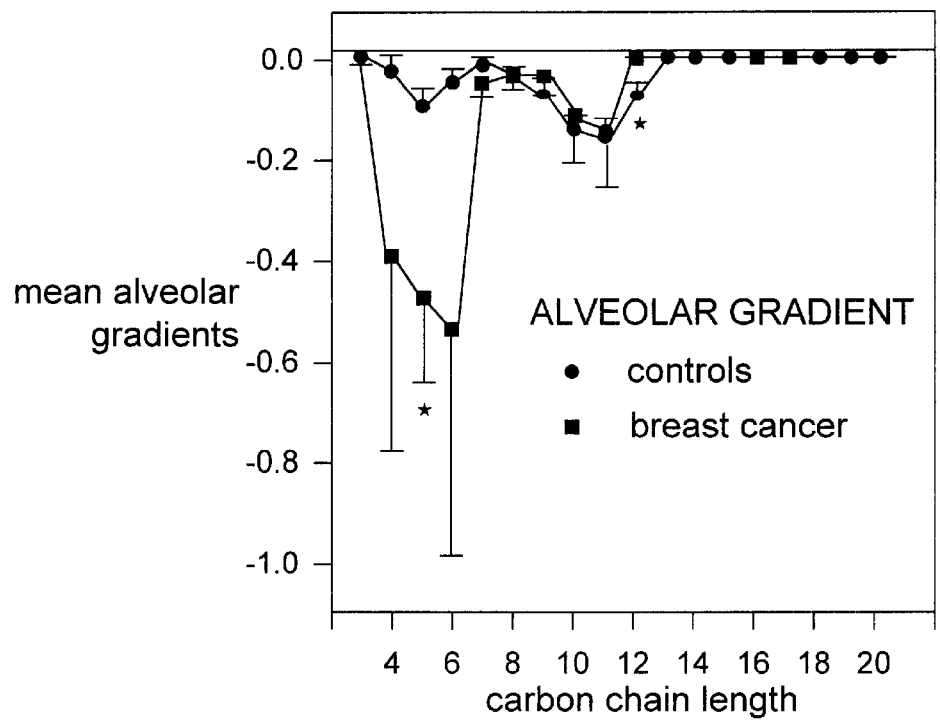
F I G. 14
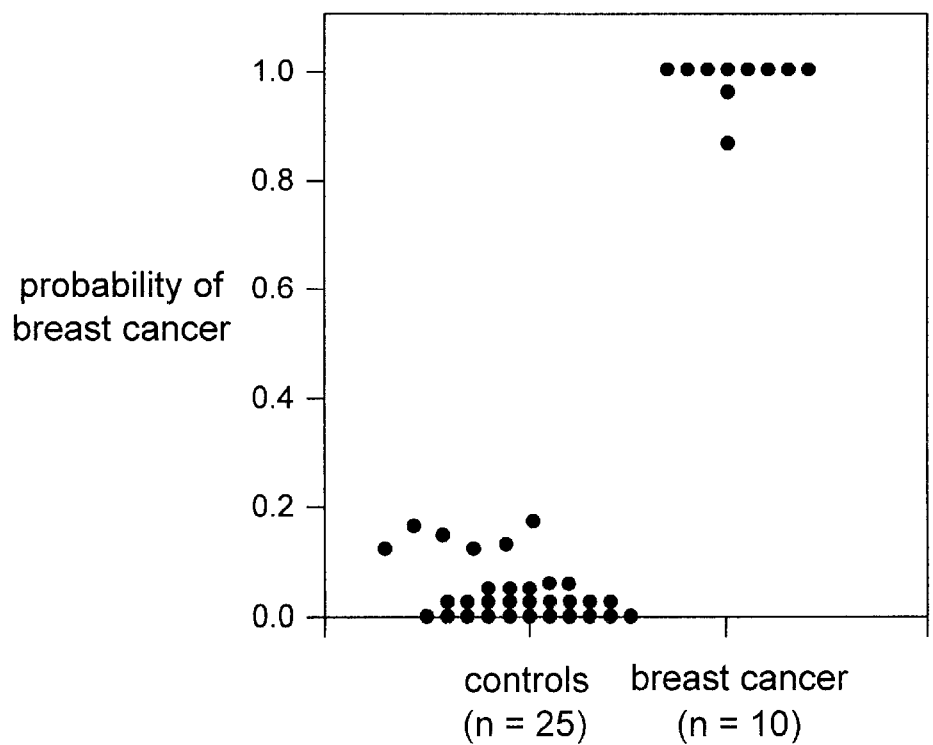
F I G. 15

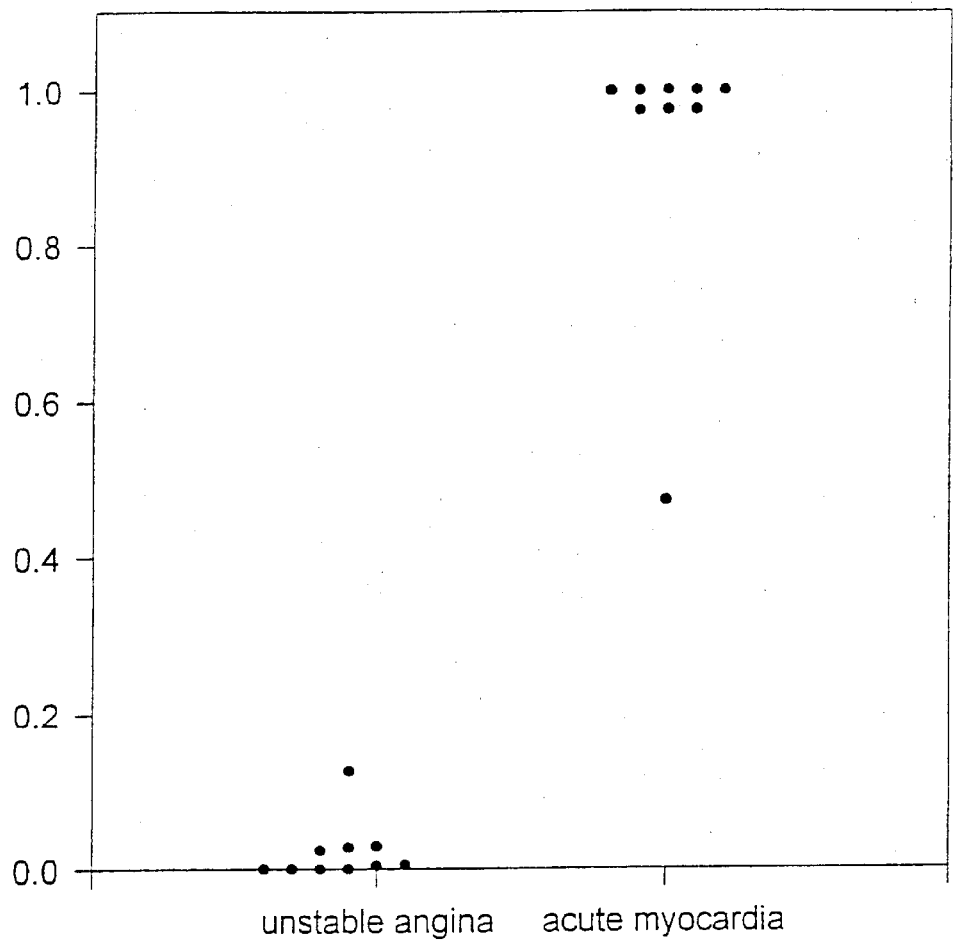
F I G. 20

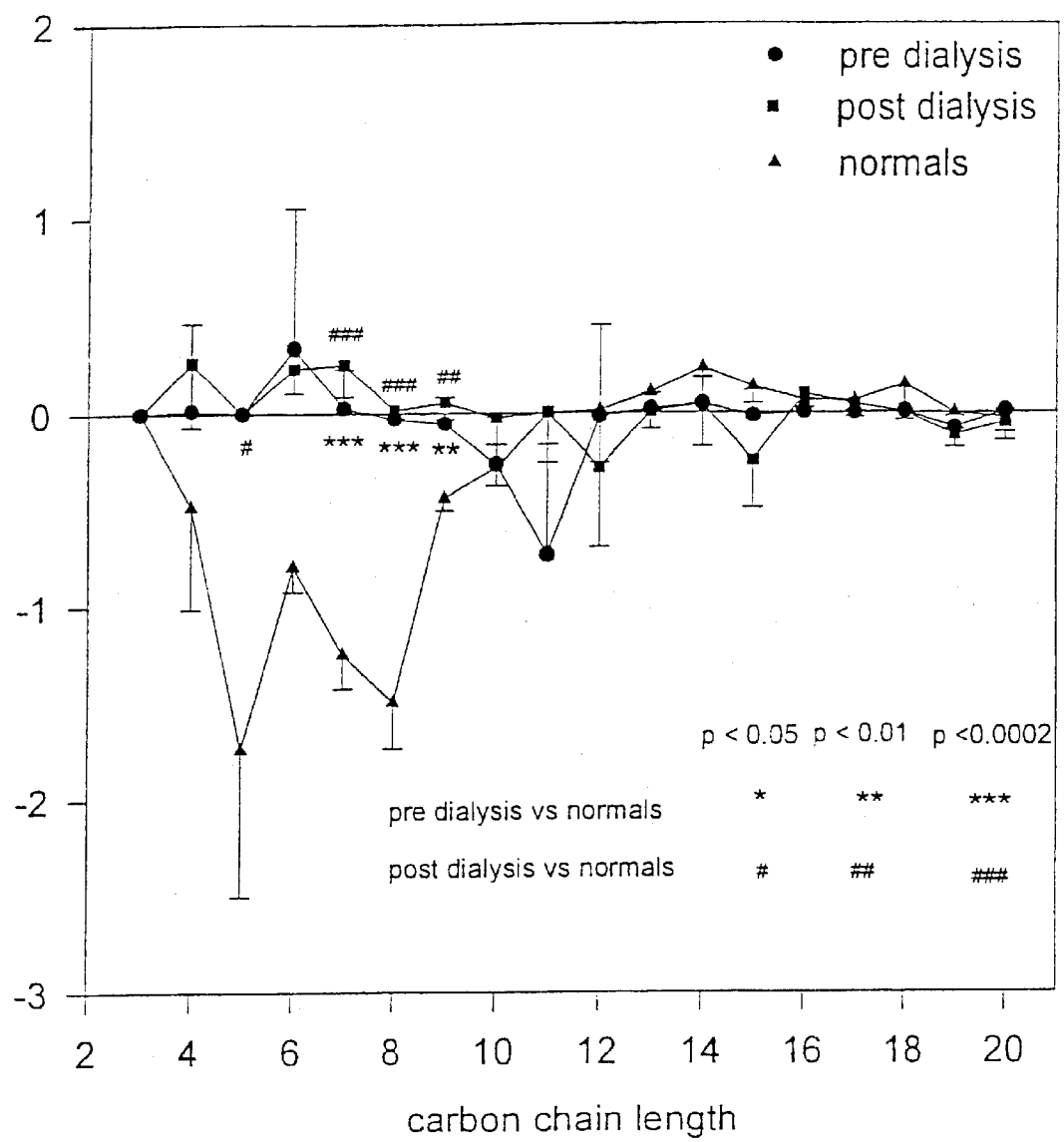
F I G. 25

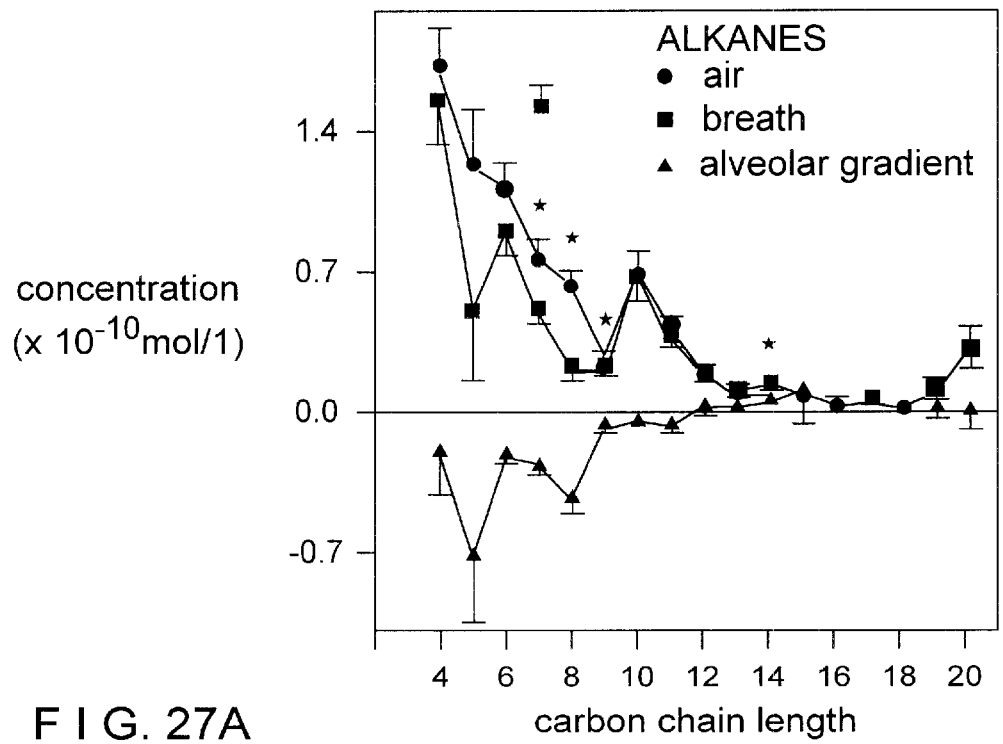
F I G. 27A
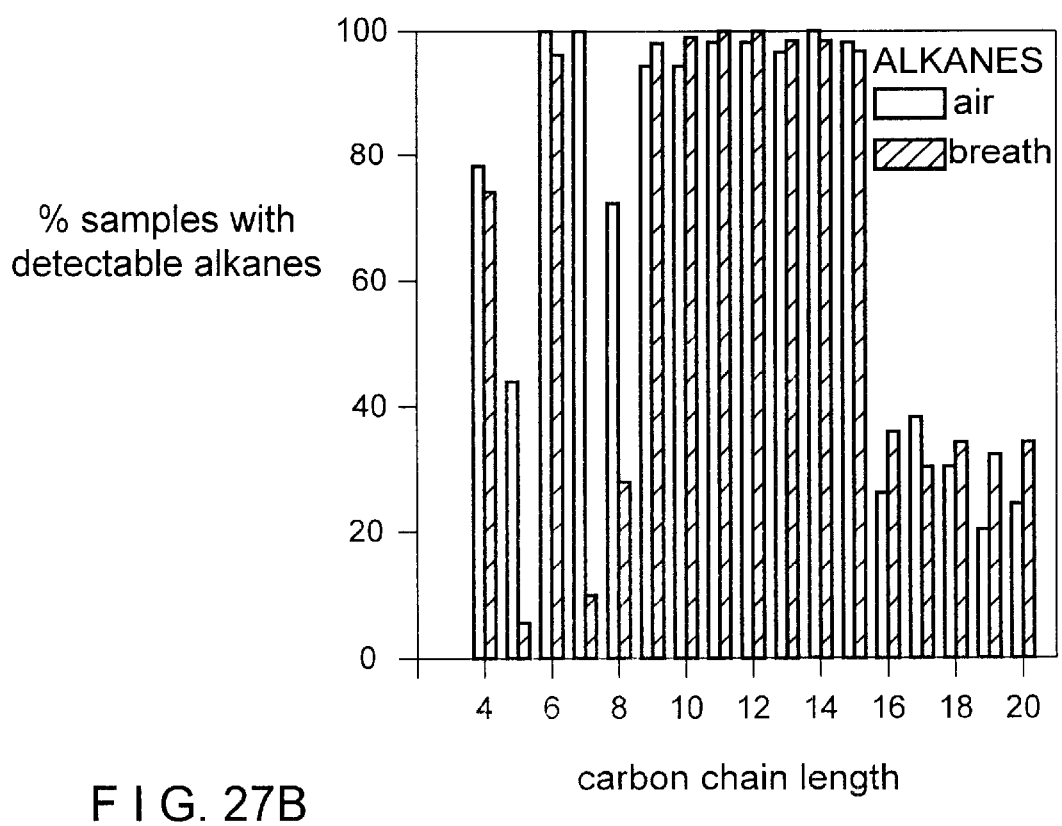
F I G. 27B

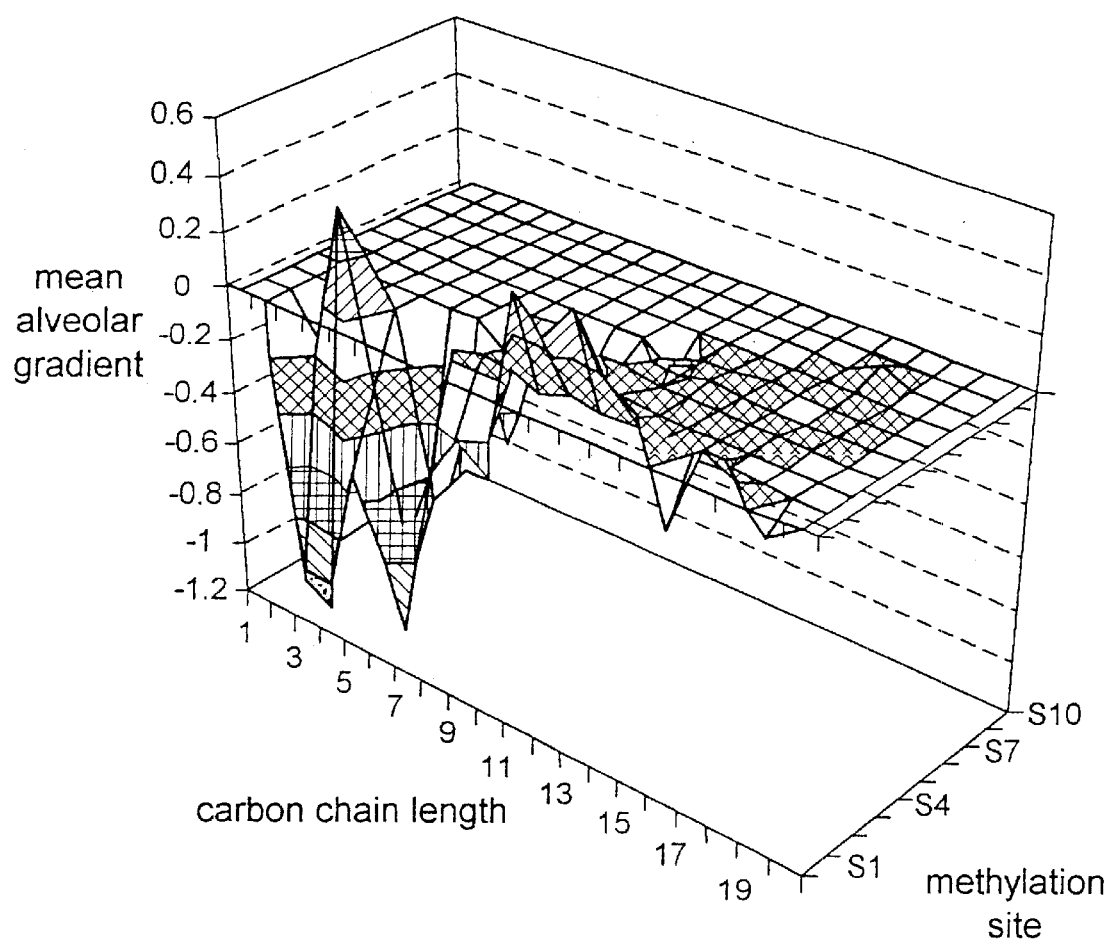
F I G. 30

Normal human : alkane / methylalkane contour ages 9 to 40

Normal human : alkane / methylalkane contour ages 40 to 89

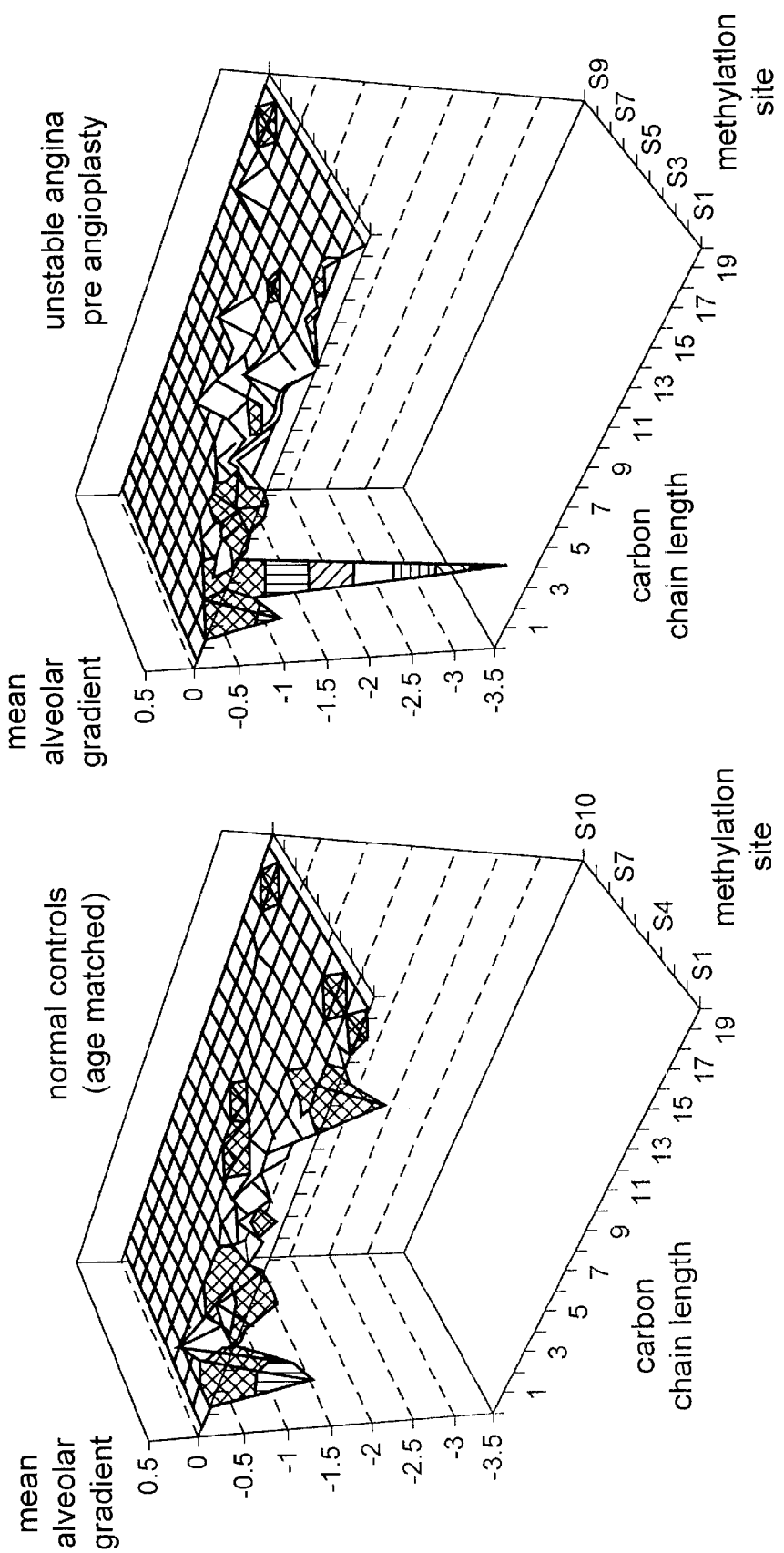

BREATH TEST FOR THE DETECTION OF VARIOUS DISEASES

CROSS-REFERENCE TO RELATED APPLICATION

This application is a national stage application of PCT/US00/00707 filed January 2002, which is a CIP of U.S. Ser. No. 09/229,020, filed Jan. 12, 1999, which issued as U.S. Pat. No. 6,221,026 on Apr. 24, 2001, and a continuation of U.S. Ser. No. 09/436,798, filed Nov. 8, 1999, which issued as U.S. Pat. No. 6,254,547 on Jul. 23, 2001, and a continuation of provisional application No. 60/143,242 filed Jul. 9, 1999. PCT/US00/00707 was published in English under publication number WO 00/41623 on Jul. 20, 2000.

BACKGROUND OF THE INVENTION

1. Field of the Invention

The invention relates to the diagnosis of disease in mammals and more particularly to a method employing breath testing for the detection of particular diseases in humans.

2. Brief Description of Related Art

Volatile Organic Compounds in Human Breath

Alveolar breath is a distinctive gas whose chemical composition differs markedly from inspired air. Volatile organic compounds (VOCs) are either subtracted from inspired air (by degradation and/or excretion in the body) or added to alveolar breath as products of metabolism. Some features of this transformation have been well understood for many years: e.g. oxygen is subtracted and carbon dioxide is added by the oxidative metabolism of glucose (Phillips M., Breath tests in medicine, Scientific American 1992:267(1):74–79).

Pauling et al, in 1971, employed cold trapping to concentrate the VOCs in breath and found that normal human breath contained several hundred different VOCs in low concentrations (Pauling L. Robinson A B, Teranishi R and Cary P: Quantitative analysis of urine vapor and breath by gas-liquid partition chromatography, Proc Nat Acad Sci USA 1971:68:2374–6). This observation has been subsequently confirmed in many different laboratories, employing progressively more sophisticated and sensitive assays. More than a thousand different VOCs have been observed in low concentrations in normal human breath (Phillips M: Method for the collection and assay of volatile organic compounds in breath, Analytical Biochemistry 1997;247:272–278).

Figure 1:
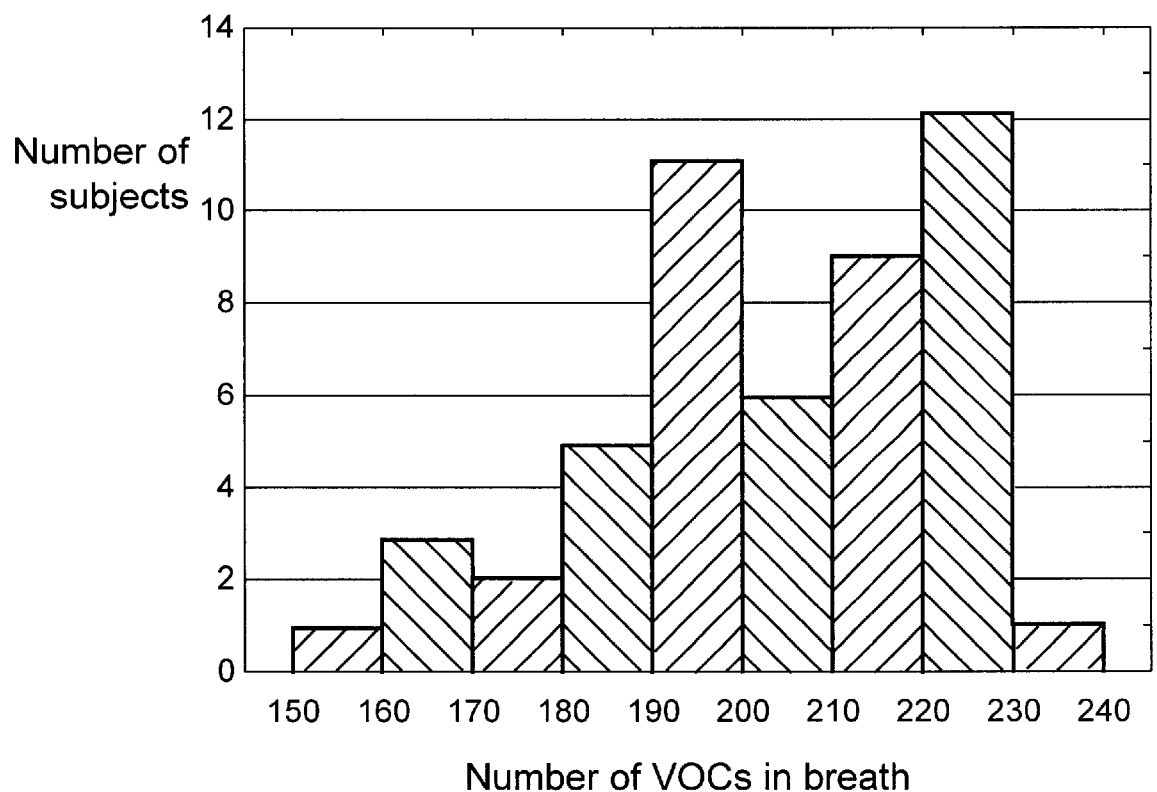

Reactive oxygen species (ROS) are toxic byproducts of energy production in the mitochondria. "Oxidative stress" is the constant barrage of oxidative damage which ROS inflict upon DNA, proteins, lipids and other biologically important molecules Fridovich I. The biology of oxygen radicals. Science 201:875–880;1978; Pryor W A: Measurement of oxidative stress status in humans. Cancer Epidemiol Biomarkers Prev 2 (3):289–292; 1993 (FIG. 1). Oxidative stress has been implicated as a pathologic mechanism in aging and several diseases. Ashok B T; Ali R: The aging paradox: free radical theory of aging Exp Gerontol 1999 34(3):293–303; Saretzki G and von Zglinicki T: (Replicative senescence as a model of aging: the role of oxidative stress and telomere shortening—an overview) Z Gerontol Geriatr 1999;32(2):69–75; Halliwell B, Gutteridge J M C, Cross C E: Free radicals, antioxidants, and human disease: Where are we now? J Lab Clin Med 119: 598–620;1992. Consequently, oxygen is now recognized as both beneficial and harmful: it is essential to sustain mammalian life because it is the final acceptor of electrons in oxidative metabolism, but in this process it also causes oxidative stress and tissue damage.

Breath Alkanes as Markers of Disease

Analysis of VOCs in inspired air and alveolar breath is a useful research tool with potential applications in clinical medicine. Breath analysis opens a non-invasive window on normal metabolic pathways, and also illustrates how these pathways are altered in disease.

Figure 5:
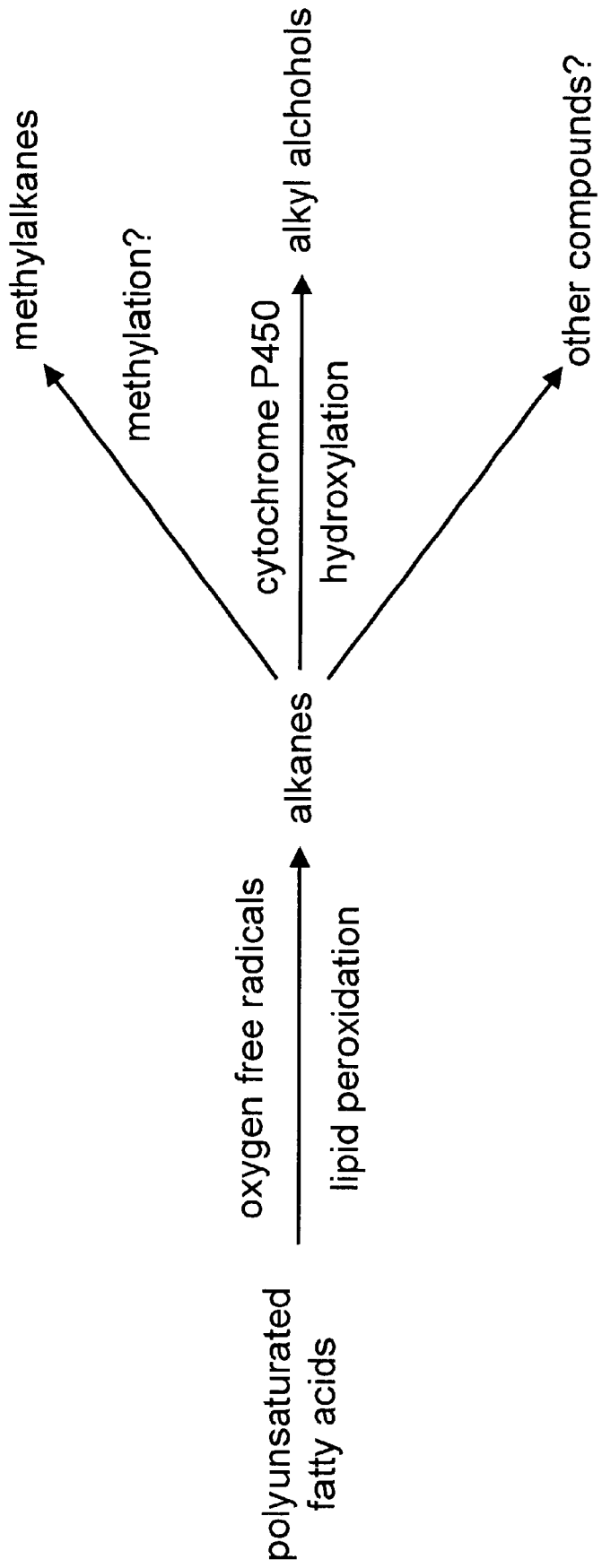

Alkanes in breath are markers of oxygen free radical (OFR) activity in vivo. OFR's degrade biological membranes by lipid peroxidation, converting polyunsaturated fatty acids (PUFAs) to alkanes which are excreted through the lungs as volatile organic compounds (VOCs); (Kneepkens C M F, Ferreira C. Lepage G and Roy C C: The hydrocarbon breath test in the study of lipid peroxidation; principles and practice, Clin Invest Med 1992; 15(2):163–186;

Kneepkens C M F, Lepage G and Roy C C: The potential of the hydrocarbon breath test as a measure of lipid peroxidation, Free Radic Biol Med 1994;17:127–60) (FIG. 5). Increased pentane in the breath has been reported as a marker of oxidative stress in several diseases including breast cancer (Hietanen E, Bartsch H, Beireziat J-C, Camus A-M, McClinton S. Eremin O, Davidson L and Boyle P: Diet and oxidative stress in breast, colon and prostate cancer patients: a case control study, European Journal of Clinical Nutrition 1994;48:575–586), heart transplant rejection (Sobotka P A, Gupta D K, Lansky D M, Costanzo M R and Zarling E J: Breath pentane is a marker of acute cardiac allograft rejection. J. Heart Lung Transplant 1994; 13:224–9), acute myocardial infarction (Weitz Z W, Birnbaum A J, Sobotka P A, Zarling E J and Skosey J L: High breath pentane concentrations during acute myocardial infarction. Lancet 1991;337:933–35), schizophrenia (Kovaleva E. S, Orlov O. N, Tsutsul'kovskaia Mia, Vladimirova T. V, Beliaev B. S: Lipid peroxidation processes in patients with schizophrenia. Zh Nevropatol Psikiatr 1989:89(5): 108–10), rheumatoid arthritis (Humad S. Zarling E. Clapper M and Skosey J L: Breath pentane excretion as a marker of disease activity in rheumatoid arthritis, Free Rad Res Comms 198;5(2):101–106) and bronchial asthma (Olopade C O, Zakkar M, Swedler W I and Rubinstein I: Exhaled pentane levels in acute asthma, Chest 1997;111(4):862–5). Analysis of breath alkanes could potentially provide a new and non-invasive method for early detection of some of these disorders (Phillips M: Breath tests in medicine, Scientific American 1992;267 (1):74–79).

Alkanes are degraded to other VOCs such as alkyl alcohols and possibly to methyl alkanes (Phillips M: Method for the collection and assay of volatile organic compounds in breath, Analytical Biochemistry 1997; 247:272–78) but there is little information about the excretion of these compounds in the breath, where they might also provide clinically useful markers of disease.

Breath testing for VOC markers of oxidative stress is a comparatively new field of research, and published information is scanty in a number of areas: First, studies of breath alkanes have focused near-exclusively on ethane and pentane which are degradation products of n-3 and n-6 PUFAs respectively. Hexane and octane have also been observed in the breath of animals, but there is little information about longer chain VOCs in normal human breath. Second, most studies have taken little or no account of the presence of alkanes in the inspired ambient air, where they appear to be near-universal contaminants. Cailleux and Allain questioned whether pentane was a normal constituent of human breath, because the concentrations in breath and inspired air, were frequently so similar. (Cailleux A & Allain P: Free Radicals Res Commun 1993; 18:323–327). This problem may be resolved by determination of the alveolar gradient of a VOC, the difference between its concentration in the breath and in the ambient air. (Phillips M. Sabas M & Greenberg J: Free Radical Res Commun. 1994; 20:333–337).

Breath Alkanes As Markers of Breast Cancer

Breast cancer is a common disease which now affects approximately one in every ten women in the United States. Early detection by periodic screening mammography can reduce mortality by 20–30%. However, mammography is expensive, frequently requires painful breast compression, entails exposure to radiation, and generates false-positive results in one third of all women screened over a 10 year period (Elmore J G, Barton M B, Moceri V M, Polk S, Arena P J and Fletcher S W: Ten-year risk of false positive screening mammograms and clinical breast examinations). There is a clinical need for a screening test for breast cancer which is at least as sensitive and specific as mammography, but is simpler, safer, less painful and less expensive.

The cytochrome P450 (CYP) system comprises a group of mixed function oxidase enzymes which metabolize drugs and other xenobiotics. This system also metabolizes alkanes to alcohols e.g. n-hexane to 2- and 3-hexanol (Crosbie S J, Blain P G and Williams F M: Metabolism of n-hexane by rat liver and extrahepatic tissues and the effect of cytochrome P40 inducers. Hum Exp Toxicol 1997; 16(3):131–137). Rats treated with a potent cytochrome P-450 inhibitor exhibited a ten-fold increase in hexane and other breath VOCs with no increase in hepatic lipid peroxidation, demonstrating the significance of this pathway for VOC clearance (Mathews J M, Raymer J H, Etheridge A S, Velez Gr and Bucher J R: Do endogenous volatile organic chemicals in breath reflect and maintain CYP2E1 levels in vivo? Toxicol Appl Pharmacol 1997; 146(2):255–60). Studies in normal animals initially have demonstrated that the liver is a major site of clearance of alkanes from the body by cytochrome P450 metabolism (Burk-R J; Ludden-T M; Lane-J M: Pentane clearance from inspired air by the rat: dependence on the liver. Gastroenterology. 1983 84(1): 138–42: Daugherty-M S; Ludden-T M; Burk-R F: Metabolism of ethane and pentane to carbon dioxide by the rat, Drug-Metab-Dispos. 1988; 16(5):666–71).

However, several recent reports have demonstrated that cytochrome P450 metabolism is not confined to the liver. Metabolism of alkanes to alcohols has also been observed in lung, brain and skeletal muscle microsomes expressing cytochrome P450 2E1 or 2B6 (Crosbie S J, Blain P G and Williams F M: Metabolism of n-hexane by rat liver and extrahepatic tissues and the effect of cytochrome P-450 inducers. Hum Exp Toxicol 1997; 16(3):131–137). The cytochrome P450 system is also present in human breast tissue. Murray et al reported that cytochrome P450 CYP1 B1 was expressed in cancers of breast as well as other tissues (Murray G I, Taylor M C, McFadyen M C, McKay J A, Greenlee W F, Burke M D and Melvin W T: Tumor-specific expression of cytochrome P450 CYP1B1. Cancer Res 1997;57(14):3026–31). Huang et al detected activity of the xenobiotic-metabolizing CYP1, CYP2 and CYP3 subfamilies of cytochrome P450 in human breast tissue (Huang Z, Fasco M J, Figge H L, Keyomarsi K and Kaminsky L S: Expression of cytochromes P450 in human breast tissue and tumors. Drug Metab Dispos 1996;24(8):599–905). They observed: " . . . When normal and tumor tissues were from the same individuals, higher amplification occurred in normal tissues . . . The machinery of possible in situ bioactivation of xenobiotics and modification of therapeutic drugs is thus present in human breast tissue". Taken together, these studies demonstrate:

1. Alkanes are metabolized in vivo by cytochrome P450 enzymes
2. Cytochrome P450 enzymes are present in normal and neoplastic human breast tissues
3. Breast cancer induces increased cytochrome P450 activity in normal breast tissue
4. Breast cancer may therefore induce increased metabolism of alkanes.

Hietanen et al studied 20 women with histologically proven breast cancer and a group of age and sex-matched controls (Hietanen E, Bartsch H, Beireziat J-C, Camus A-M, McClinton S. Eremin O, Davidson L and Boyle P: Diet and oxidative stress in breast, colon and prostate cancer patients: a case control study, European Journal of Clinical Nutrition 1994;48:575–586). Mean breath pentane concentration in the cancer patients (2.6 ppb, SD=2.8) was significantly higher than in the controls (0.6 ppb, SD=1.1, p<0.01). They did not report concentrations of pentane in ambient air, nor the alveolar gradients of pentane.

Breath Alkanes as Markers of Ischemic Heart Disease

More than 3 million patients are hospitalized every year in the United States for chest pain. The cost is over $3 billion just for those found to be free of acute disease. Many patients with acute chest pain but without myocardial infarction are admitted to specialized services to determine the cause of their pain (Hoekstra J W and Gibler W B; Chest pain evaluation units: an idea whose time has come, JAMA 1997;278(20):1701–2). The main objective is to detect unstable angina, which is potentially life threatening. Evaluation of these patients is frequently extensive and expensive, entailing a comprehensive battery of tests such as echocardiography, exercise electrocardiography (ECG), myocardial scintigraphy and Holter monitoring. Employing such a battery of tests, Fruergaard et al evaluated 204 patients with acute chest pain but without myocardial infarction. They found the commonest etiology was gastro-esophageal disease, followed by ischemic heart disease and chest wall syndrome. The high risk subset comprised less than a third of all diagnoses (Fruergaard P, Laundbjerg J, Hesse B et al: The diagnoses of patients admitted with acute chest pain but without acute myocardial infarction. Eur Heart J 1996; 17(7):1028–34). McCullough et al determined that the practice of hospital admission for patients with chest pain and essentially normal ECGs was not cost favorable, at $1.7 million dollars per life saved (McCullough P A, Ayad O, O'Neill W W and Goldstein J A: Costs and outcomes of patients admitted with chest pain and essentially normal electrocardiograms. Clin Cardiol 1988;21(1):22–6). Despite these and other well-documented studies, patients with acute chest pain but without myocardial infarction are commonly hospitalized because physicians are generally reluctant to discharge a patient if there is a risk of unstable angina and sudden death. Hence there is a clinical need and an economic need for a diagnostic test which differentiates between the high-risk patient with cardiac chest pain who could benefit from hospitalization, and the low-risk patient with non-cardiac chest pain who could be safely discharged home and evaluated as an out-patient. Such a test could potentially reduce mortality and morbidity from unrecognized heart disease, while at the same time reducing costs to the health care system by reducing the number of unnecessary hospitalizations. There is now new evidence that a non-invasive breath test could provide such a test.

There is an increasing body of evidence that myocardial oxygen free radical activity is increased in ischemic heart disease. Oxidative stress also increases during surgical reperfusion of the heart, or after thrombolysis, and it is related to transient left ventricular dysfunction, or stunning (Ferrari R; Agnoletti L; Comini L; Gaia G; Bachetti T; Cargnoni A; Ceconi C; Curello S; Visioli O; Oxidative stress during myocardial ischaemia and heart failure, Eur Heart J 1998;19 Suppl B:B2–11). The two major hypotheses which explain the mechanism of stunning are that it either results from a burst of oxygen free radical activity or from a loss of sensitivity of contractile filaments to calcium. These hypotheses are not mutually exclusive, and are likely to represent different facets of the same pathophysiological cascade. Myocardial stunning occurs clinically in various situations in which the heart is exposed to transient ischemia, such as unstable angina, acute myocardial infarction with early reperfusion, exercised-induced ischemia, cardiac surgery and cardiac transplantation (Bolli R: Basic and clinical aspects of myocardial stunning, Prog Cardiovasc Dis 1998;40(6): 477–516: Miura H; Morgan D A; Gutterman D D; Oxygen-derived free radicals contribute to neural stunning in the canine heart, Am J Physiol 1997;273(3 Pt 2): H1569–75).

In 1991, Weitz et al reported that breath pentane was significantly increased in 10 patients with acute myocardial infarction compared to 10 healthy controls (Weitz Z W, Birnbaum A J, Sobotka P A, Zarling E J and Skosey J L: High breath pentane concentrations during acute myocardial infarction. Lancet 1991;337:933–35). However, these results were called into question by a subsequent study from the same institution which found no significant differences in breath pentane between 15 patients with acute myocardial infarction, 15 with stable angina and 15 normal controls (Mendis S. Sobotka P A and Euler D E: Expired hydrocarbons in patients with acute myocardial infarction, Free Radic Res 1995;23(2):117–22). They did observe a significant increase in breath pentane following balloon deflation in five patients with unstable angina undergoing coronary angioplasty (Mendis S, Sobotka P A, Leja F L and Euler D E: Breath pentane and plasma lipid peroxides in ischemic heart disease, Free Radic Biol Med 1995;19(5):679–84).

However, Kohlmuller and Kochen demonstrated a fundamental flaw in the breath pentane assays: the column employed in the gas chromatograph (GC) did not separate pentane from isoprene, the most abundant compound in breath. What the investigators had reported as breath pentane was probably a mixture of pentane and isoprene (Kohlmuller D; Kochen W: Is n-pentane really an index of lipid peroxidation in humans and animals? A methodological reevaluation. Anal Biochem 1993 May 1;210(2) :268–76). The GC columns employed in this research separate pentane and isoprene from one another (Phillips M, Sabas M and Greenberg J. Alveolar gradient of pentane in normal human breath. Free Radical Research Communications 1994;20(5):333–337).

Breath Alkanes as Markers of Heart Transplant Rejection

In December 1967, Christiaan Barnard, a South African surgeon, performed the first human heart transplant. Three days later, a surgical team in Brooklyn performed the first heart transplant in the United States. Since then, more than 36,000 heart transplants have been performed at over 271 centers throughout the world, including approximately 165 centers in the United States. There are nearly 20,000 people alive today in the United States who are the recipients of transplanted hearts. Refinements in patient selection, improved surgical techniques, newer antimicrobial agents, better myocardial protection, and the application of right ventricular endomyocardial biopsy to identify allograft rejection have resulted in better overall survival rates. Nevertheless, the most significant change in the management of transplant recipients came with the introduction and widespread commercial availability of cyclosporine in the early 1980s. Today, overall one year survival exceeds 80% and reported five and ten year survival approaches 65–70%.

With the introduction of cyclosporine in the early 1980s, the incidence of life threatening acute allograft rejection decreased considerably. Unfortunately, patients receiving cyclosporine based triple drug immunosuppression regimens seldom have physical complaints suggestive of allograft rejection until very late in the rejection process. Even prior to the introduction of cyclosporine, however, signs and symptoms of allograft rejection were quite non-specific; generally ranging from subtle electrocardiographic changes to malaise, fatigue, dyspnea, edema, and anorexia (Winters G L, Loh E, Schoen F J: Natural history of focal moderate cardiac allograft rejection, Circulation 1995;91:1975. Billingham M E, Cary N R B, Hammond E H et al: A working formulation for the standardization of nomenclature in the diagnosis of heart and lung rejection study group. Heart Transplant 1990;9:587). Non-invasive techniques to diagnose rejection, such as electrocardiographic changes or echocardiographic indices suggestive of diastolic dysfunction, are relatively insensitive and have not routinely been used in clinical practice. Likewise, thallium and magnetic resonance imaging have not proven useful. Hence, right ventricular endomyocardial biopsy has remained the standard against which all other techniques are compared. The primary purposes of the right ventricular endomyocardial biopsy in the heart transplant recipient are to identify allograft rejection, assess the efficacy of treatment, and to rule out infectious etiologies. Biopsies are performed weekly for the first six post-operative weeks, biweekly until the third post-operative month, and monthly until month six. Subsequent intervals are generally determined on an individual basis. Unfortunately, right ventricular endomyocardial biopsy is associated, albeit infrequently, with complications including hematoma, infection, arrhythmia, ventricular perforation, and the development of coronary artery to right ventricle fistulas. There is a clinical need for an alternative method of detecting heart transplant rejection with a safe and non-invasive diagnostic test.

There is a well-documented biochemical basis for breath testing provides for the early detection of transplant rejection. Tissue damage arising from inflammation is accompanied by an accumulation of intracellular oxygen free radicals (OFR'S) which cause lipid peroxidation of lipid membranes (Kneepkens C M F, Ferreira C, Lepage G and Roy C C: The hydrocarbon breath test in the study of lipid peroxidation: principles and practice. Clin Invest Med 1992; 15(2):163–186. Kneepkens C M F, Lepage G, Roy C C. The potential of the hydrocarbon breath test as a measure of lipid peroxidation. Free Radic Biol Med 1994;17:127–60). This process is accompanied by the evolution of alkanes which are excreted in the breath. One of these alkanes, pentane, is the best documented marker of OFR activity. Sobotka et al studied 37 outpatients with stable cardiac allograft function.(Sobotka P A, Gupta D K, Lansky D M, Costanzo M R and Zarling E J: Breath pentane is a marker of acute cardiac allograft rejection. J Heart Lung Transplant 1994; 13:224–9). Breath pentane was measured by gas chromatography and the results were compared with routine surveillance endomyocardial biopsy. Histopathologic findings consistent with rejection were present on endomyocardial biopsy in 52% of the subjects. Average pentane excretion for subjects with mild rejection (4.2 nmol/l, SD=2.8) or moderate rejection (5.4 nmol/l, SD=2.6) exceeded that seen in subjects who did not have rejection (1.7 nmol/l, SD=0.9) (p<0.02). A pentane cutoff value of 2.43 nmol/l, chosen to give the highest negative predictive value, had a sensitivity of 0.80. The authors concluded that breath pentane excretion was a sensitive noninvasive screening test for the detection of cardiac allograft rejection. These encouraging results have attracted criticism: Holt et al noted that the details of their analytic technique were sketchy; they may not have really been observing isoprene because most chromatographic columns do not separate pentane from isoprene, the most abundant compound in human breath. (Holt D W, Johnston A and Ramsey J D: Breath pentane and heart rejection. J Heart Lung Transplant 1994; 13:1147–8. Kohlmuller D, Kochen W: Is n-pentane really an index of lipid peroxidation in humans and animals? A methodological reevaluation. Anal Biochem 1993;210:266–76).

Breath Alkanes as Markers of End-stage Renal Disease

End-stage renal disease (ESRD) is a fatal condition unless it is treated with either kidney transplantation or dialysis of blood or peritoneal fluid. However, dialysis is not a cure for ESRD. The yearly gross mortality rate of patients in the ESRD program in the United States has increased from 20% in 1982 to approximately 24% in 1991, which has persisted (1). This high mortality may be due in part to case-mix factors e.g. the acceptance of older patients with severe concomitant disease to the ESRD program. Despite this, there is no clear understanding of why the mortality is so high, and what potentially reversible factors may be contributing.

Clinicians who come into contact with patients with chronic renal failure are familiar with the classic odor of uremic breath. It has been variously described as "fishy", "ammoniacal" and "fetid" (2). Schreiner and Maher in their review of uremia described it as ammoniacal, comparing it to the smell of stale urine (3). Since the introduction of early dialysis in chronic renal failure, the debilitated patient with a foul mouth due to ulceration and bacterial overgrowth is seldom seen. However, a consistent fishlike odor is still noticeable in ESRD patients, suggesting that it is systemic in origin, rather than from bacteria in the mouth. As early as 1925, the uremic breath odor was described as arising from trimethylamine, in Osler's textbook (4). In 1963, Simenhoff et al reported increased levels of dimethylamine in the blood, cerebrospinal fluid and brain of patients with severe uremia (5). He extended this research with analysis of breath of uremic patients, employing GC (2). He found increased concentrations of secondary and tertiary amines, dimethylamine and trimethylamine. Both were significantly reduced by hemodialysis as well as by treatment with nonabsorbable antibiotics. He concluded that these VOCs were responsible in part for the classic fishy odor in uremic breath, and arose from bacterial overgrowth in the intestine.

The use of no-load breath tests for the study of altered breath VOCs in renal failure has attracted little subsequent attention during the past 20 years, though a number of studies employing pre-load breath tests have been reported. Scherrer et al used the breath aminopyrine test to demonstrate accelerated hepatic microsomal metabolism in patients with chronic renal failure resulting from analgesic abuse (6). Heinrich et al performed a similar study with radiolabelled aminophenazone in patients with ESRD, and observed a depression of cytochrome P450 mixed function oxidases which was significantly reversed by dialysis (7). Maher et al investigated the potential role of free radical-mediated pulmonary injury during hemodialysis. They studied breath hydrogen peroxide levels during the first two hours of hemodialysis, but found no significant changes (8). Epstein et al studied excretion of radiolabelled $CO_2$ in breath to demonstrate altered decarboxylation of alpha-ketoisovaleric acid in patients with chronic renal failure (9). In an animal model of trichlorethylene-induced nephrotoxicity, Cojocel et al found increased ethane in breath, demonstrating the role of oxygen free radical-induced lipid peroxidation (10). In addition, breath tests employing radiolabelled urea have been employed to demonstrate an increased rate of infection with H. pylori in ESRD patients.

The Breath Methylated Alkane Contour

Phillips et al also previously observed that methylated alkanes are common components of the breath in normal humans as well as in those suffering from lung cancer. Phillips M, Herrera J, Krishnan S, Zain M, Greenberg J and Cataneo R N: Variation in volatile organic compounds in the breath of normal humans. Journal of Chromatography B 629 (1–2):75–88; 1999; Phillips M, Gleeson K, Hughes J M B, Greenberg J, Cataneo R N, Baker L and McVay W P: Volatile organic compounds in breath as markers of lung cancer: a cross-sectional study. Lancet 353:1930–33; 1999. These VOCs appeared to provide additional markers of oxidative stress.

SUMMARY OF THE INVENTION

Improved analytical technology was employed to determine the most abundant volatile organic compounds (VOCs) in the breath of 50 normal humans.

Kinetic analysis was employed to demonstrate that the alveolar gradient of a VOC (abundance in breath minus abundance in room air) varies with the difference between the rate at which a VOC is synthesized in the body and the rate at which it is cleared from the body by metabolism and excretion.

A new marker of oxygen free radical (OFR) activity in the body was developed: the breath alkane profile. This comprised the alveolar gradients of a wide spectrum of VOCs ranging from C2 to C20 alkanes plotted as a function of carbon chain length. Similar profiles were developed for two alkane metabolites in breath: alkyl alcohols and 2-methyl alkanes. These profiles provide a new and non-invasive probe of human metabolism by demonstrating the relative predominance of synthesis versus clearance of a VOC in vivo.

These breath profiles were evaluated in clinical studies of breast cancer, cardiac chest pain, renal disease, and aging. The breath profiles of controls and patients with disease were compared by logistic regression analysis.

The breath alkane profile was determined in 35 women undergoing screening mammography. 10 had biopsy-proven breast cancer. The breath alkane profiles identified the women with breast cancer with 100% sensitivity and specificity.

The breath alkane profile was determined in 8 patients with unstable angina pectoris and in 50 normal controls with no known history of heart disease. The breath alkane profiles identified the patients with unstable angina pectoris with 100% sensitivity and specificity. The changes in the breath alkane profile were exaggerated during subsequent coronary angioplasty.

The breath alkane profile was determined in 19 patients with acute onset chest pain in a hospital emergency department. Ten had unstable angina pectoris and nine had an acute myocardial infarction. Compared to 50 normal controls with no known history of heart disease, the breath alkane profiles identified the patients with cardiac chest pain, and distinguished unstable angina pectoris from acute myocardial infarction with 100% sensitivity and specificity.

The breath alkane profile and breath alkyl alcohol profile were determined in 213 studies of heart transplant recipients. Two pathologists reviewed the endomyocardial biopsies independently, and agreed that no treatment was required in 182, but treatment was required in 13. The combination of the breath alkane profile and the breath alkyl alcohol profile identified heart transplant rejection requiring treatment with 84.6% sensitivity and 80.2% specificity.

The advanced new breath test appears to provide a highly, sensitive and specific test for breast cancer and cardiac chest pain. The profiles were different from one another in all conditions. The breath alkane profile was displaced downward in the patients with breast cancer, and upward in the patients with ischemic heart disease. Both the breath alkane profile and the alkyl alcohol profile were displaced upward in heart transplant rejection. These results of the breath tests are consistent with the documented pathophysiology of OFR'S in these disorders.

In a further aspect of the present invention, a new marker of oxygen free radical (OFR) activity in the body was developed: the breath alkane profile. This comprised the alveolar gradients of a wide spectrum of VOCs ranging from C2 to C20 alkanes plotted as a function of carbon chain length. Similar profiles were developed for two alkane metabolites in breath: alkyl alcohols and 2-methyl alkanes. These profiles provide a new and non-invasive probe of human metabolism by demonstrating the relative predominance of synthesis versus clearance of a VOC in vivo. In the present inventive method, methylated alkanes were combined with the breath alkane profile in order to construct the breath methylated alkane contour (BMAC), a new three-dimensional marker of oxidative stress. This technique has been refined herein by determining the alveolar gradient of methylated alkanes and incorporating this data into a three dimensional plot. That is, where alveolar gradient versus the carbon chain length of n-alkanes was previously plotted, a third dimension has been added to the plot, which is the location of methylation along the carbon chain of the n-alkane.

The information obtained from identifying the methylation site, in addition to the alveolar gradient and the carbon chain length of the nalkane, has produced a new and uniquely sensitive marker of oxidative stress in humans. In the data presented herein, collected in tests upon normal human beings and in those suffering form heart transplant rejection, it is shown that
1. Oxidative stress was greater in heart transplant recipients than in age-matched normal controls;
2. Oxidative stress increased with the severity of heart transplant rejection; and
3. The breath test was sensitive and specific for clinically significant rejection.

BRIEF DESCRIPTION OF THE DRAWINGS AND TABLES

FIG. 1: (Prior Art) Inter-individual variation in number of VOCs in breath. Frequency distribution of number of VOCs observed in breath samples.

Figure 2:
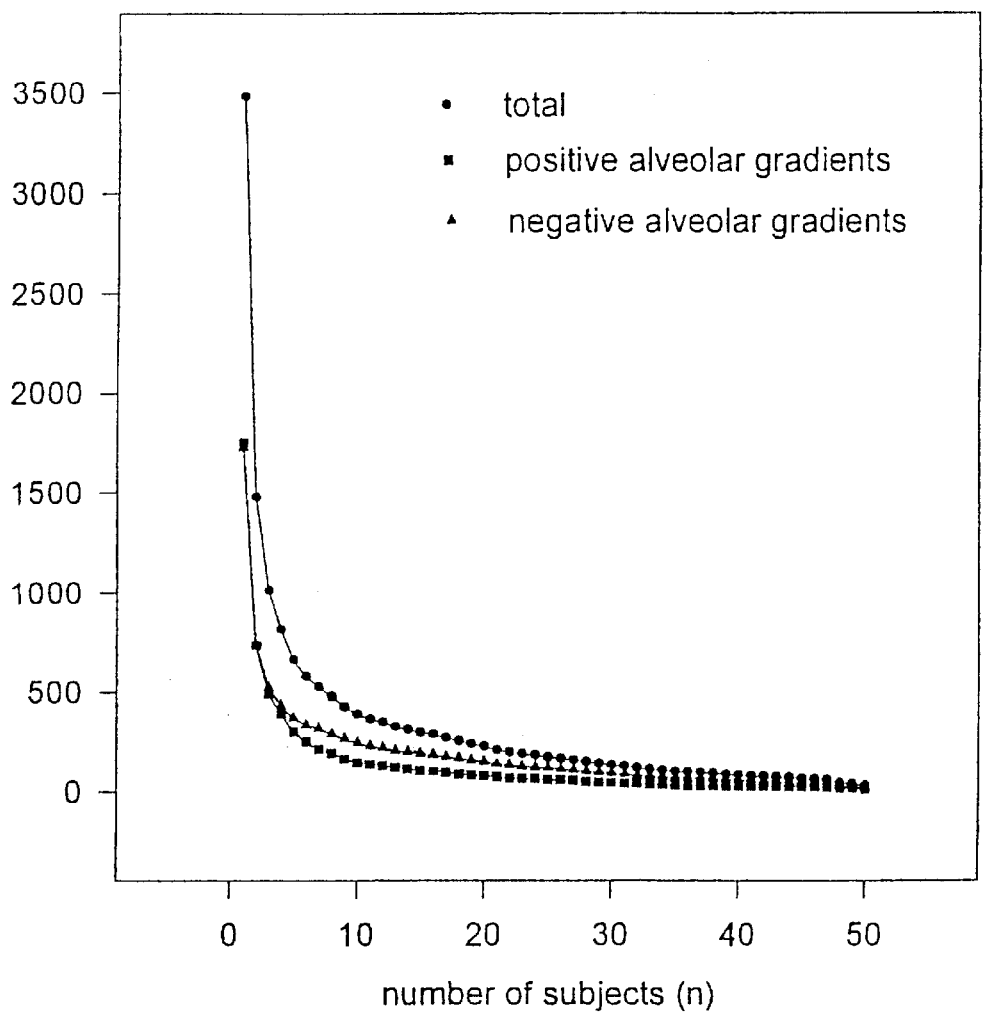

FIG. 2: (Prior Art) Variation in number of shared VOCs with sample size; 3481 different VOCs observed at least once, comprising 1753 VOCs with positive alveolar gradients and 1728 VOCs with negative alveolar gradients. Only 9 VOCs with positive alveolar gradients and 18 VOCs with negative alveolar gradients were observed in all 50 normal human subjects.

Figure 3:
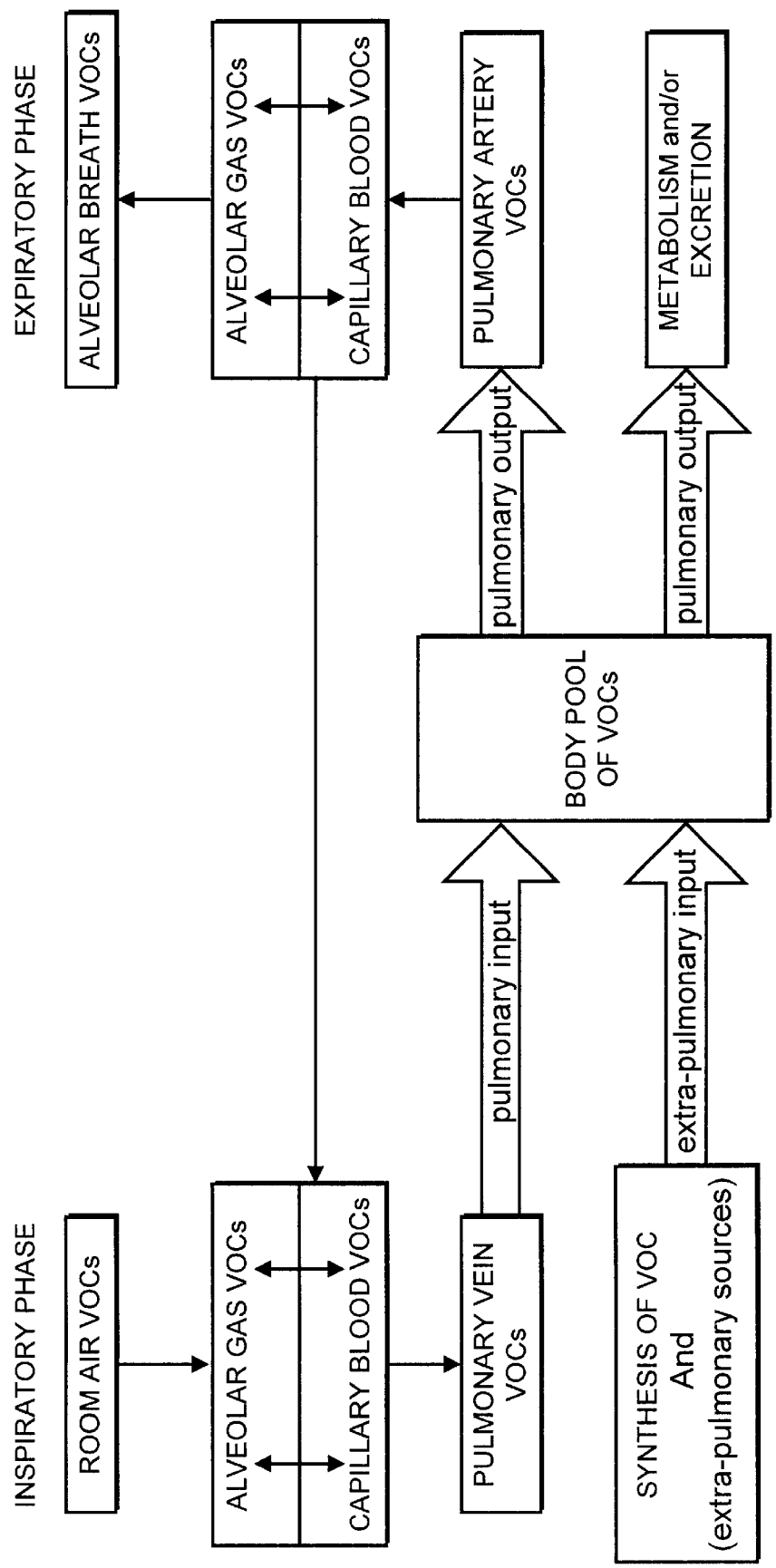

FIG. 3: (Prior Art) Pathways of VOCs through body compartments. Gaseous and capillary VOCs equilibrate rapidly in the pulmonary alveoli, and the dominant process varies with the phase of respiration. During the inspiratory phase, room air VOCs equilibrate with pulmonary venous blood, while during the expiratory phase, pulmonary arterial blood equilibrates with VOCs in alveolar breath. Extrapulmonary input of VOCs is primarily from endogenous synthesis, and extrapulmonary output of VOCs is predominantly by metabolism in the liver and excretion in the kidneys.

Figure 4:
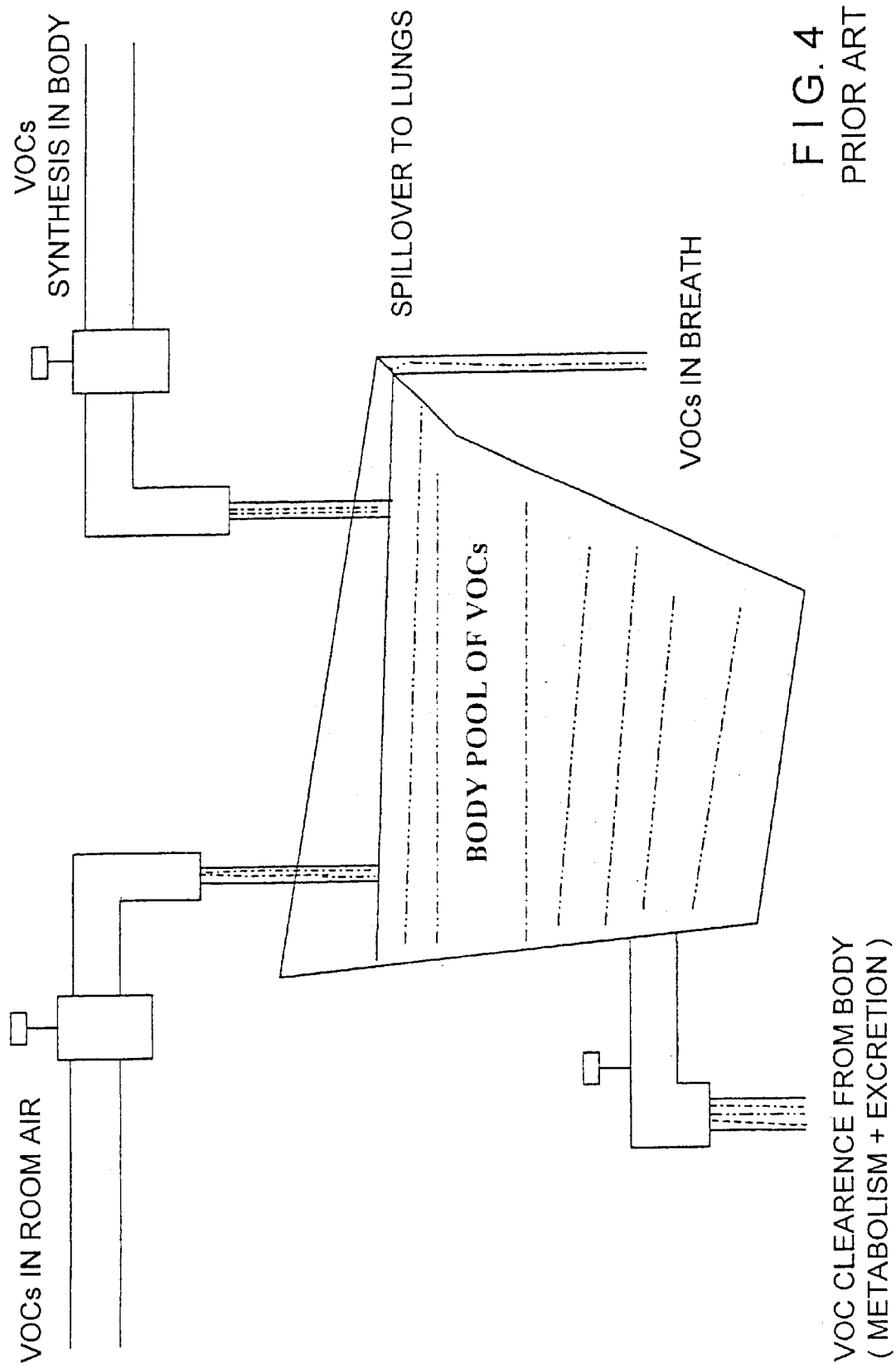

FIG. 4: (Prior Art) Water flow analogy of VOC kinetics: A VOC enters the body pool either from the inspired air or from synthesis in the body (ignoring minor inputs such as VOCs in foodstuffs). The VOC leaves the body pool either by clearance (metabolism and/or excretion) or else in the breath. If the VOC is neither synthesized nor cleared from the body, then the amount leaving in the breath must equal the amount entering from inspired air, and the alveolar gradient (amount in breath minus amount in air) will be zero. If the VOC is synthesized in the body but not cleared, more leaves in the breath than is inspired from the air, and the alveolar gradient becomes positive. Conversely, if the VOC is cleared from the body but not synthesized, less leaves in the breath than is inspired from the air, and the alveolar gradient becomes negative. Hence, if a VOC is both synthesized and cleared in the body, the polarity of the alveolar gradient will vary with their combined effect: positive if synthesis is greater than clearance, and negative if clearance is greater than synthesis.

FIG. 5: (Prior Art) Metabolism of alkanes. Polyunsaturated fatty acids in cell membranes are degraded to alkanes by lipid peroxidation mediated by oxygen free radicals, resulting in membrane dysfunction and possible cell death. The volatile alkanes are excreted in the breath, but may undergo further metabolism to alkyl alcohols. Potential metabolic pathways to other degradation products and to methylalkanes are speculative.

Figure 6:
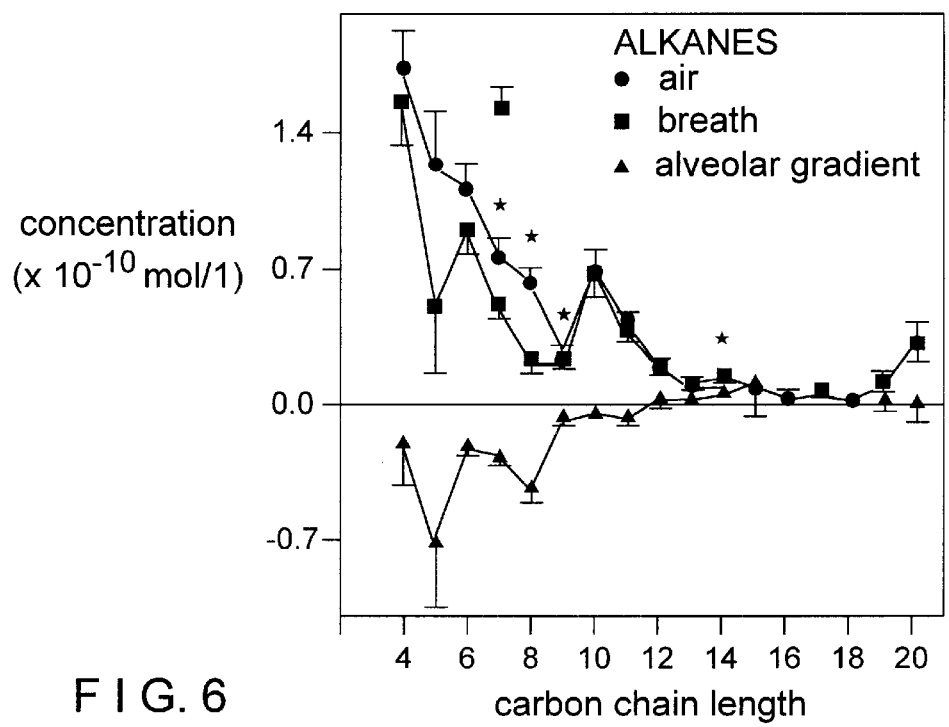

FIG. 6: (Prior Art) Alkanes in breath and air (normal healthy humans). The panel graph shows the abundance of alkanes in breath and air, the alveolar gradients, and their variation with carbon chain length.

Figure 7:
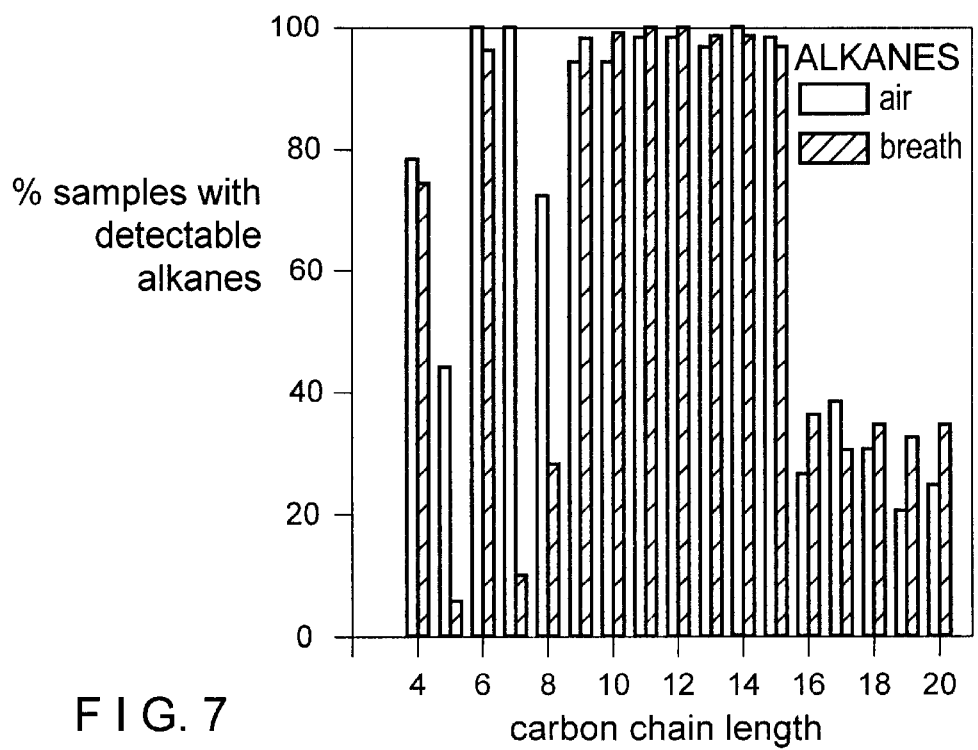

FIG. 7: (Prior Art) The panel shows the frequency distribution of the presence of alkanes in samples of breath and air (normal healthy humans).

Figure 8:
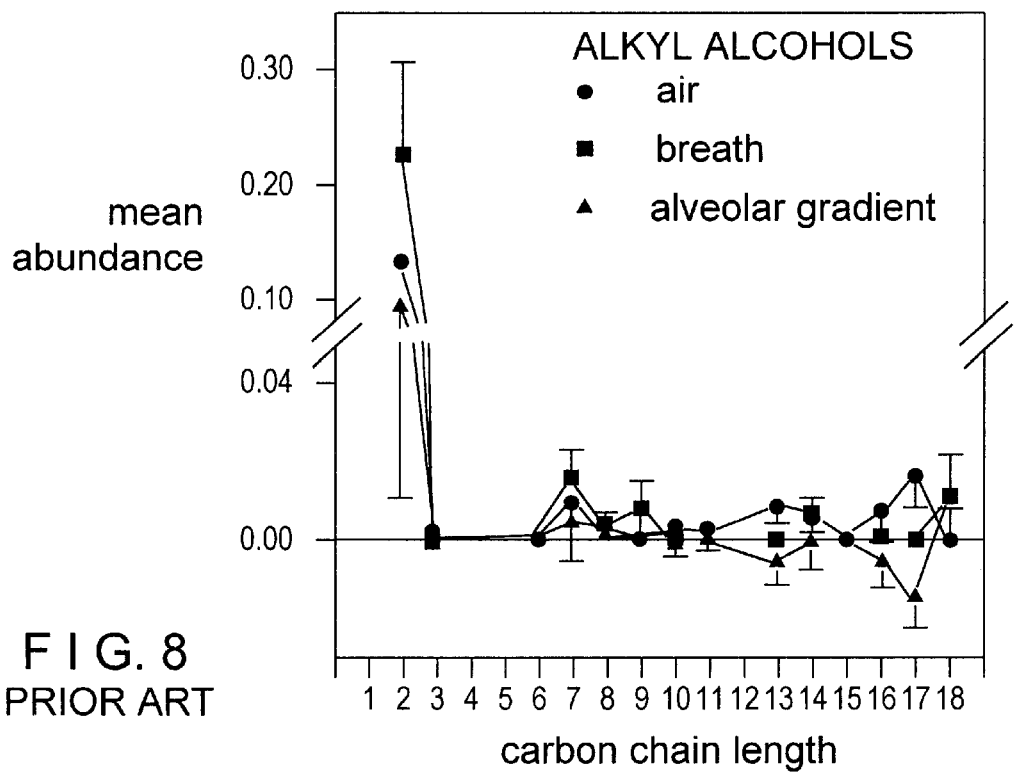

FIG. 8: (Prior Art) Alkyl alcohols in breath and air. The panel shows the abundance of alkyl alcohols in breath and air, the alveolar gradients, and their variation with carbon chain length (normal healthy humans).

Figure 9:
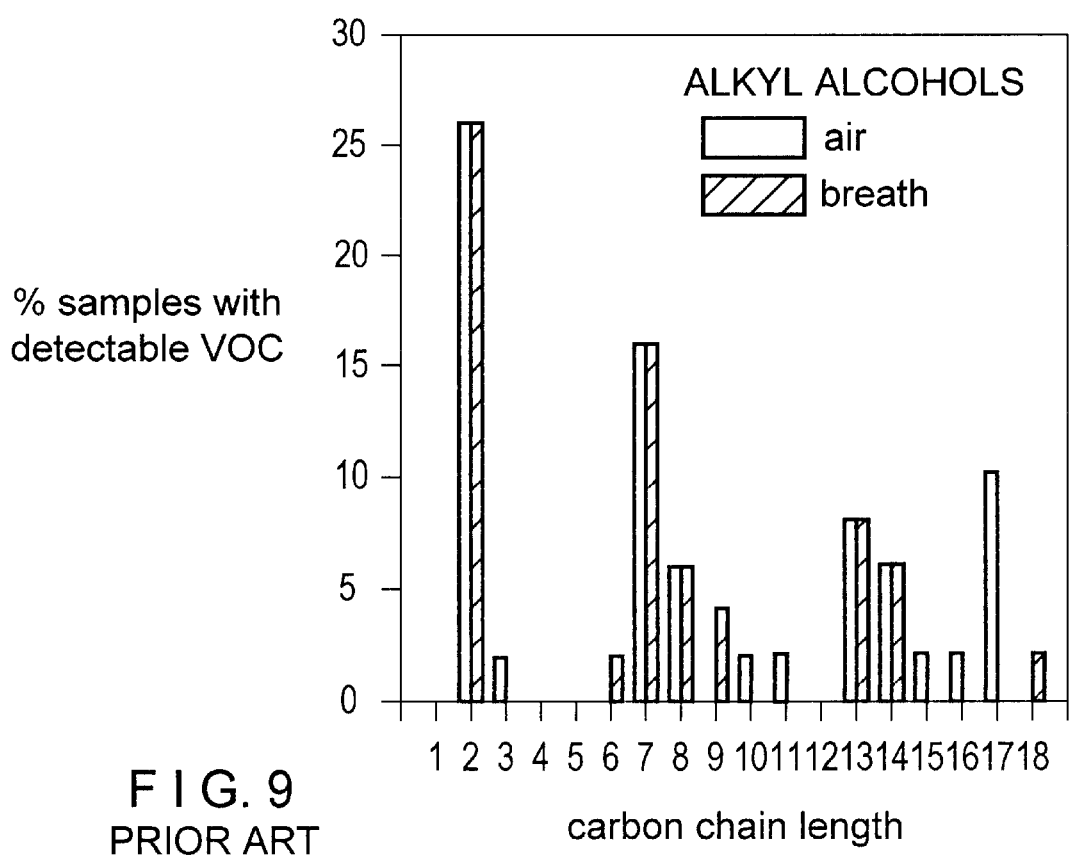

FIG. 9: (Prior Art) The panel shows the frequency distribution of the presence of alkyl alcohols in samples of breath and air (normal healthy humans).

Figure 10:
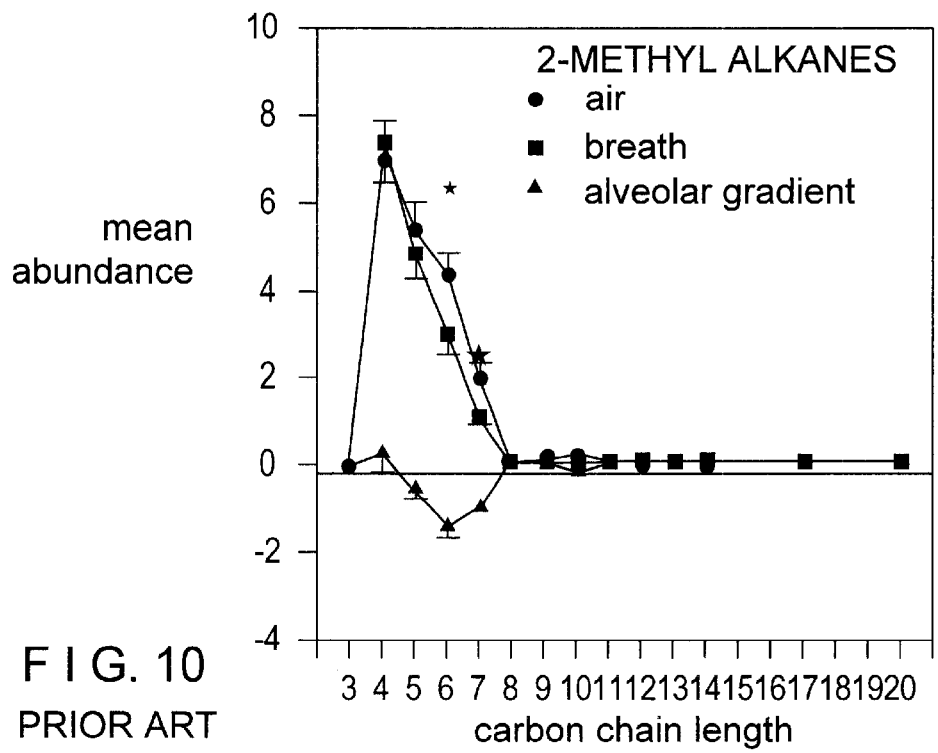

FIG. 10: (Prior Art) Methylalkanes in breath and air. The panel shows the abundance of methylalkanes in breath and air, the alveolar gradients, and their variation with carbon chain length (normal healthy humans).

Figure 11:
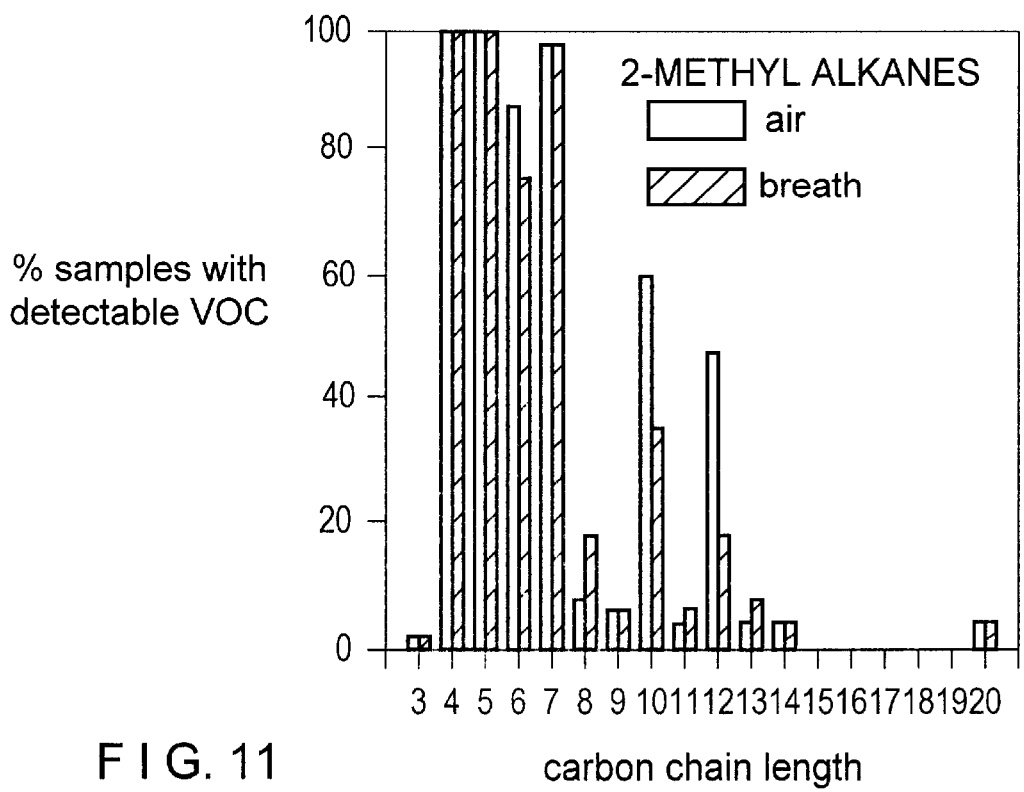

FIG. 11: (Prior Art) The panel shows the frequency distribution of the presence of methylalkanes in samples of breath and air.

FIG. 12: shows graphically women with breast cancer and cancer-free controls: Alkane profile of alveolar breath.

FIG. 13: shows graphically women with breast cancer and cancer-free controls: Alkane profile of room air.

FIG. 14: shows graphically women with breast cancer and cancer-free controls: Alkane profile of alveolar gradient. The alkane profile was displaced downward in the women with breast cancer, compared to the cancer-free controls.

FIG. 15: shows graphically women with breast cancer and cancer-free controls: probability of breast cancer. The data shown in FIG. 14 was analyzed by logistic regression.

Figure 16:
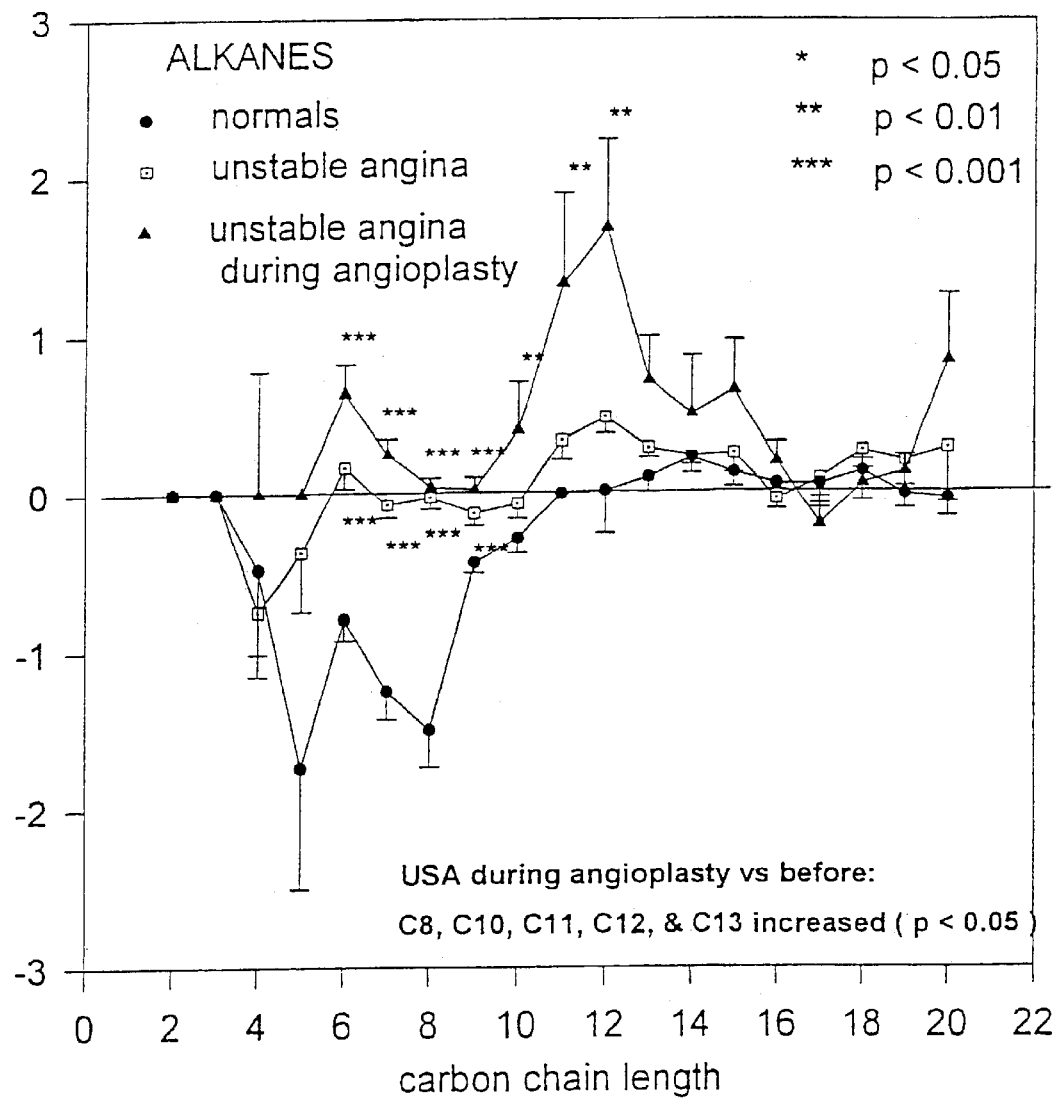

FIG. 16: Breath alkane profiles in normal controls and patients with unstable angina before and during coronary angioplasty: Compared to the normal controls, the breath alkane profile was displaced upwards in the patients with unstable angina. The breath alkane profile was displaced even further upwards during coronary angioplasty while the balloon was inflated.

Figure 17:
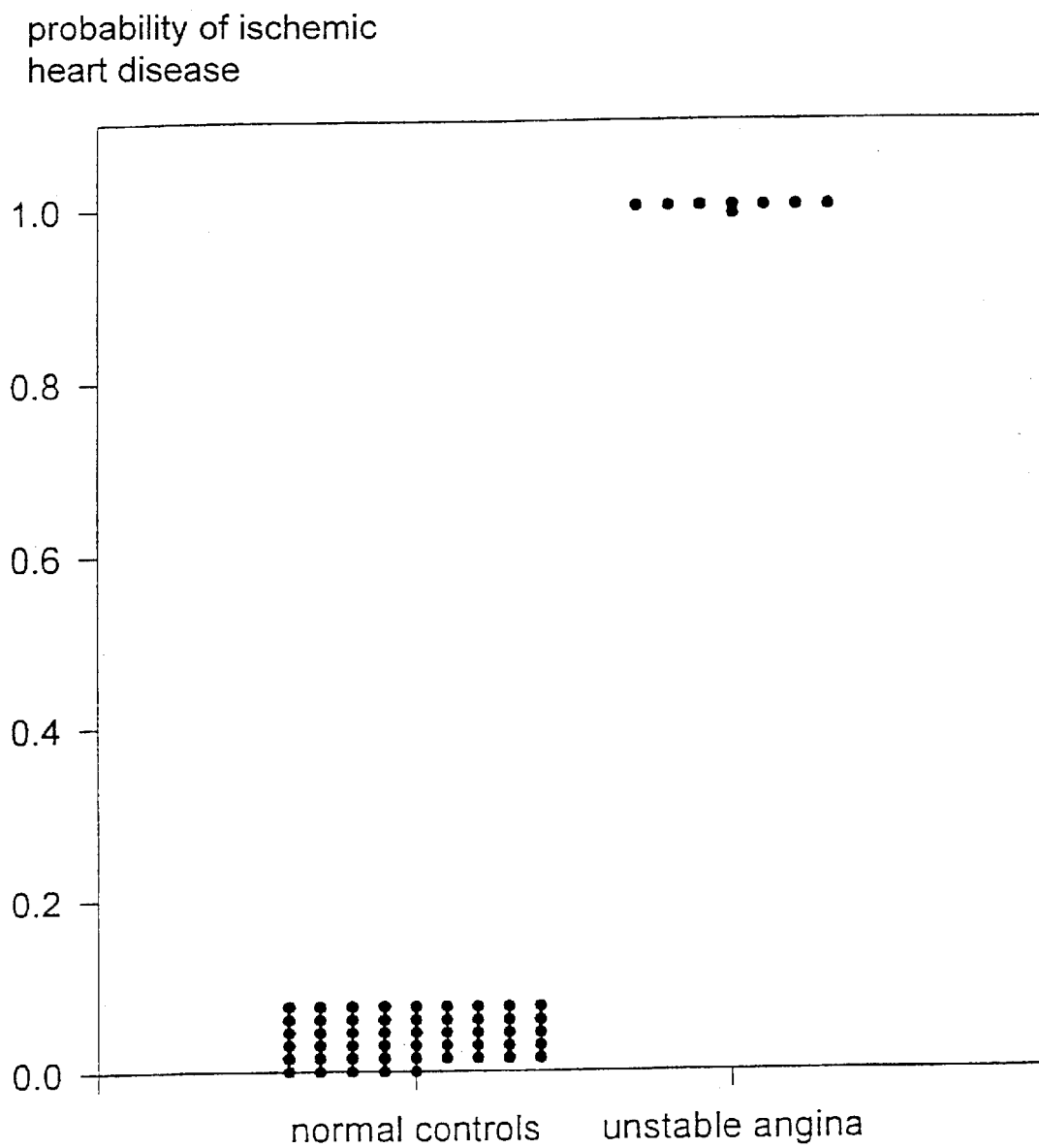

FIG. 17: Probability of ischemic heart disease in normal controls and patients with unstable angina: The data shown in FIG. 16 was analyzed by logistic regression, comparing the normal controls to the patients with unstable angina before they underwent coronary angioplasty. The probability was determined for each subject whether their breath alkane profile belonged to the normal group or to the unstable angina group. The classification accuracy was 100% for both groups.

Figure 18:
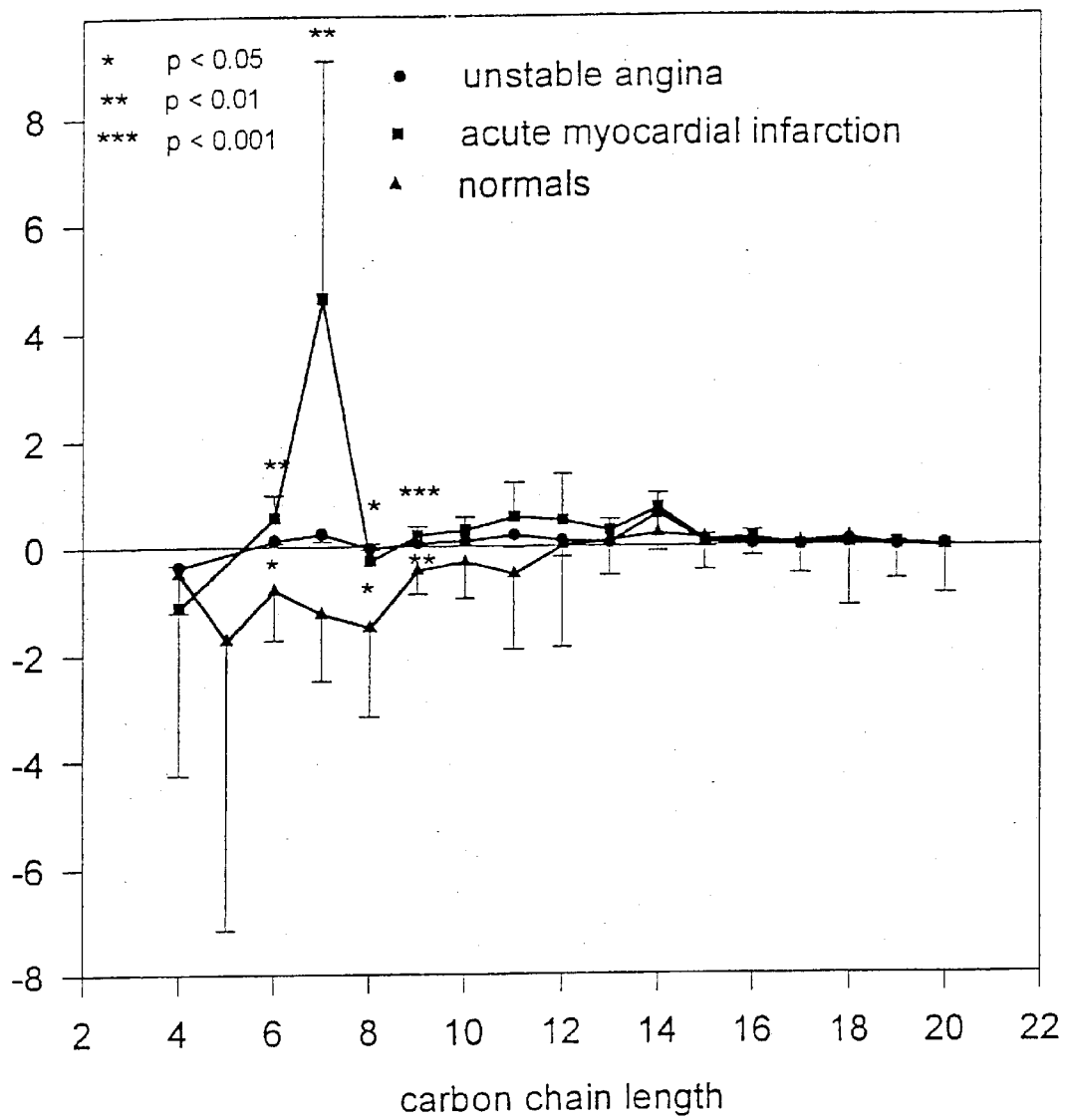

FIG. 18: Breath alkane profiles in normal controls and patients with chest pain due to unstable angina and acute myocardial infarction:

Compared to the normal controls, the breath alkane profile was displaced upwards in the patients with unstable angina. The breath alkane profile was displaced even further upwards in the patients with acute myocardial infarction.

Figure 19:
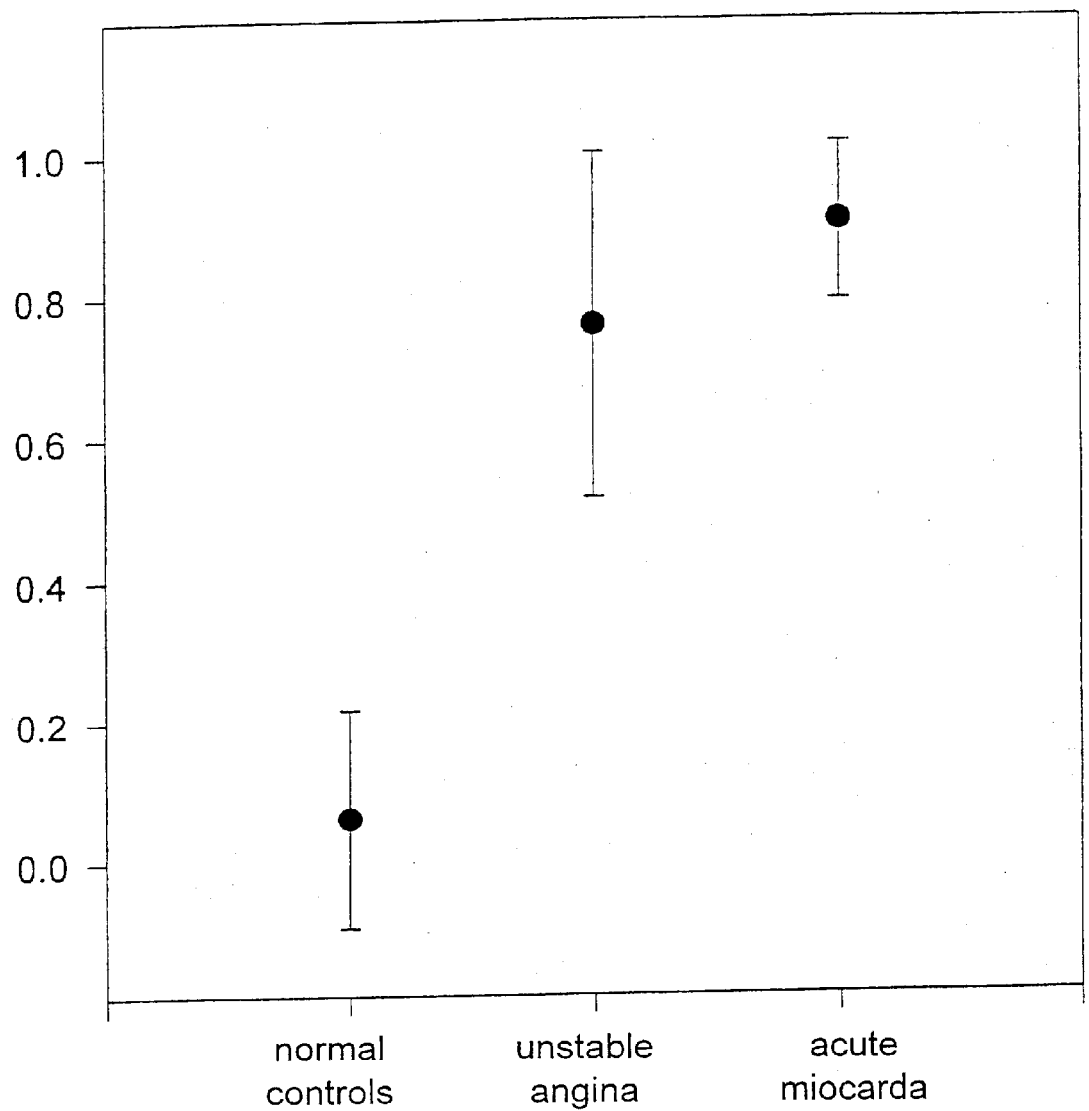

FIG. 19: Probability of ischemic heart disease in normal controls and patients with chest pain due to unstable angina and acute myocardial infarction: The data shown in FIG. 18 was analyzed by logistic regression, comparing the normal controls to the patients with cardiac chest pain. The probability was determined for each subject whether their breath alkane profile belonged to the normal group or to the cardiac chest pain groups (i.e., those with unstable angina or acute myocardial infarction). The classification accuracy was 100% for all groups.

FIG. 20: Probability of acute myocardial infarction in patients with chest pain due to unstable angina and acute myocardial infarction: The data shown in FIG. 18 was analyzed by logistic regression, comparing the two groups of patients with cardiac chest pain. The probability was determined for each subject whether their breath alkane profile belonged to the unstable angina group or the acute myocardial infarction group. The classification accuracy was 100% for both groups.

Figure 21:
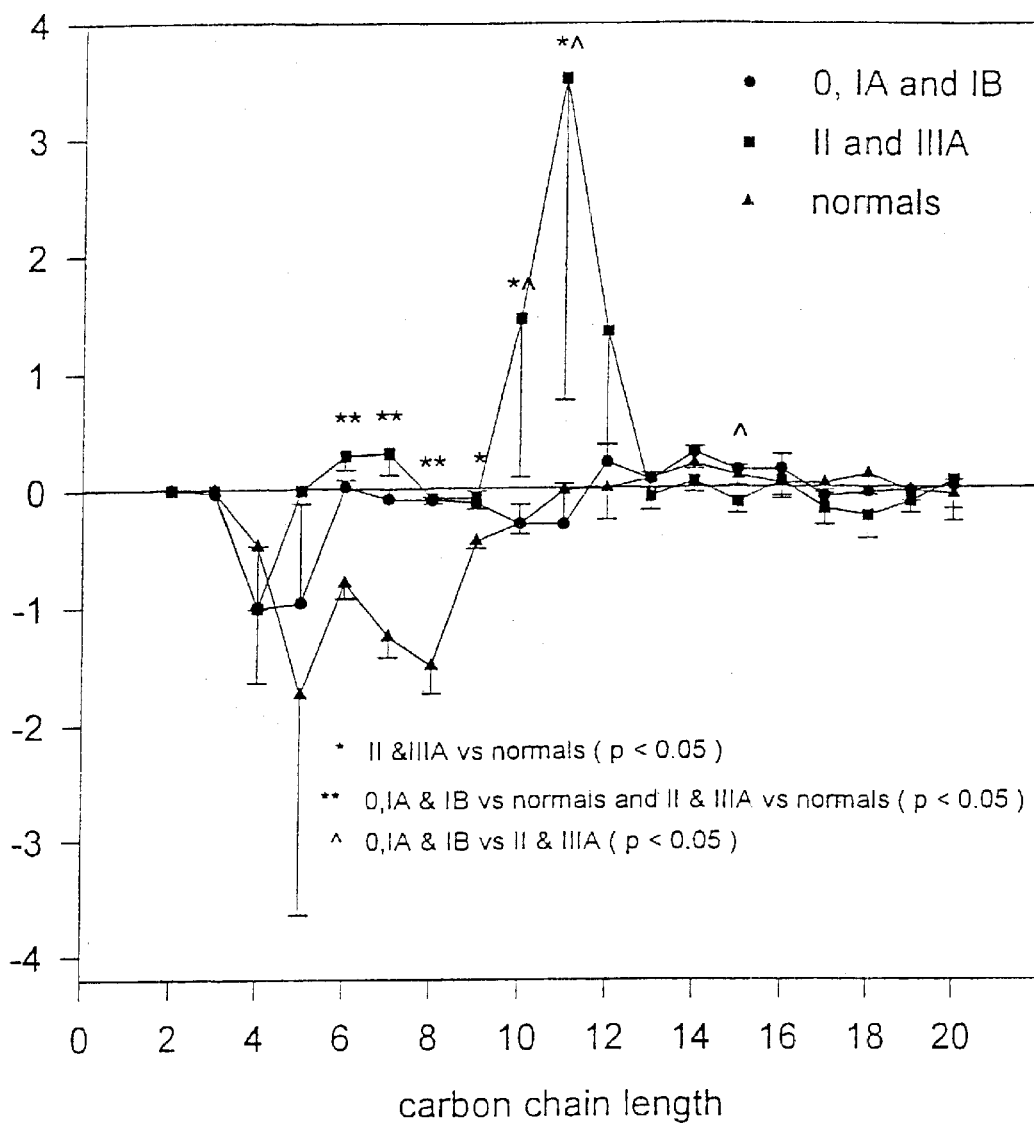

FIG. 21: Breath alkane profiles in normals and heart transplant recipients. Patients with heart transplants were divided into two groups: those requiring no treatment (endomyocardial biopsy with rejection grades 0, 1a and 1b) and those requiring treatment (endomyocardial biopsy with rejection grades II and III). Compared to the normal controls, the breath alkane profile was displaced upwards in the heart transplant recipients requiring no treatment, and an even further upwards in the heart transplant recipients requiring treatment.

Figure 22:
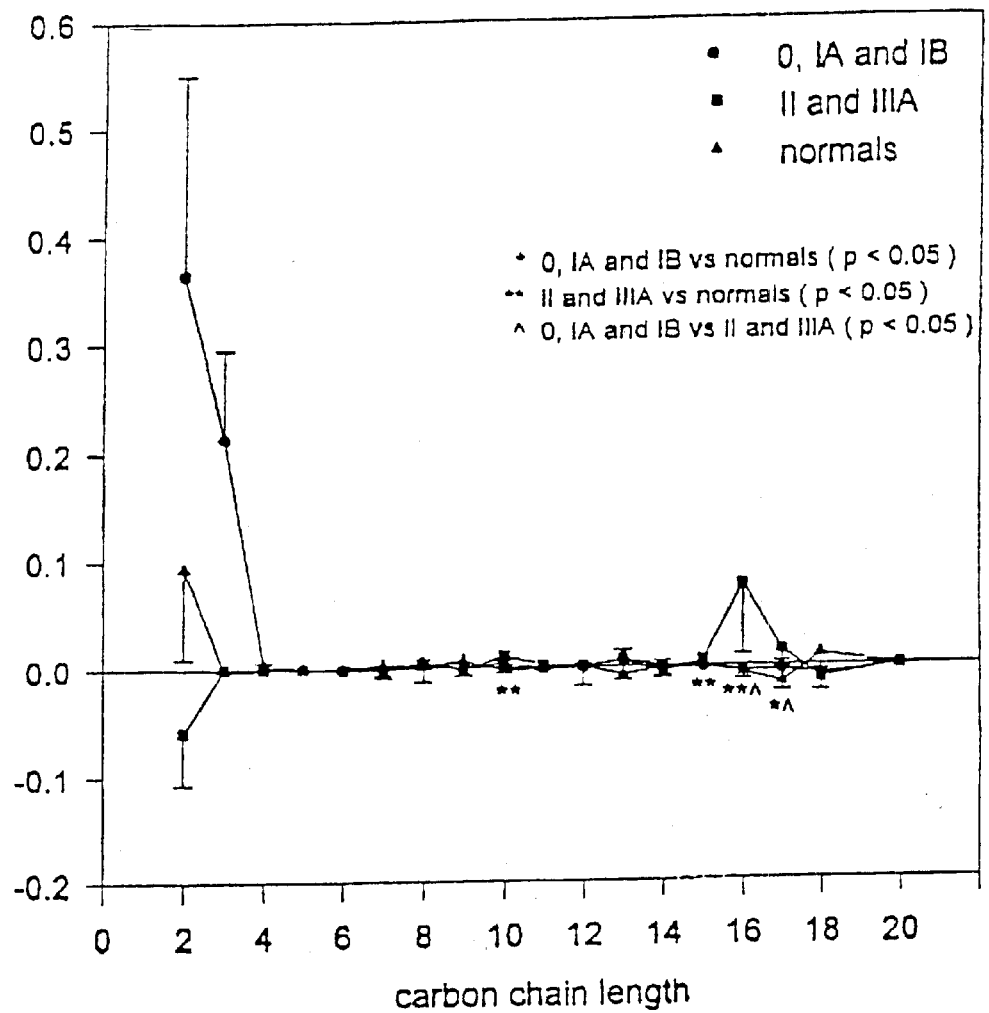

FIG. 22: Breath alkyl alcohol profiles in normals and heart transplant recipients. Patients with heart transplants were divided into two groups: those requiring no treatment (endomyocardial biopsy with rejection grades 0, 1a and 1b) and those requiring treatment (endomyocardial biopsy with rejection grades II and III). Compared to the normal controls, the breath alkyl alcohol profile was displaced upwards in the heart transplant recipients requiring no treatment, and even further upwards in the heart transplant recipients requiring treatment.

Figure 23:
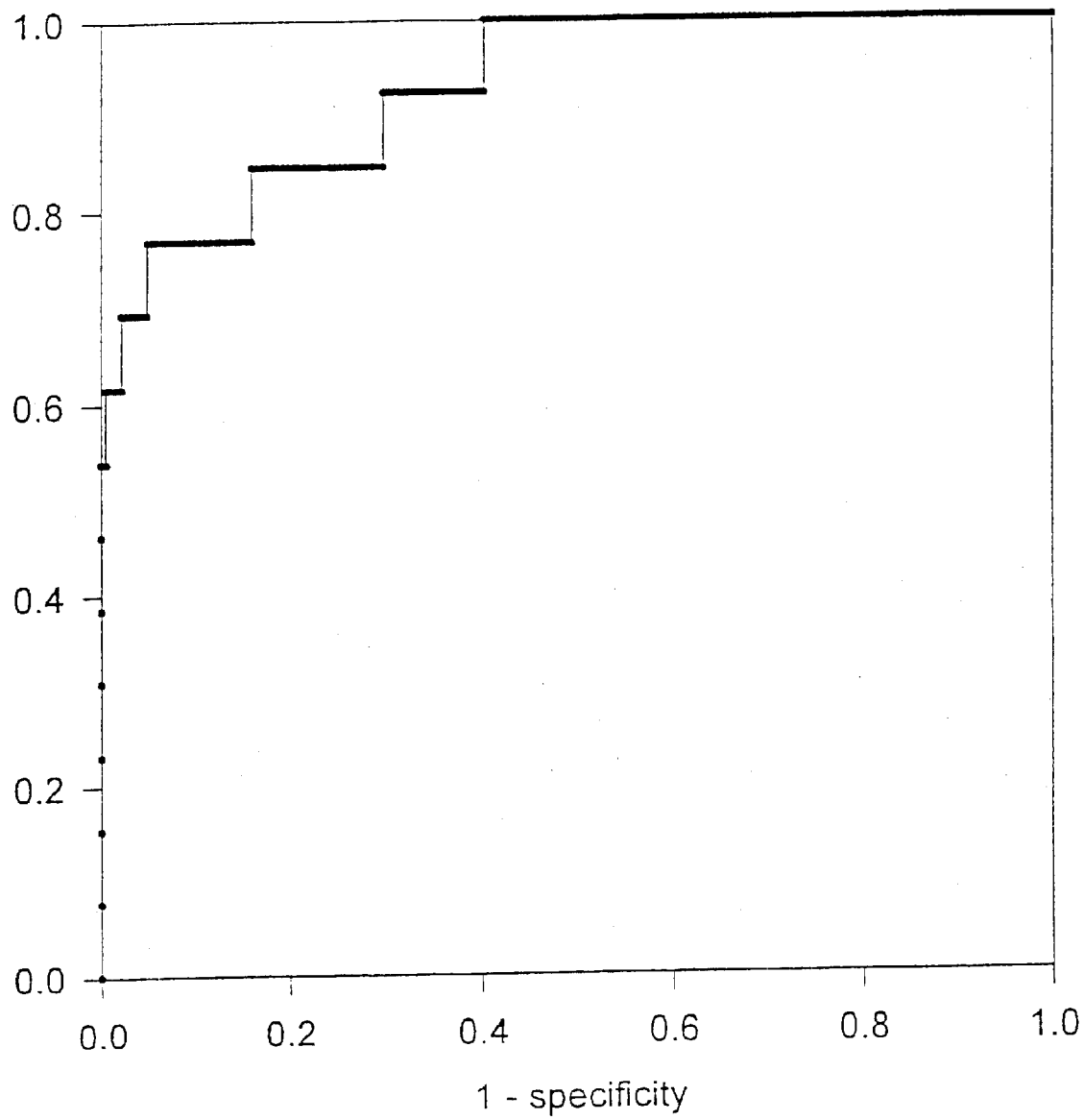

FIG. 23: Receiver operating characteristic (ROC) curve of the breath test for heart transplant rejection. Patients with heart transplants were divided into two groups: those requiring no treatment (endomyocardial biopsy with rejection grades 0, 1a and 1b) (n=182) and those requiring treatment (endomyocardial biopsy with rejection grades II and III) (n=13). The two groups were compared by logistic regression, employing the combination of the breath alkane profiles and breath alkyl alcohol profiles shown in FIGS. 21 and 22. The ROC curve displays the sensitivity and specificity of the test. At the shoulder of the curve, the breath test was 84.6% sensitive and 80.2% specific.

Figure 24:
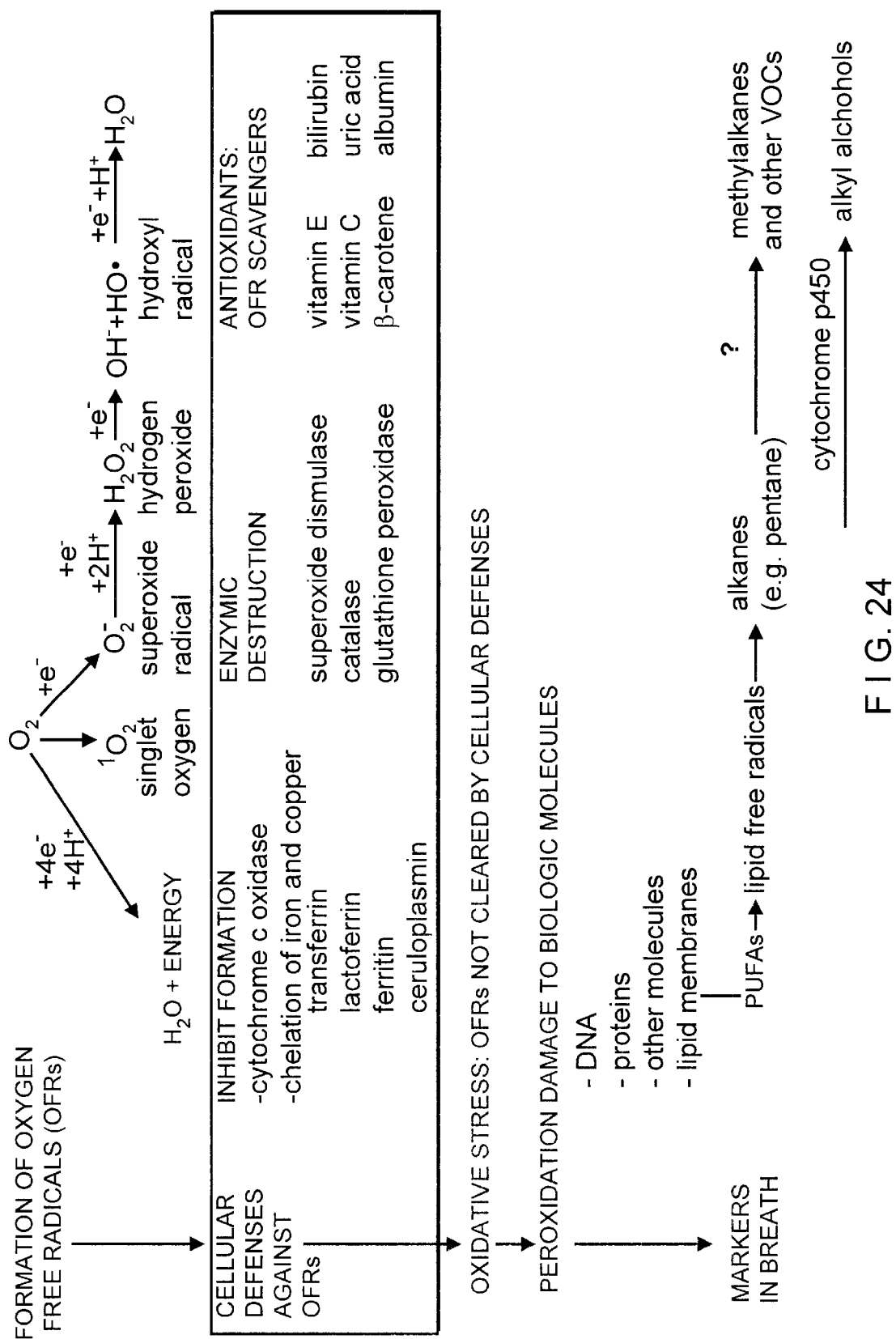

FIG. 24: Manufacture and effects of reactive oxygen species (ROS). ROS are toxic byproducts of normal oxidative metabolism. This figure demonstrates the manufacture of ROS and the cellular defense mechanisms to clear them. Oxidative stress is determined by the size of the ROS pool. Polyunsaturated fatty acids (PUFAs) in cell membranes are degraded to alkanes by lipid peroxidation, resulting in membrane dysfunction and possible cell death. Metabolic products of PUFAs are excreted in the breath as volatile organic compounds (VOCs), principally alkanes, alkyl alcohols and possibly methylalkanes.

FIG. 25: Alkanes in breath and air. The upper panel shows the mean concentrations of alkanes in breath and air, their alveolar gradients (concentration in breath minus concentration in air), and their variation with carbon chain length. Asterisks indicate significant differences between concentrations in breath and air ($p<0.05$). The lower panel shows the frequency distributions of their presence in samples of breath and air.

Figure 26:
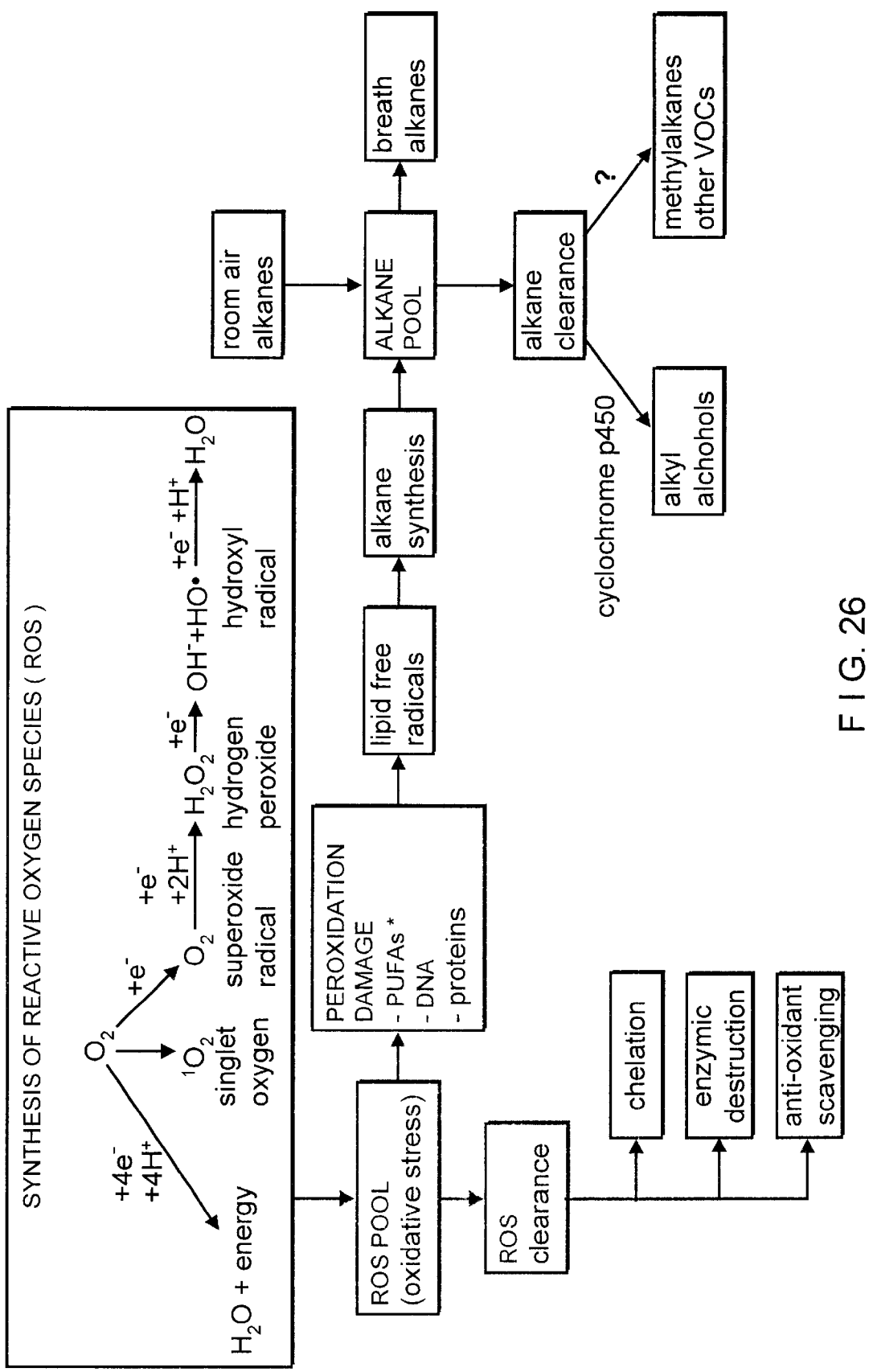

FIG. 26: Manufacture and effects of reactive oxygen species (ROS). ROS are toxic byproducts of normal oxidative metabolism. This figure demonstrates the manufacture of ROS and the cellular defense mechanisms to clear them. Oxidative stress is determined by the size of the ROS pool. Polyunsaturated fatty acids (PUFAs) in ell membranes are degraded to alkanes by lipid peroxidation, resulting in membrane dysfunction and possible cell death. Metabolic products of PUFAs are excreted in the breath as volatile organic compounds (VOCs), principally alkanes, alkyl alcohols and possibly methylalkanes. (Modified from refs. 2 and 18).

FIG. 27: Alkanes in breath and air. The upper panel shows the mean concentrations of alkanes in breath and air, their alveolar gradients (concentration in breath minus concentration in air), and their variation with carbon chain length. Asterisks indicate significant differences between concentrations in breath and air ($p<0.05$). The lower panel shows the frequency distributions of their presence in samples of breath and air.

Figure 28:
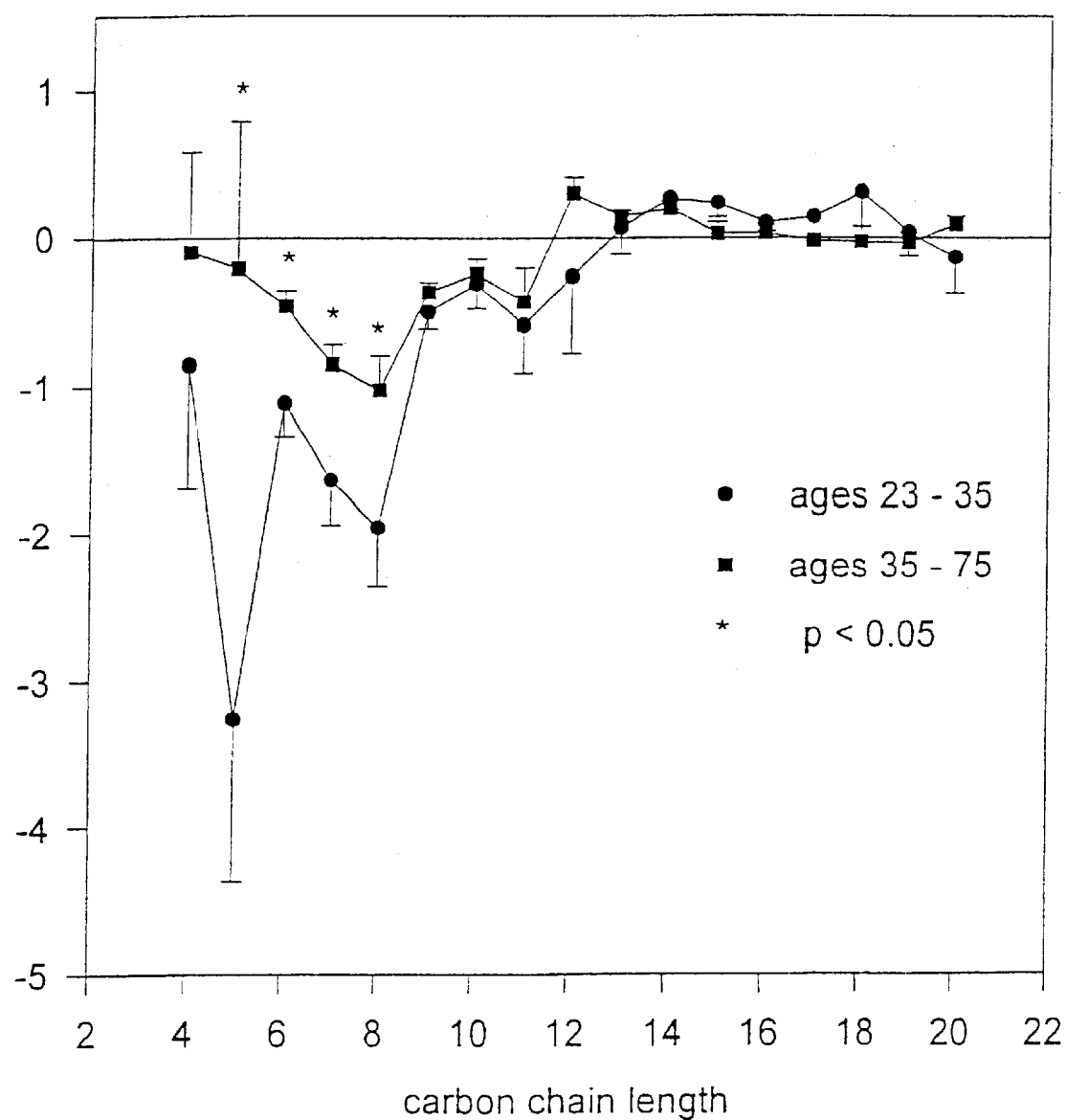

FIG. 28: Effect of age on the breath alkane profile. The profile of alveolar gradients is shown for the younger and older half of the normal subjects. The significant increases in alkanes in the older subjects were consistent with increased oxidative stress, though reduced clearance of alkanes may have contributed.

Figure 29:
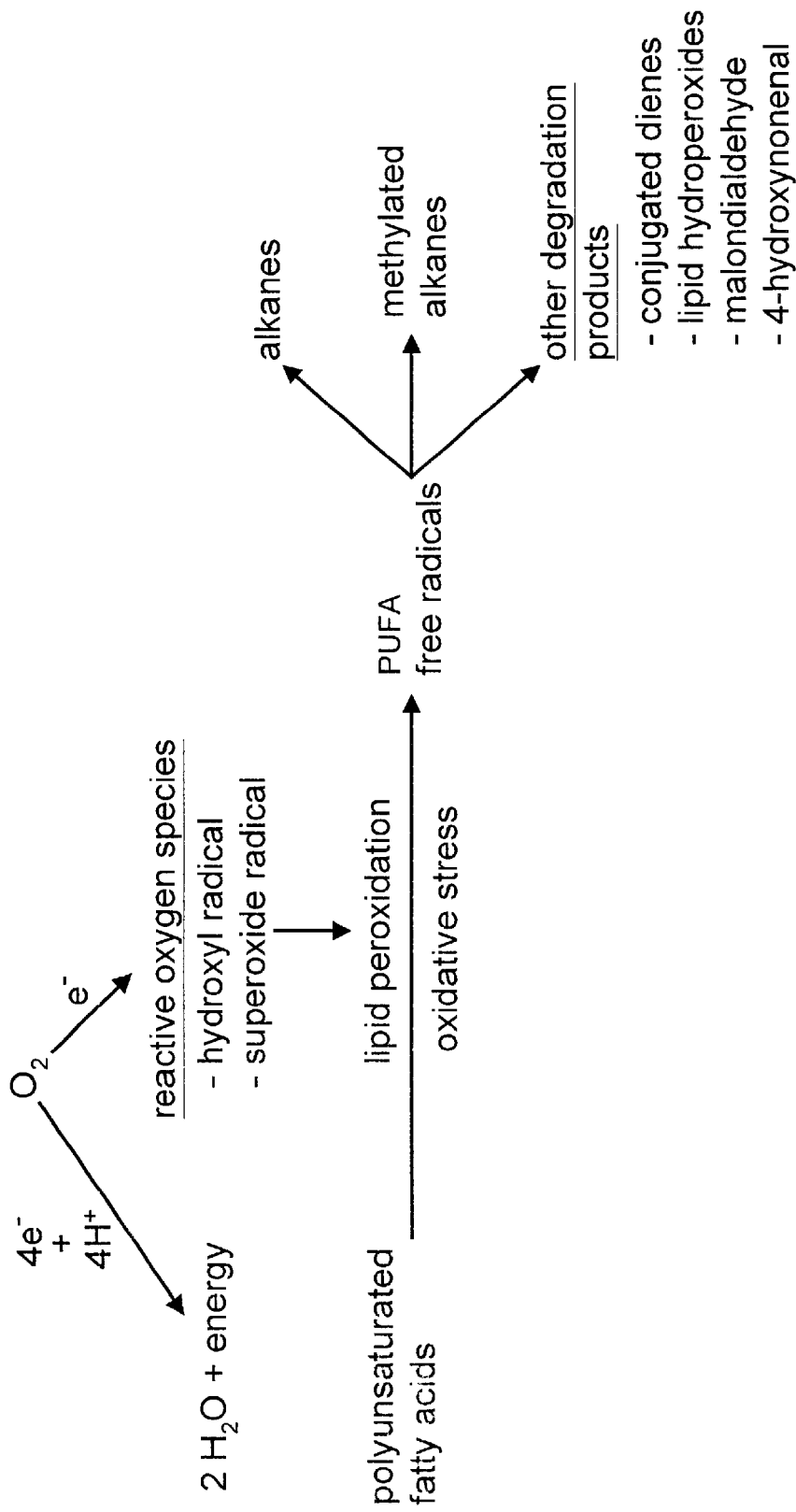

FIG. 29: Origin of oxidative stress and the generation of metabolic markers

FIG. 30: Breath methylated alkane contour—mean of 99 normal subjects. Note that this figure also includes n-alkanes as methylated at C1. For example an alkane with carbon chain length=4 (butane) if methylated at C1 becomes the C5 alkane pentane The mean BMACs are shown for all subjects, younger subjects and older subjects in, 3 and 4 respectively.

Figure 31:
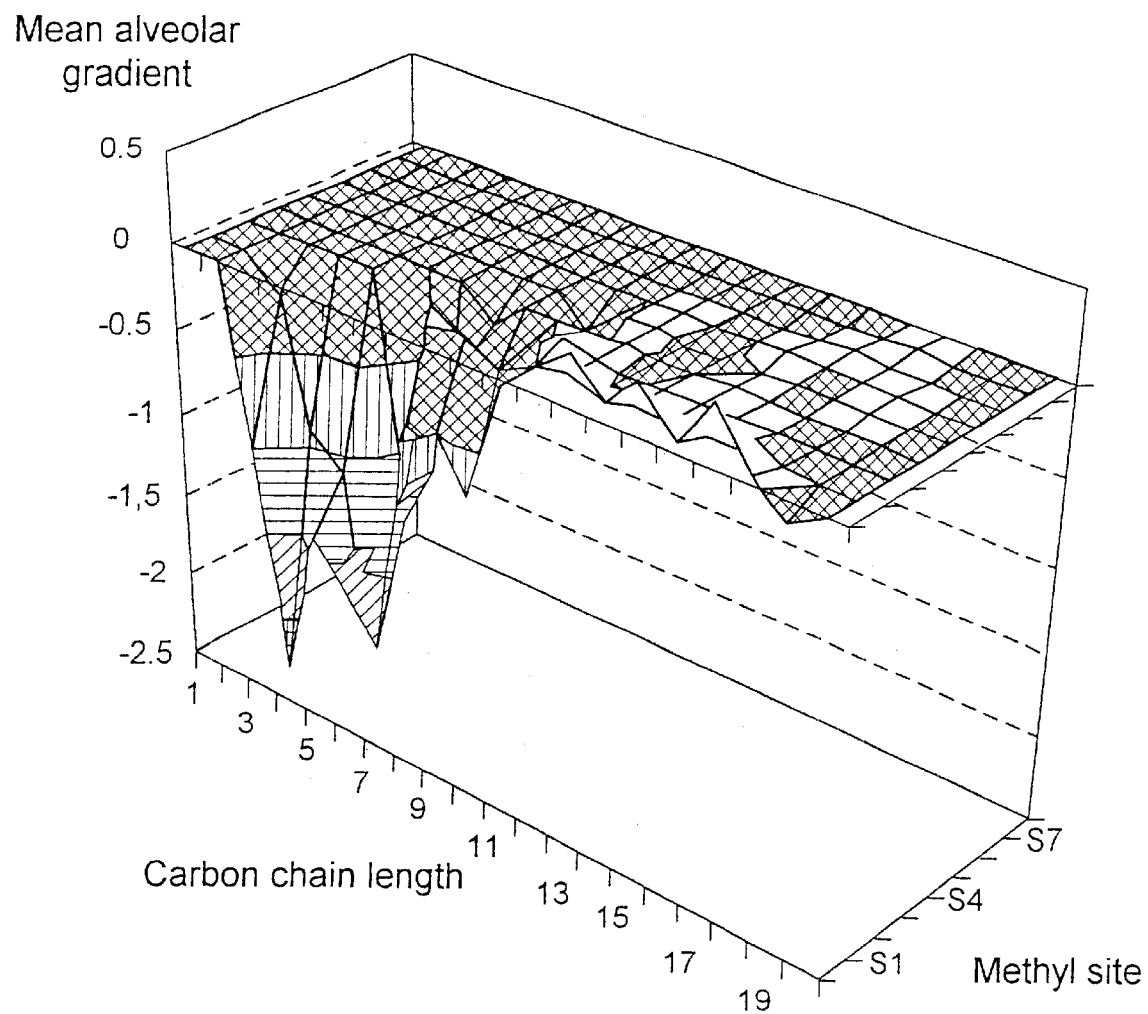

FIG. 31: Breath methylated alkane contour—mean younger subjects. The mean BMAC of 49 normals aged 9 to 40 is shown.

Figure 32:
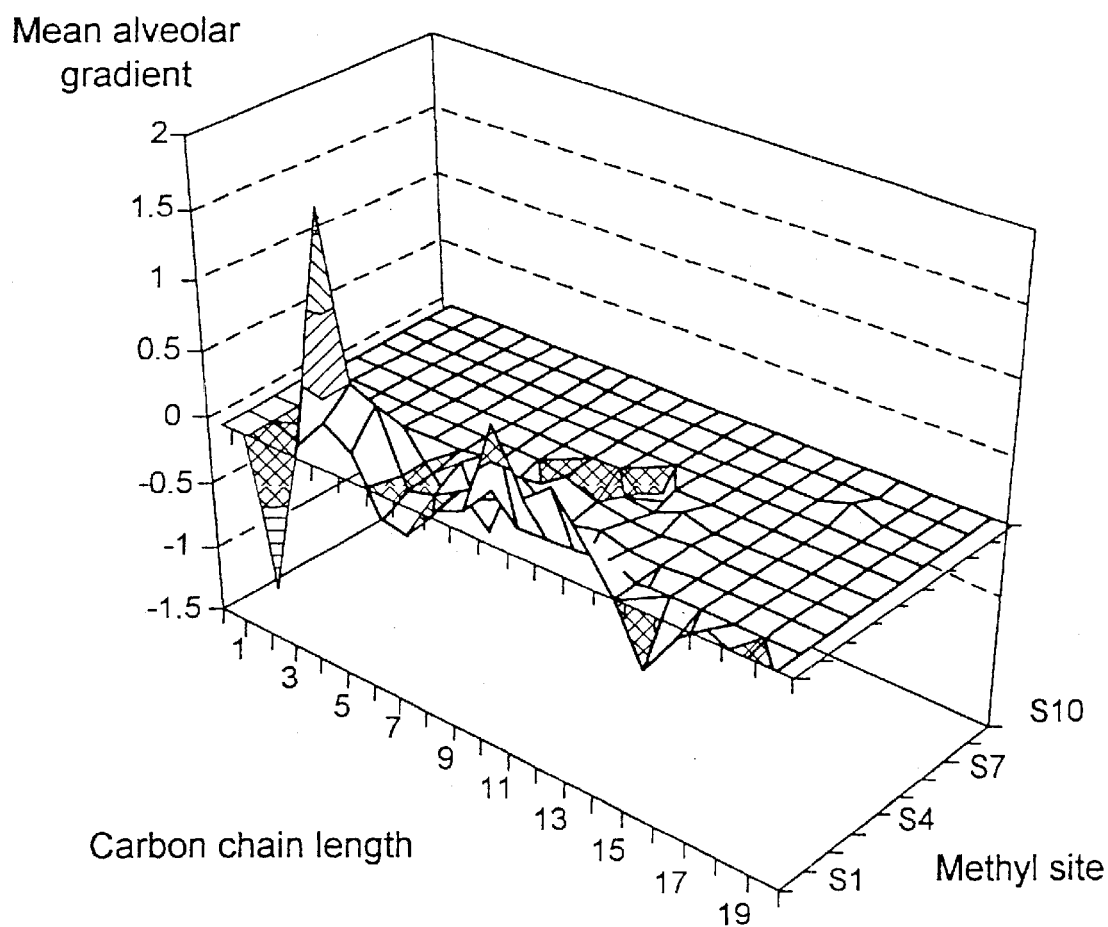

FIG. 32: Breath methylated alkane contour—mean of older subjects. The mean BMAC of 50 normals aged 40 to 89 is shown. Note that several peaks were elevated in comparison to the mean BMAC of the younger normals. 25 of these were statistically significant (see Table 1)

Figure 33:
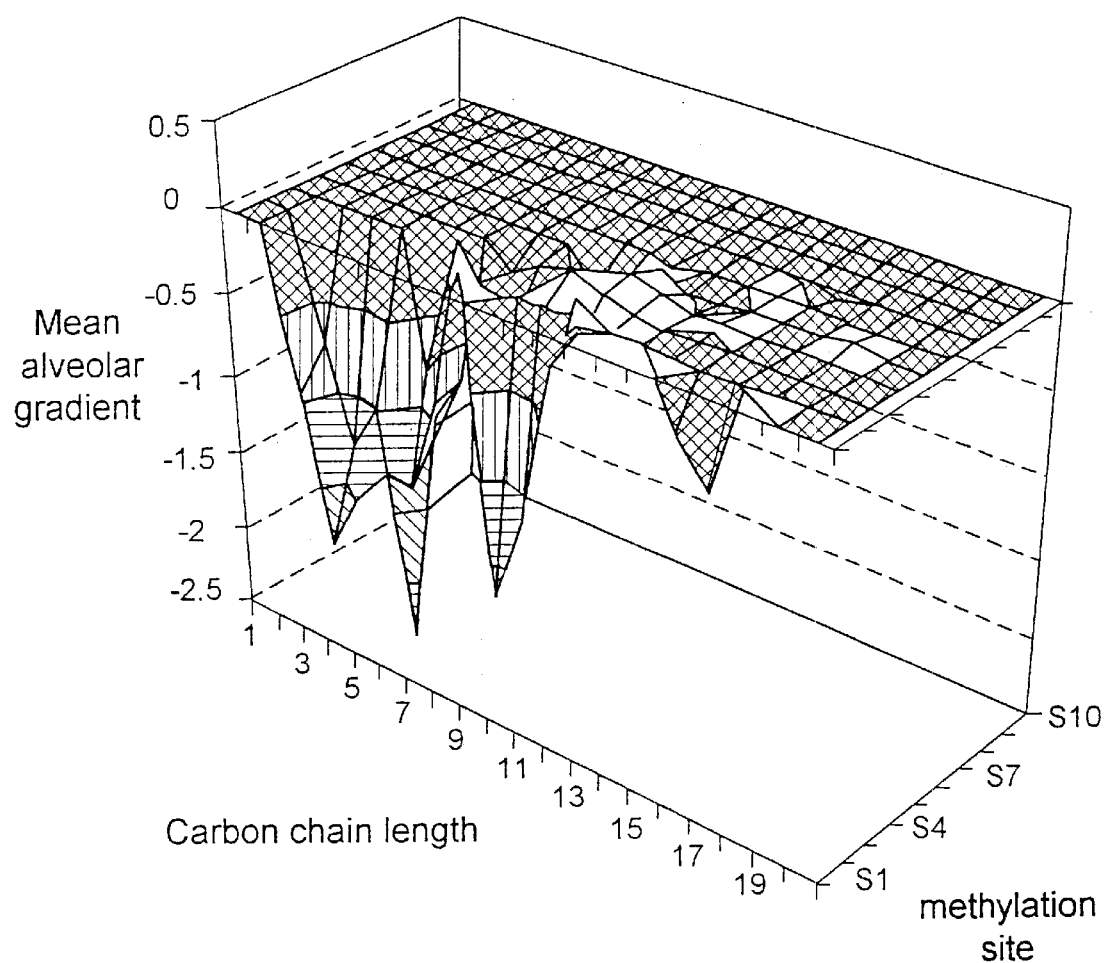

FIG. 33: Breath methylated alkane contour—mean of smokers. The mean BMAC of 11 smokers is shown.

Figure 34:
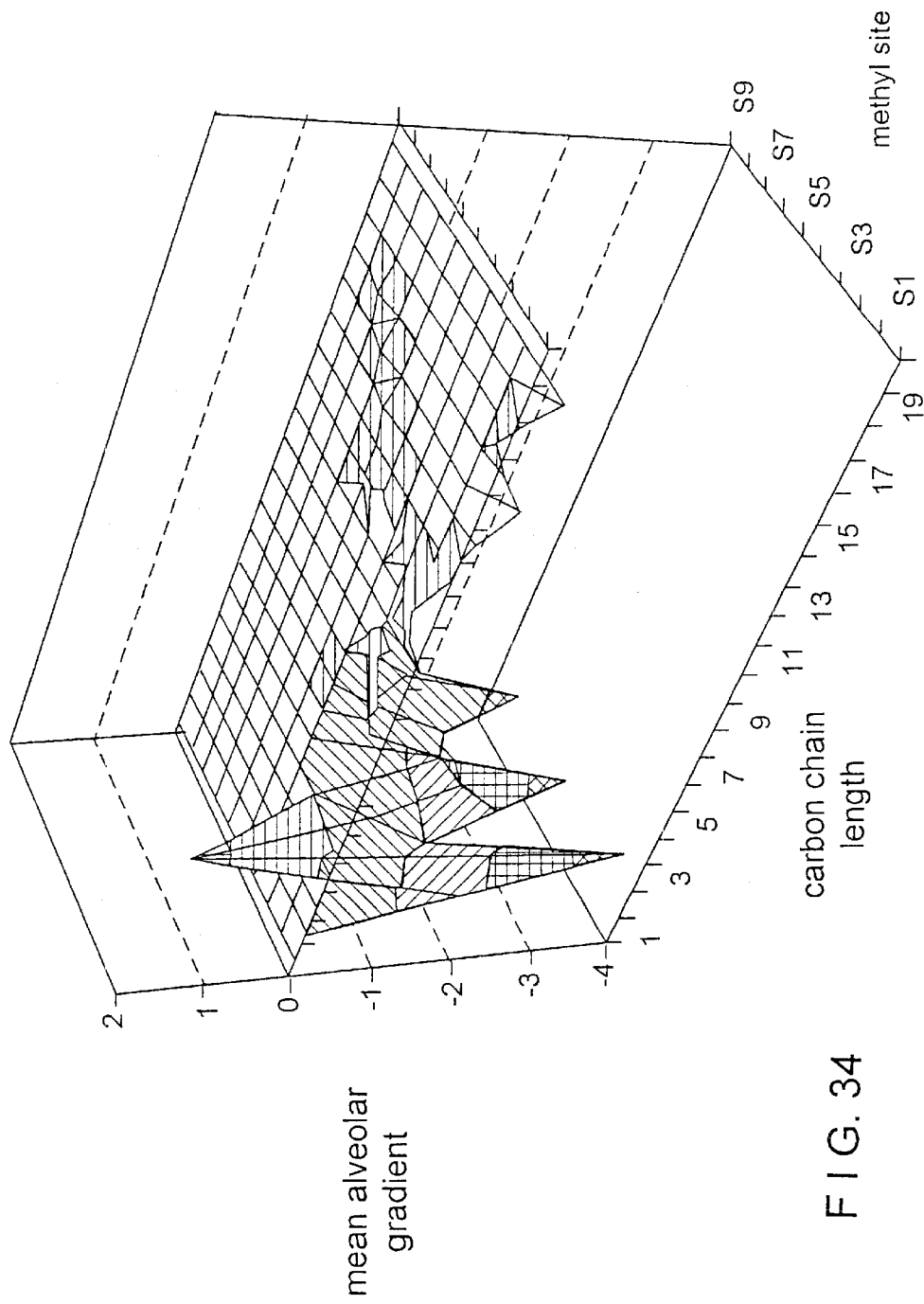

FIG. 34: Breath methylated alkane contour—mean of non-smokers. The mean BMAC of 11 non-smokers is shown, matched in age to the smokers shown in FIG. 33.

Figure 35:
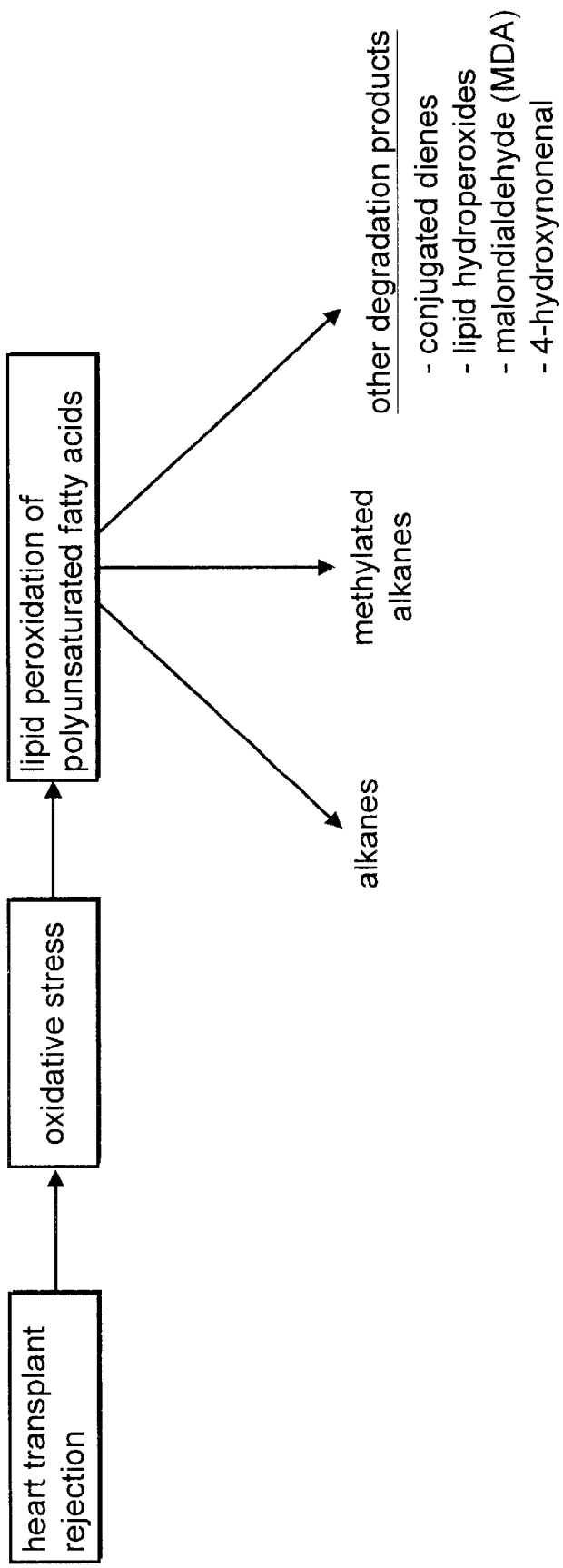

FIG. 35: Relationship between heart transplant rejection and VOCs in breath. Heart transplant rejection elicits the formation of reactive oxygen species (ROS) in the myocardium, which degrade polyunsaturated fatty acids (PUFAs) to alkanes and other degradation products. The origin of the methylated alkanes is unknown; possible pathways include degradation of PUFAs or methylation of alkanes. Alkanes and methylated alkanes are volatile organic compounds (VOCs) which are excreted in the breath.

Figure 36:
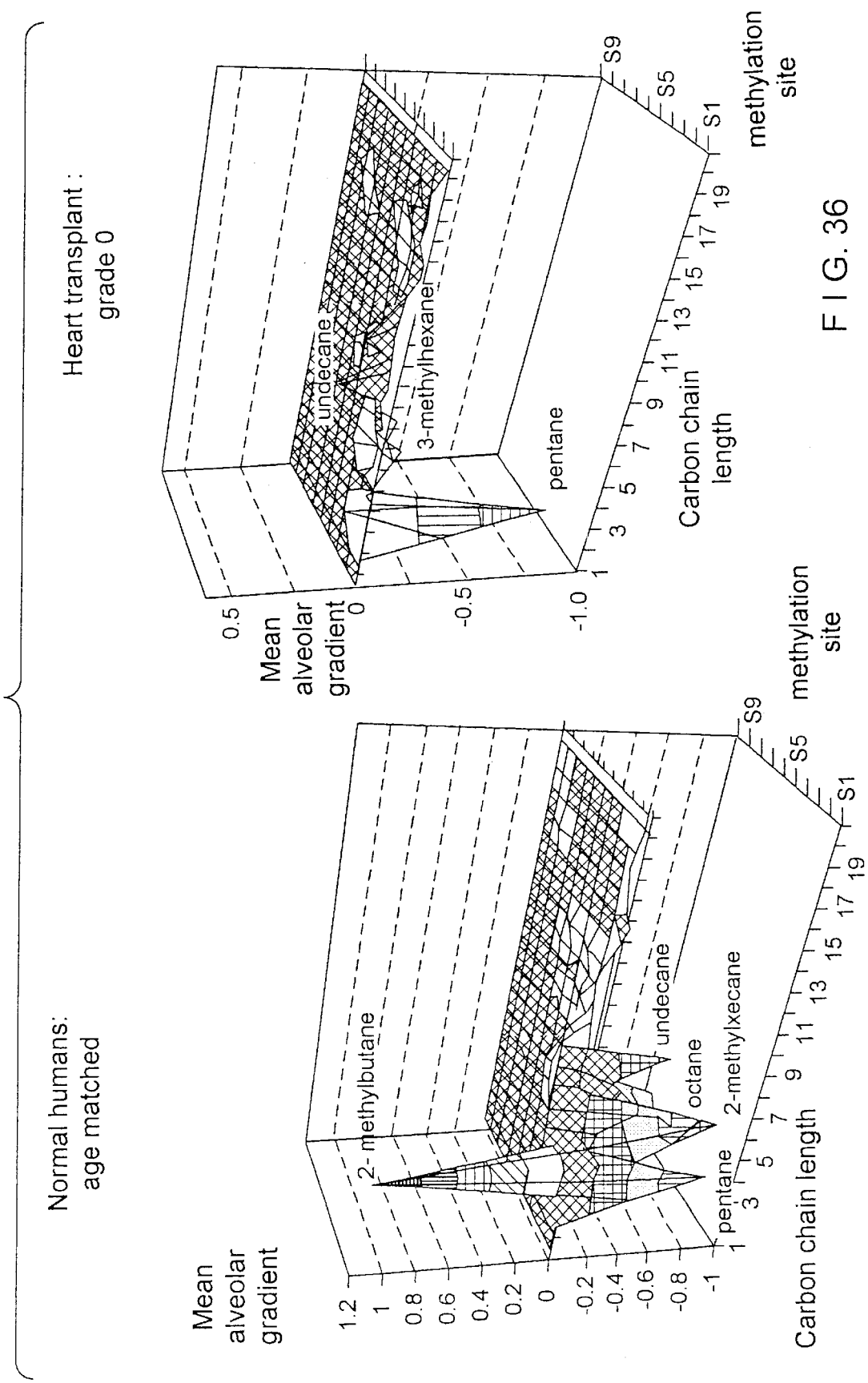

FIG. 36: Breath methylated alkane contour—Differences between transplant recipients and normals: The mean BMACs of heart transplant recipients with Grade 0 rejection (i.e. no histological evidence of rejection) and age-matched normal controls are shown. Note that a number of peaks which are strongly negative in the normals are not so apparent in the heart transplant recipients. VOCs which were significantly different are shown in Table 3.

Figures 37A, 37B:
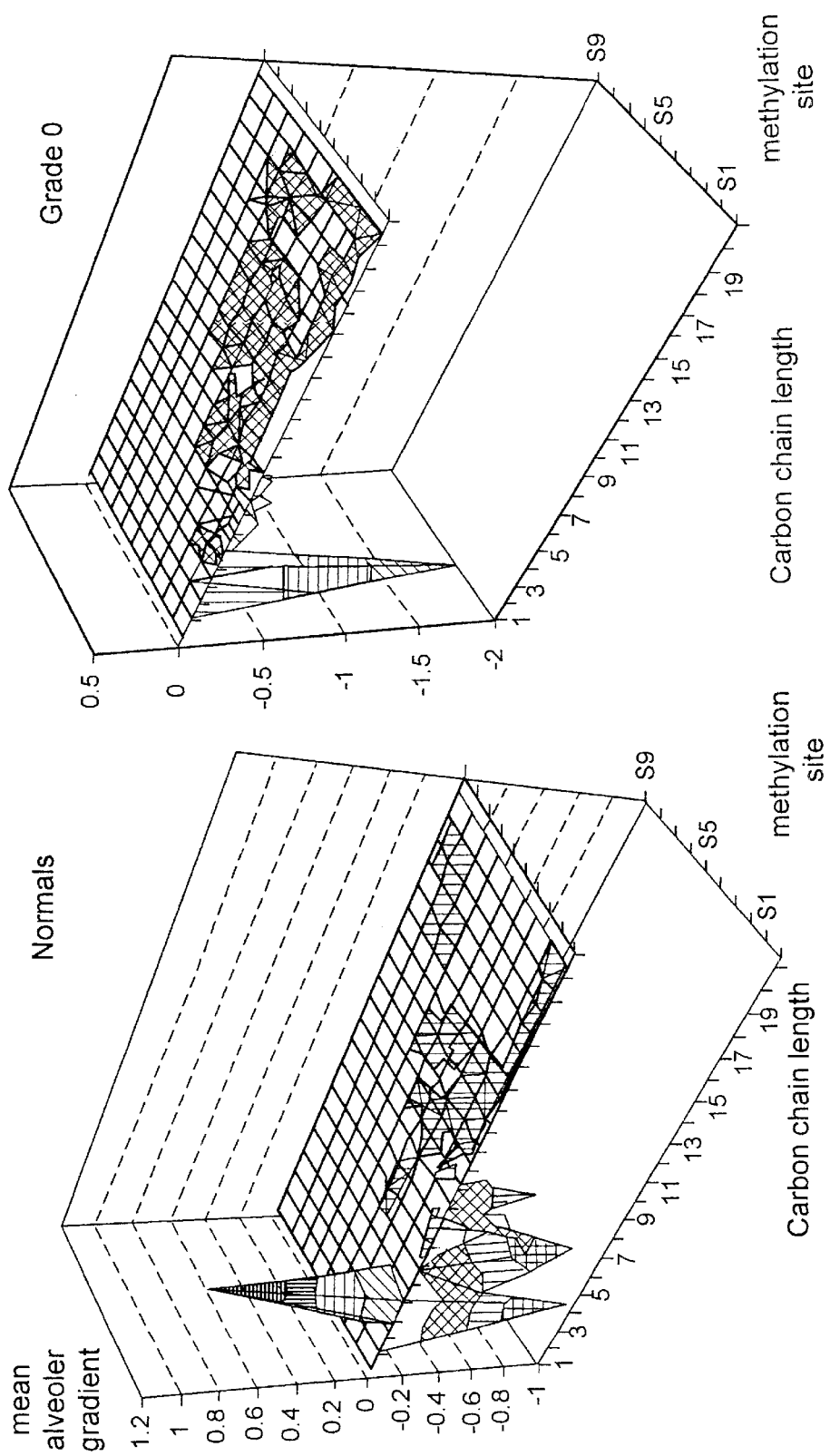
Figures 37C, 37D:
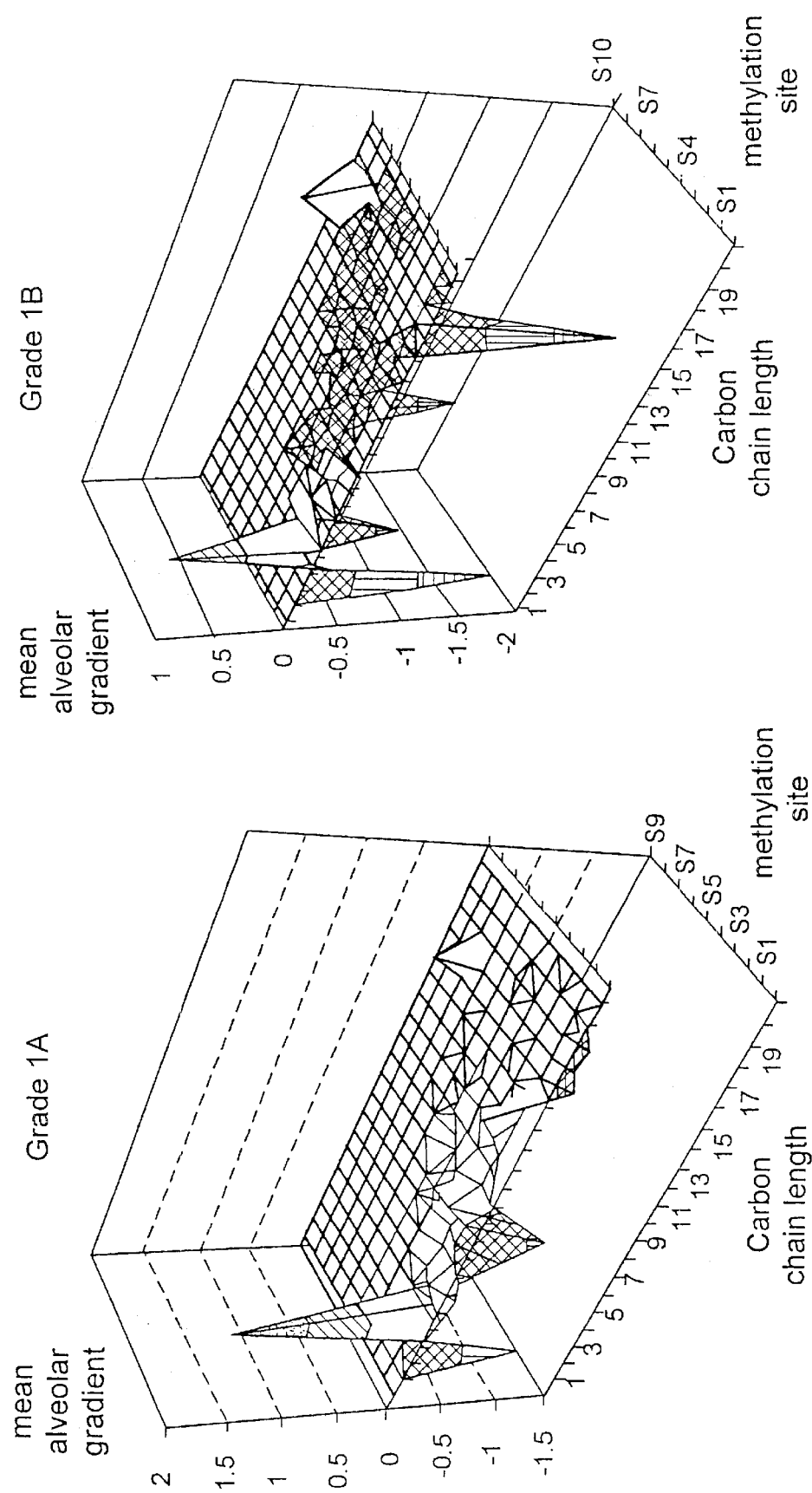
Figures 37E, 37F:
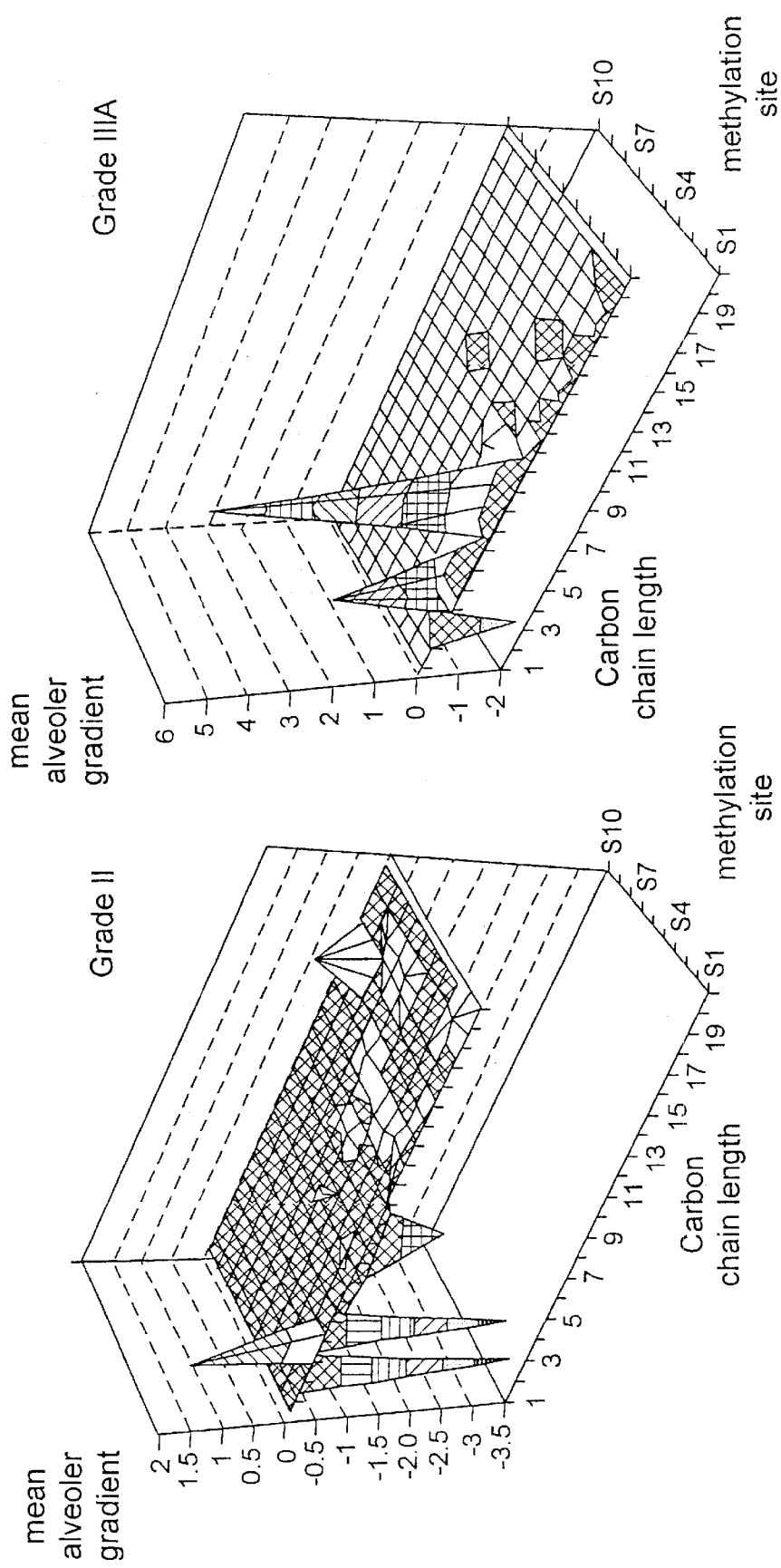

FIG. 37: Breath methylated alkane contour Differences between heart transplant recipients with different grades of rejection: The mean BMACs of heart transplant recipients with Grade 0, Grade 1a and 1b, Grade II and Grade IIIa rejection are shown in FIG. 37. VOCs which were significantly different in patients with Grade 0 and Grade IIIa rejection are shown in Table 4.

Figure 38:
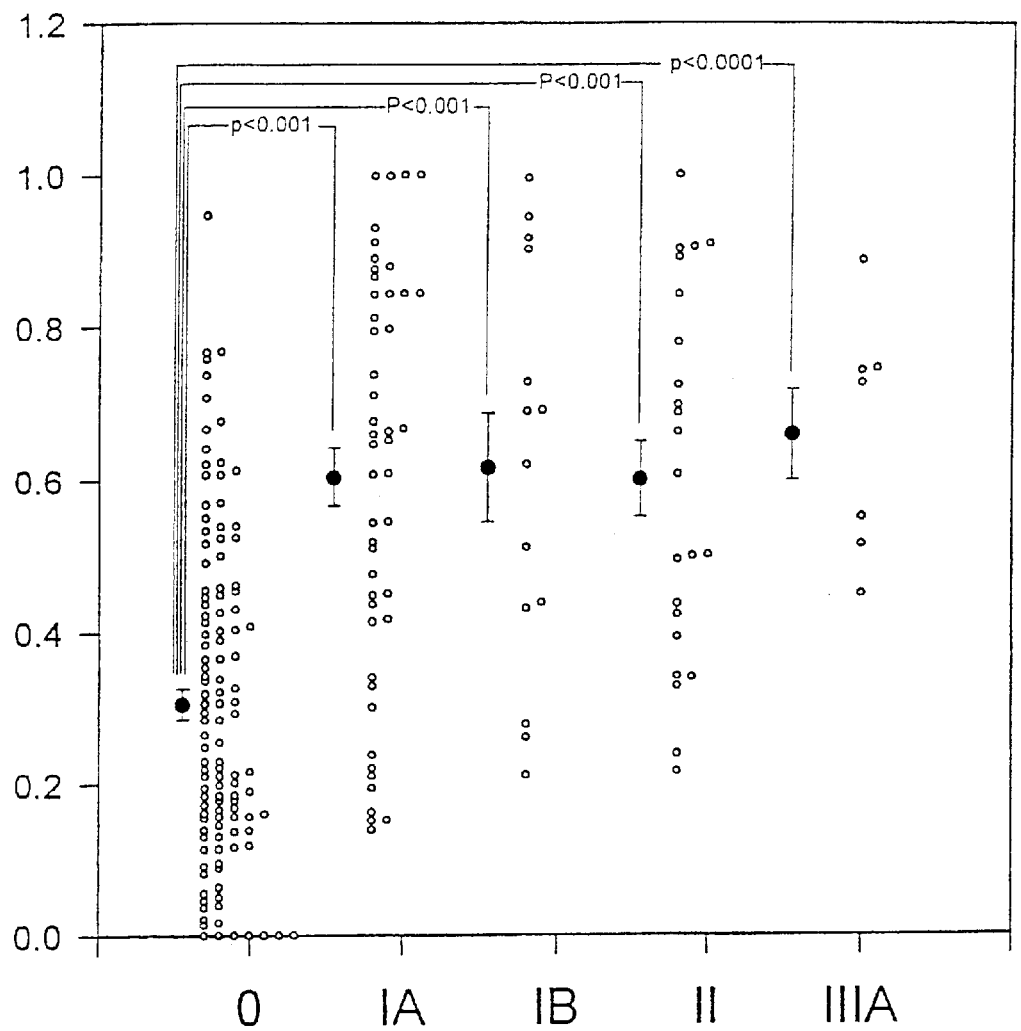

FIG. 38: Scatter diagram of the probability of rejection in all subjects. The probability of heart transplant rejection was determined by dividing the heart transplant recipients into two groups: those with no evidence of rejection (Grade 0) and those with any evidence of rejection (Grades 1a and 1b, II and IIIa). The BMACs of the patients in the two groups were compared by logistic regression, to generate a probability of rejection.

Figure 39:
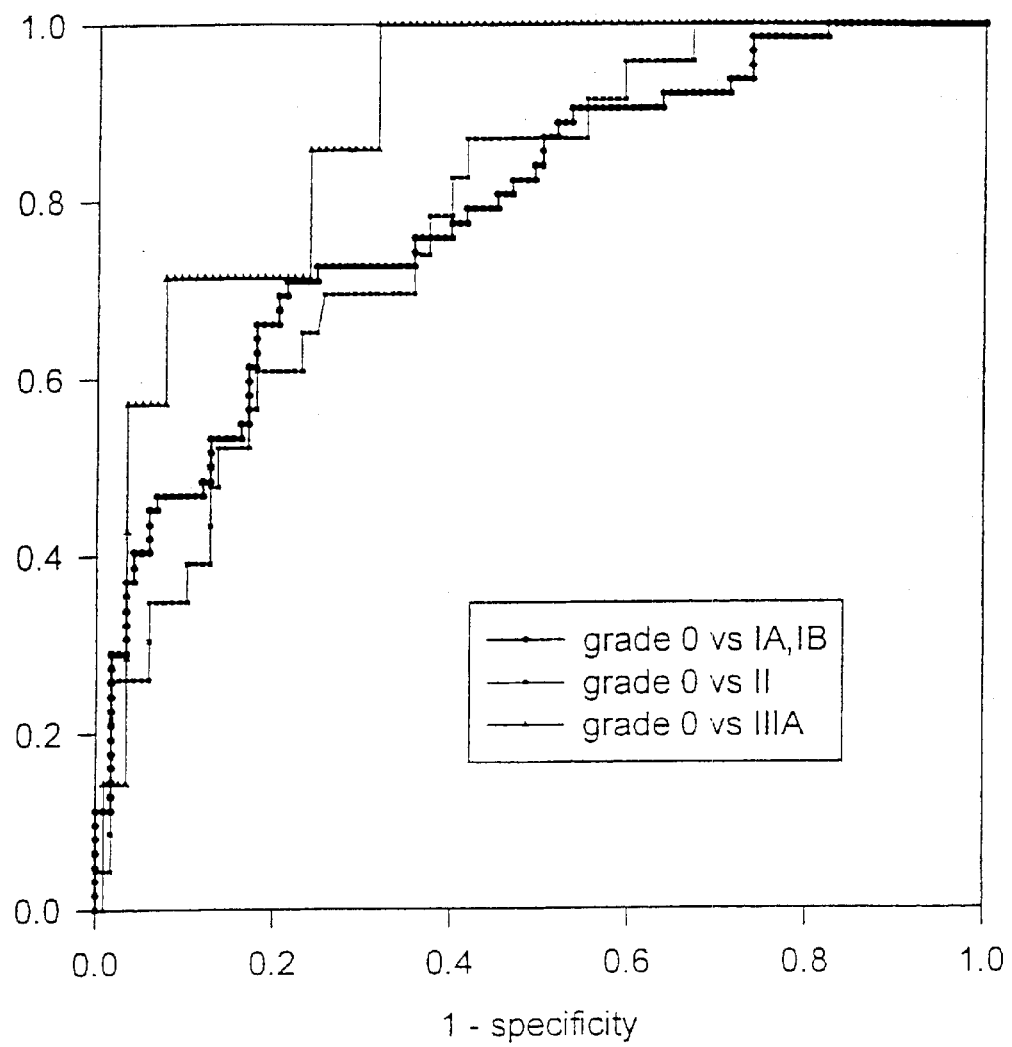

FIG. 39: Sensitivity and specificity of the breath test for heart transplant rejection: These receiver operating characteristic (ROC) curves were generated from the probabilities of rejection shown in FIG. 38. The test was most sensitive and specific for Grade IIIa rejection, and less so for Grades Ia, Ib, and II.

Figure 40:
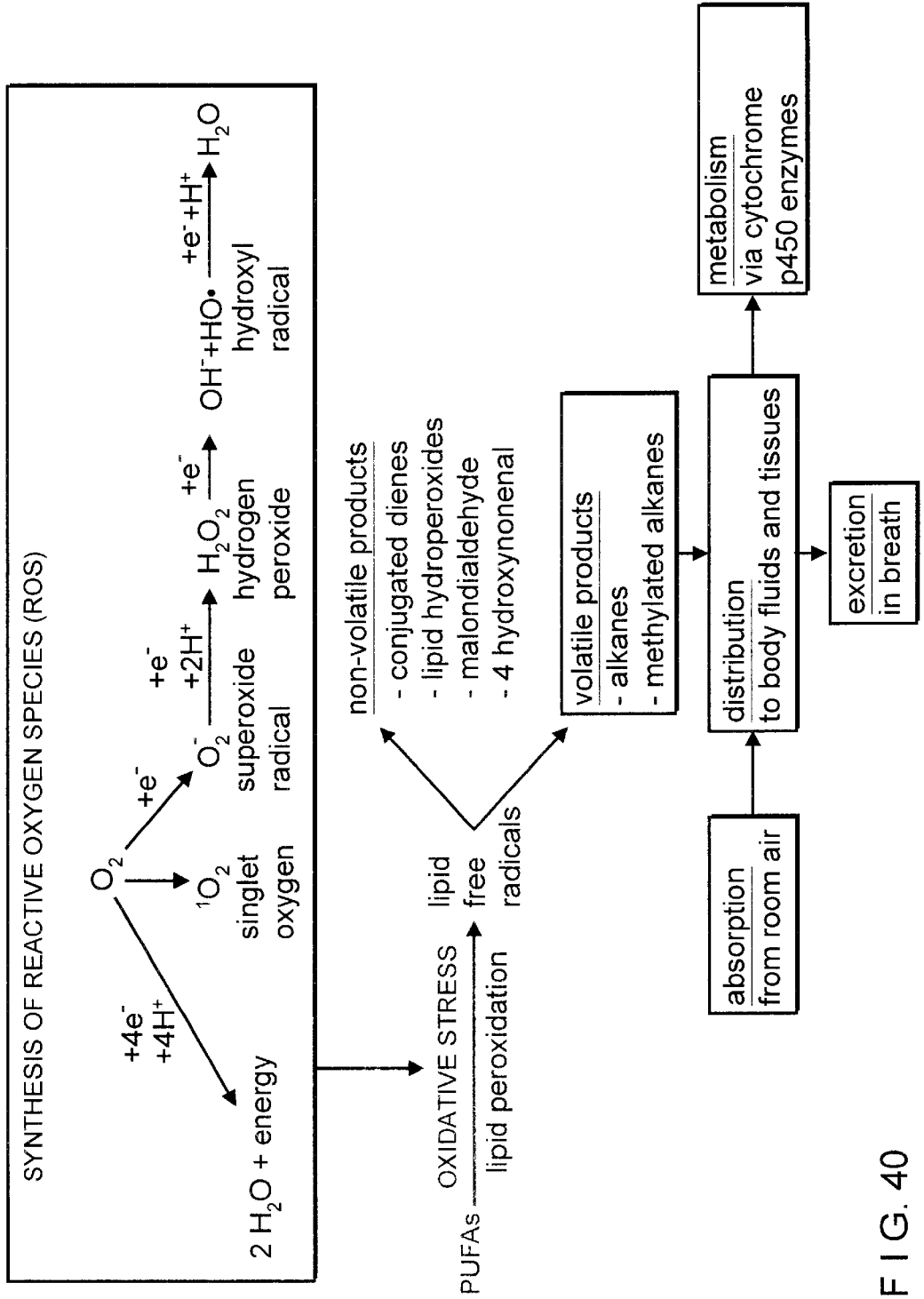

FIG. 40: Origin of oxidative stress and the generation of metabolic markers. ROS are synthesized in the mitochondria; electron leak into the cytoplasm generates oxidative stress, a constant barrage of damage to DNA and proteins and polyunsaturated fatty acids (PUFAs). This diagram illustrates the effect of oxidative stress on PUFAS, generating alkanes and methylated alkanes which are either metabolized or excreted in the breath.

Figures 41A, 41B:
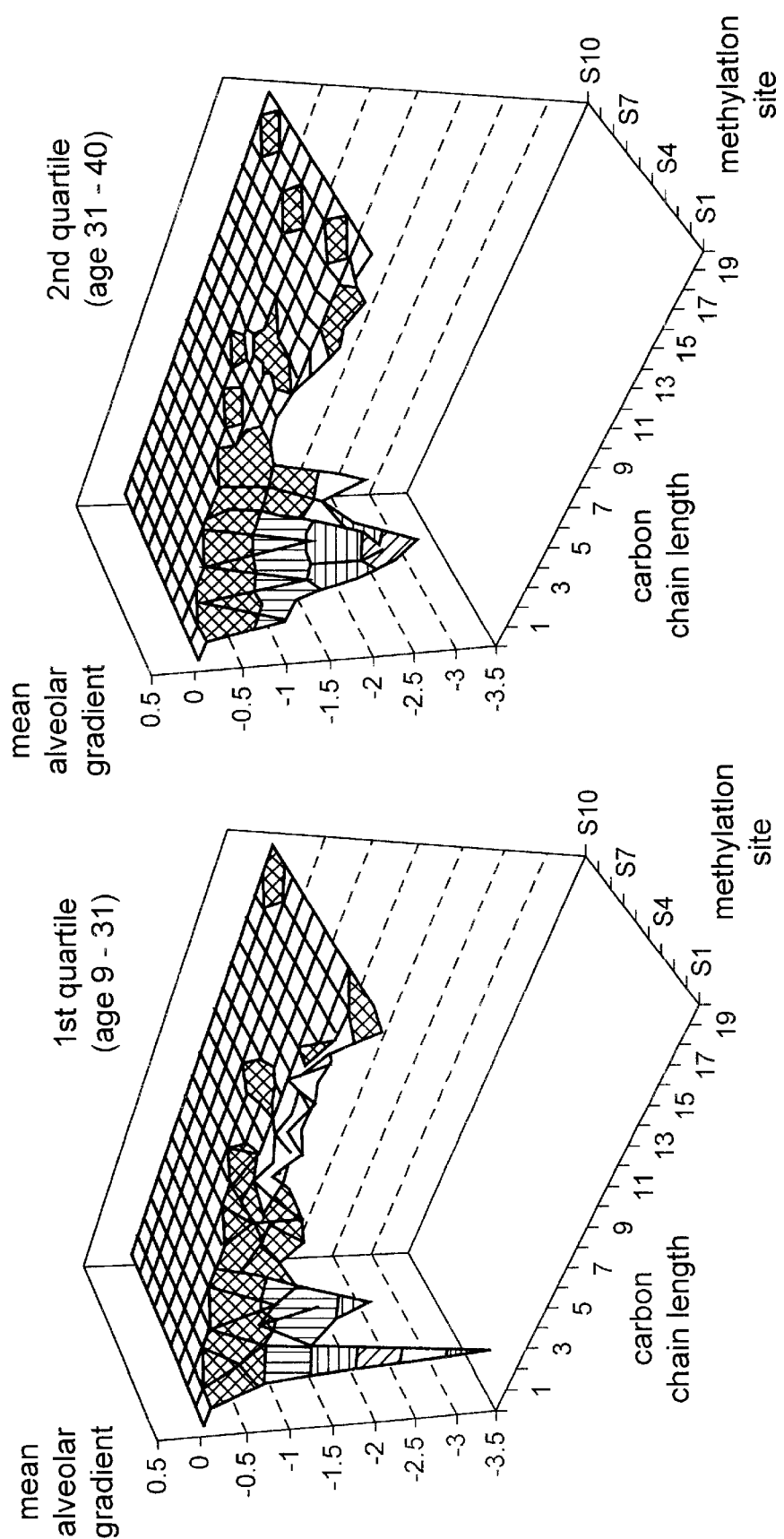
Figures 41C, 41D:
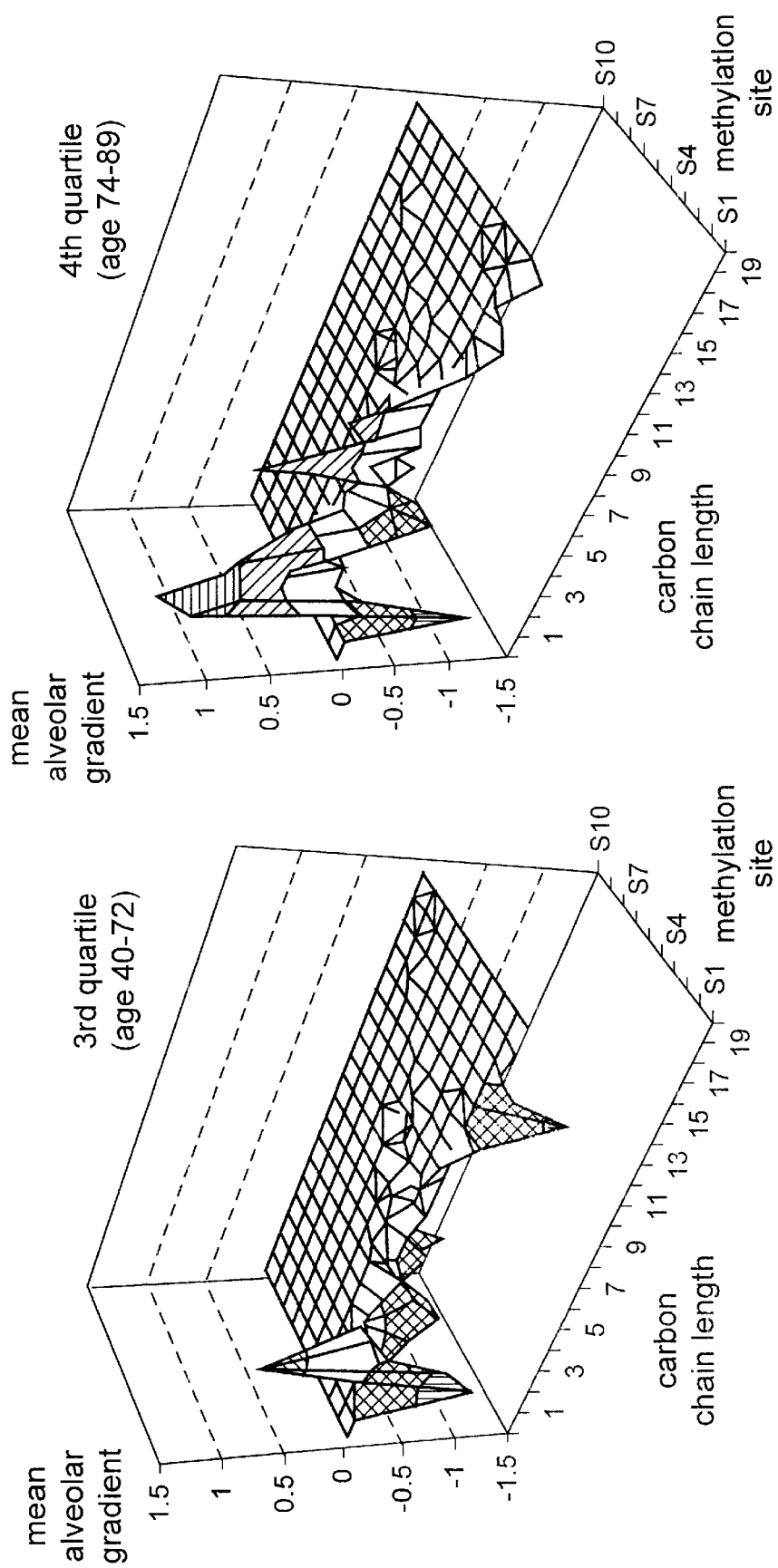

FIG. 41: Breath methylated alkane contours (BMACs) in normals. The mean BMACs are shown for 102 normal humans, separated by age quartile. The compounds shown are straight chain n-alkanes methylated at one site. This figure includes n-alkanes, showing them as methylated at C1. For example an alkane with carbon chain length=4 (butane) becomes the C5 alkane pentane when methylated at C1. The alveolar gradient is the concentration in breath minus the concentration in room air, and varies with the rate of synthesis minus the rate of clearance. A progressive change from negative to positive alveolar gradients of several methylated alkanes occurred with age, consistent with increasing oxidative stress with age. Statistically significant differences between younger and older subjects are shown in Table 1.

Figure 42C:
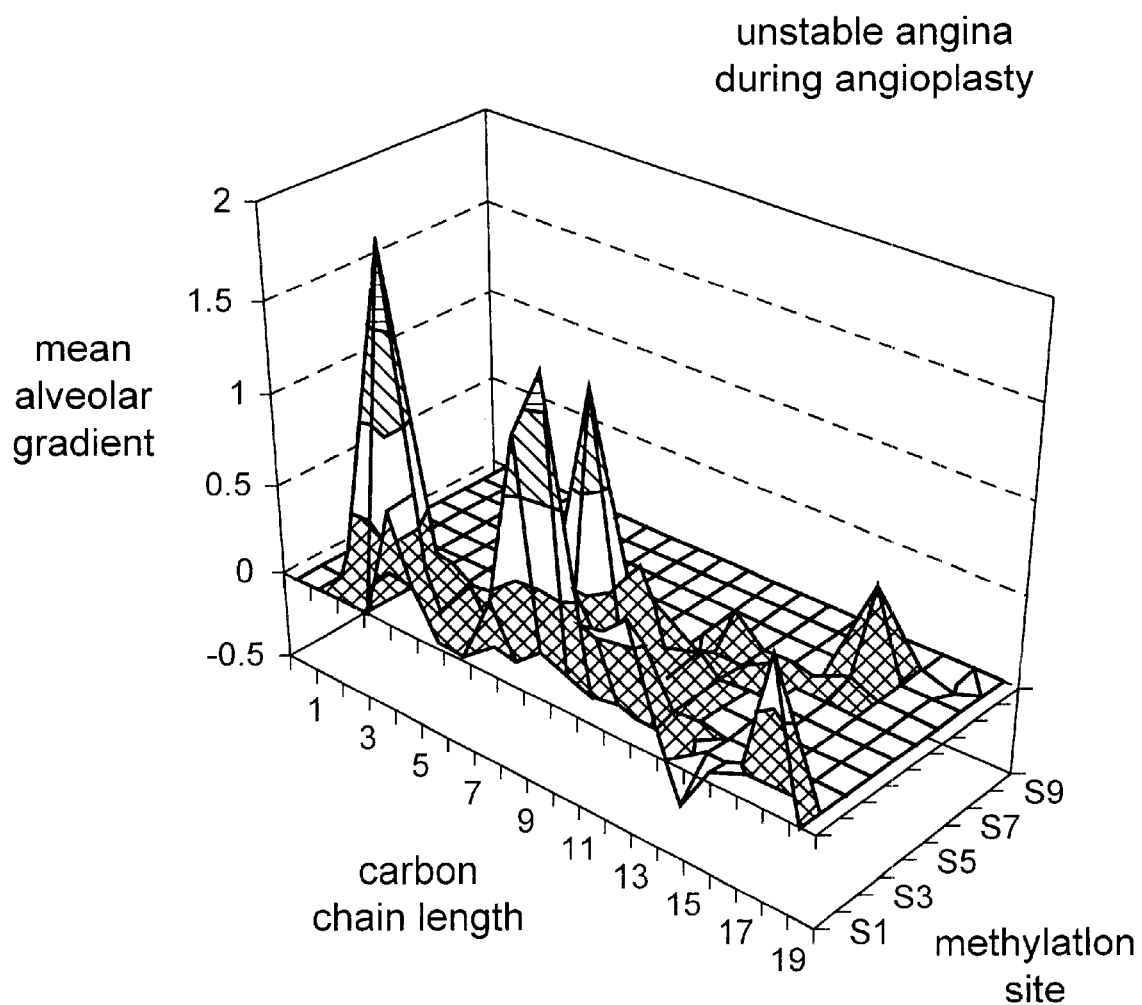

FIG. 42: Effect of unstable angina and coronary angioplasty on BMAC. Mean BMACs are shown in age-matched normal controls, 30 patients with unstable angioplasty, and the same patients during coronary angioplasty.

Figure 43:
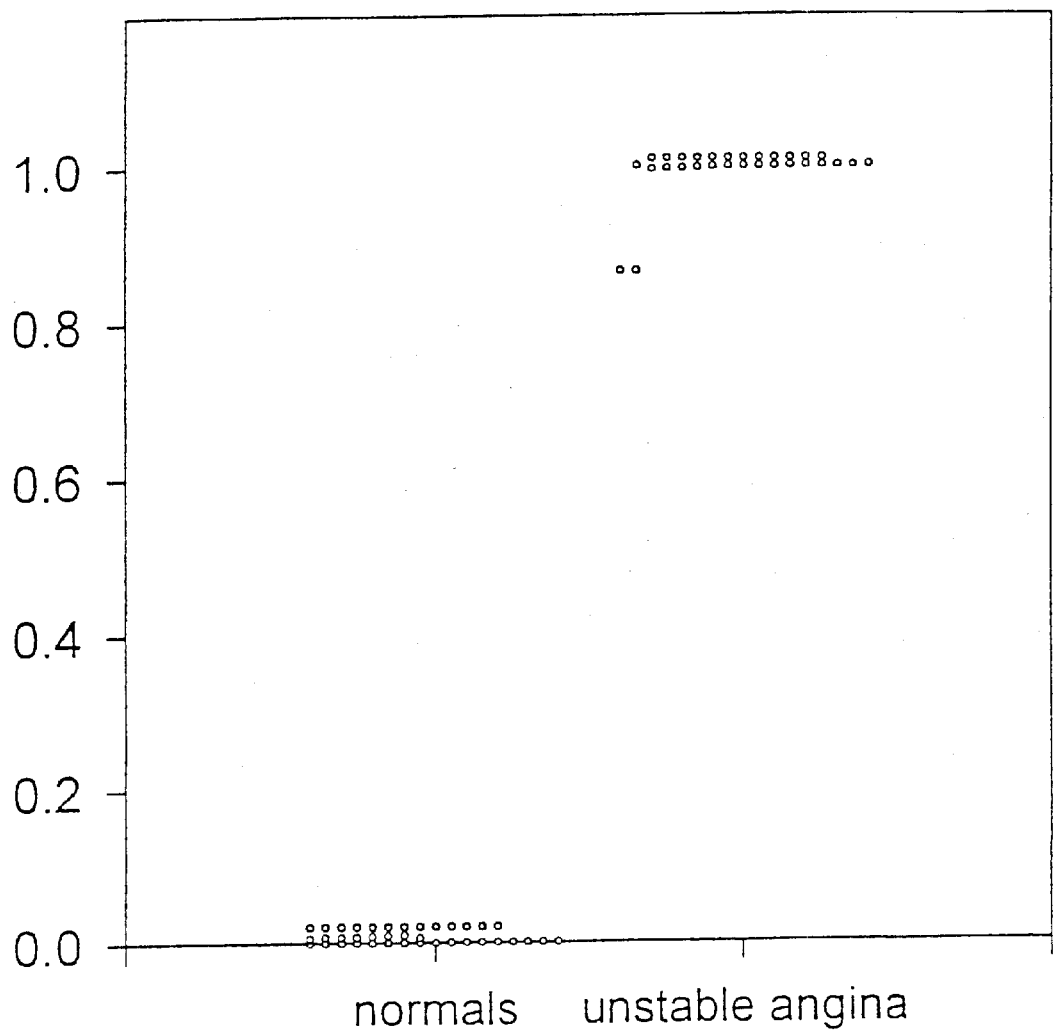

FIG. 43: Probability of unstable angina. Logistic regression was employed to identify the possibility of unstable angina based upon the BMAC alone, in patients with unstable angina and age-matched normal controls. There was no overlap between the two groups.

Figures 44A, 44B:
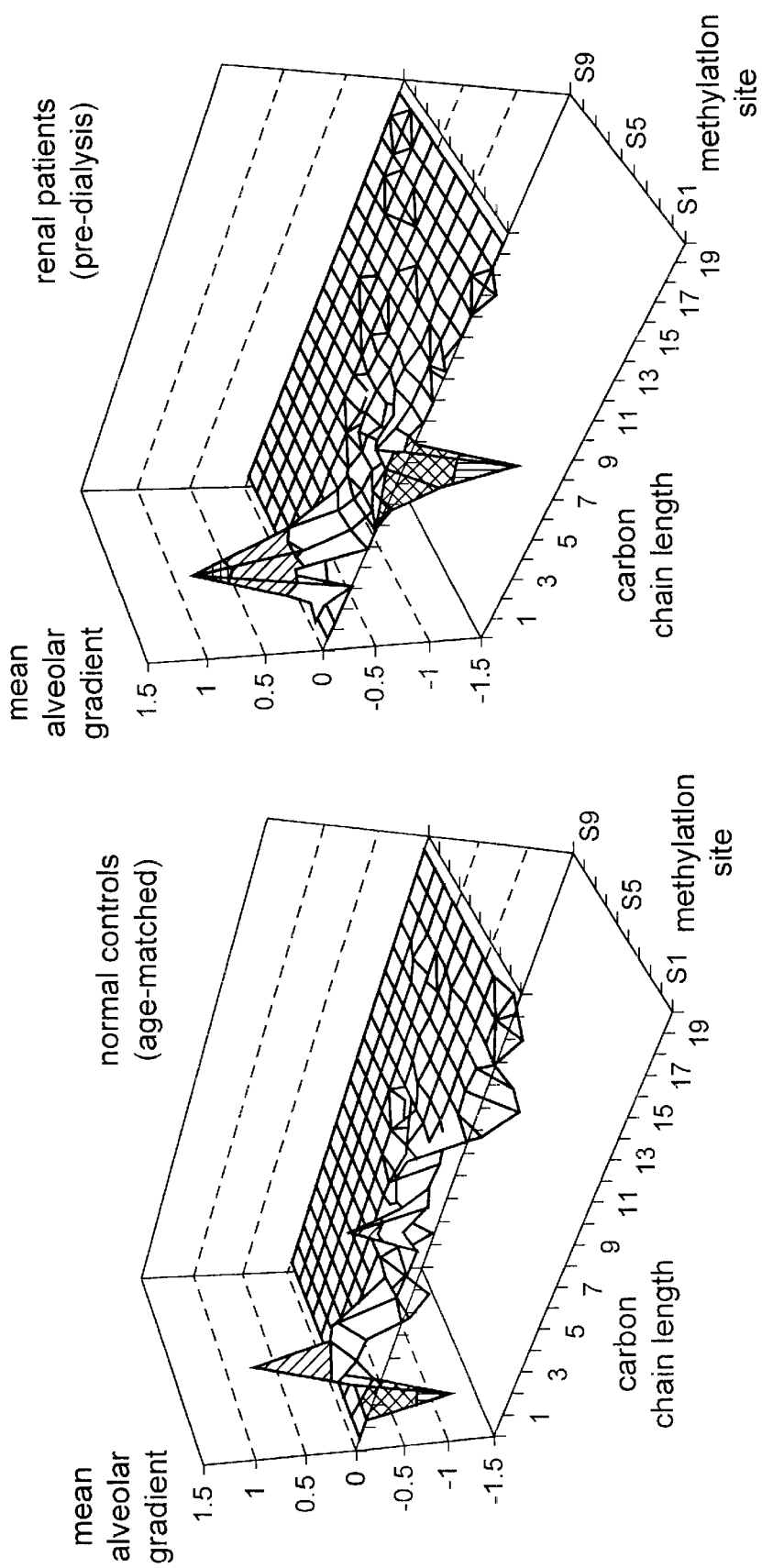
Figure 44C:
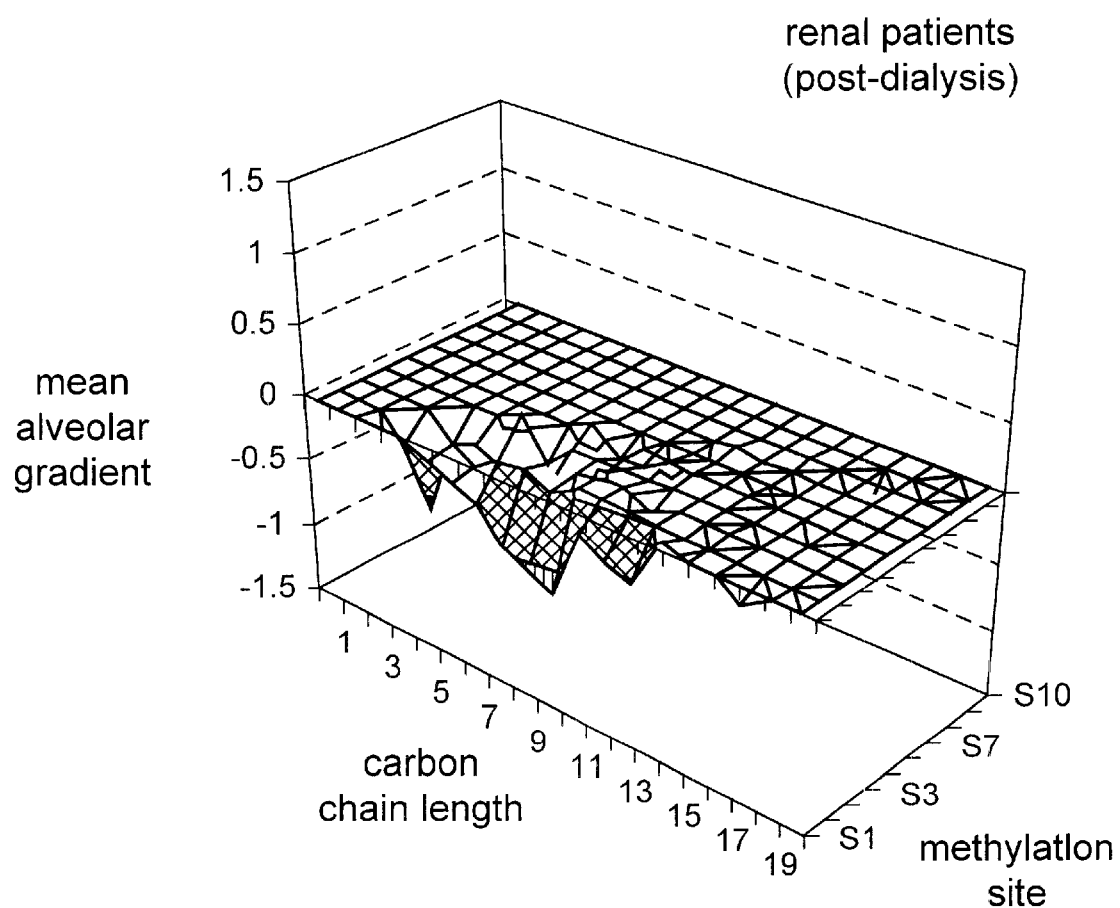

FIG. 44: Mean BMACs in age-matched normals and ESRD patients before and after hemodialysis FIG. 45: Sensitivity and specificity of the BMAC for ESRD. The mean BMACs in age-matched normals and ESRD patients before hemodialysis were compared by logistic regression analysis. The ROC curve demonstrates that the BMAC provided a highly sensitive and specific marker of ESRD.

Figures 46A, 46B:
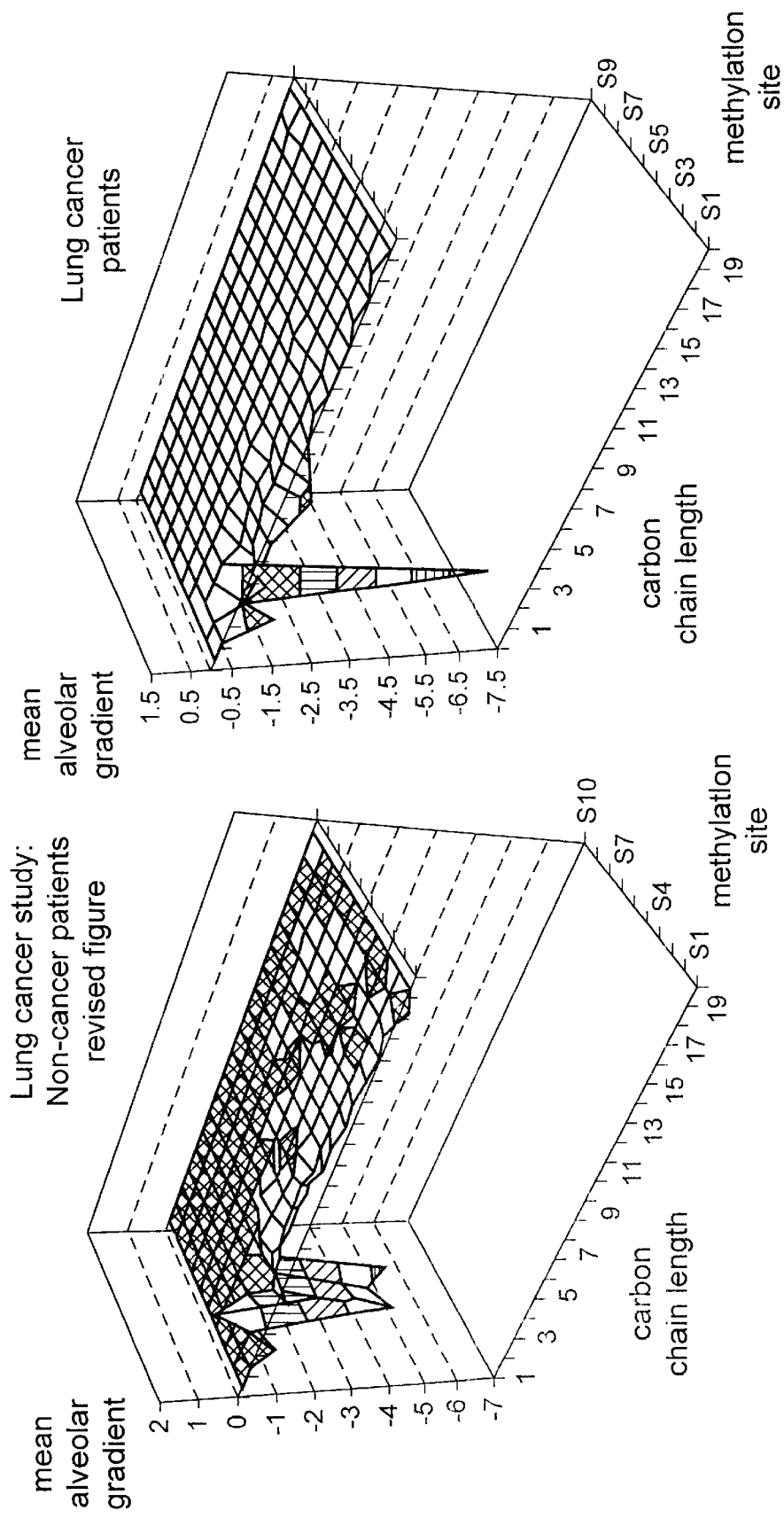

FIG. 46: Mean BMACs in patients with and without lung cancer.

Figures 47A, 47B:
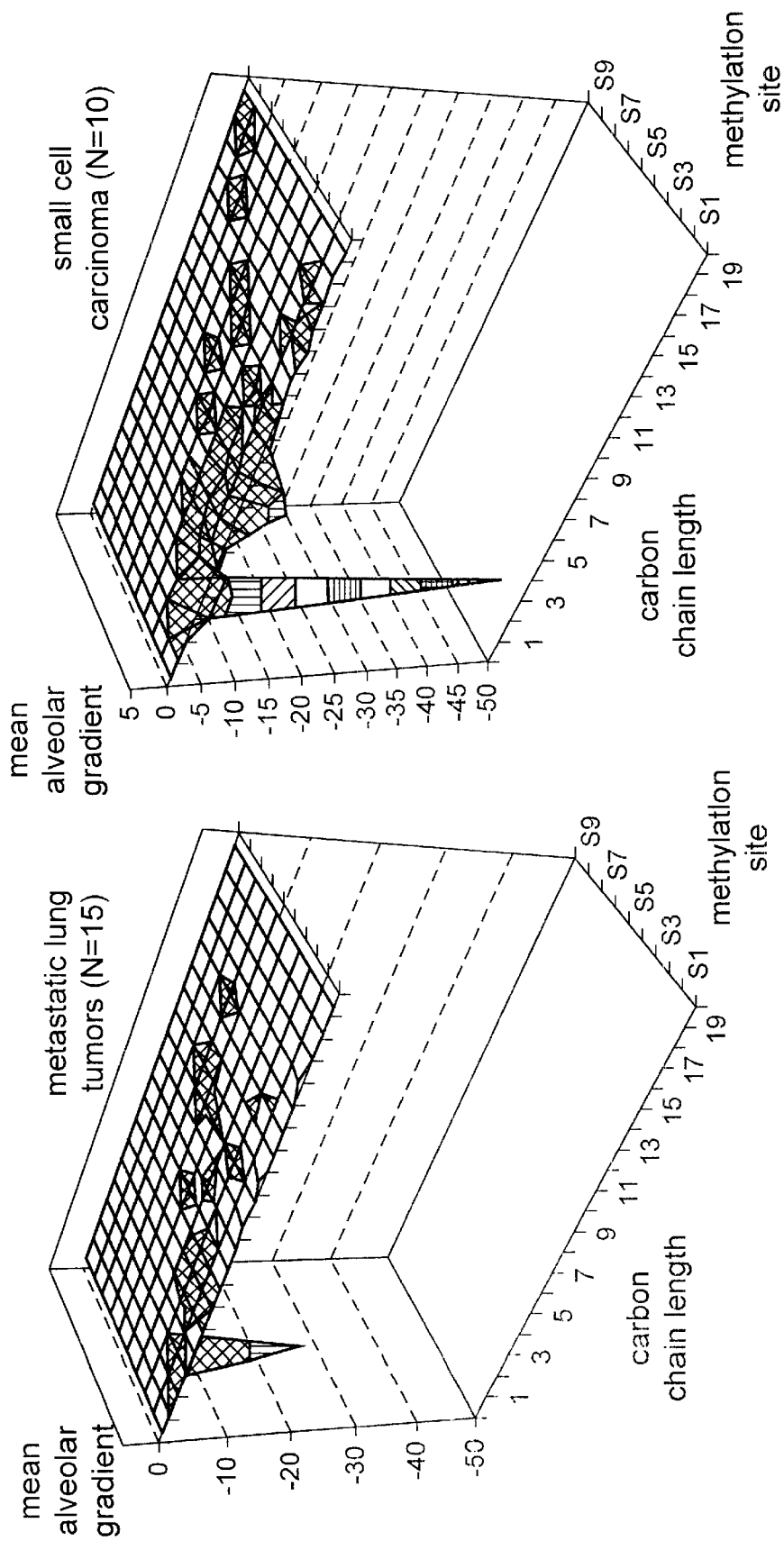
Figure 47C:
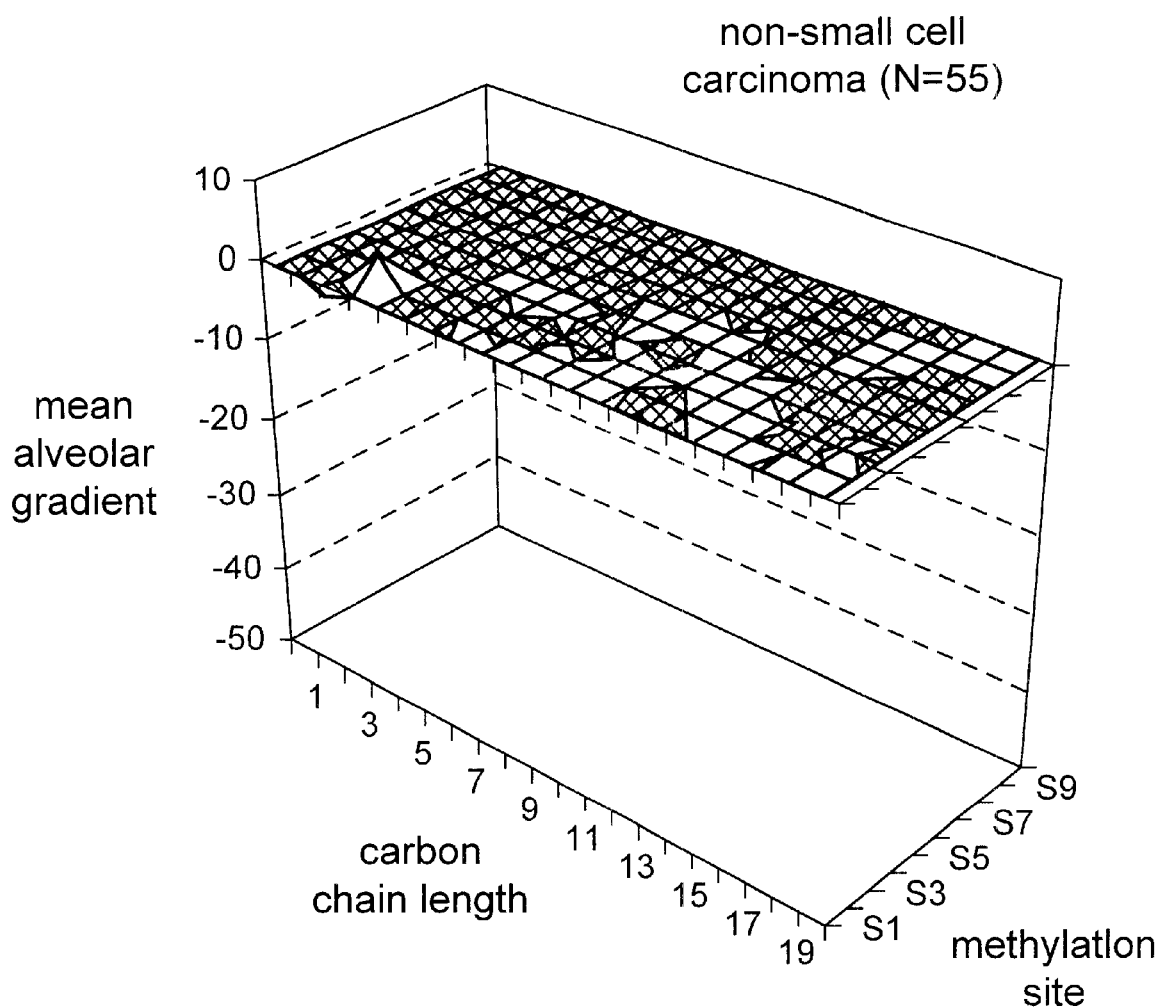

FIG. 47: Mean BMAcs in patients with metastatic lung cancer, small cell carcinoma and non-small cell carcinoma.

Figure 48:
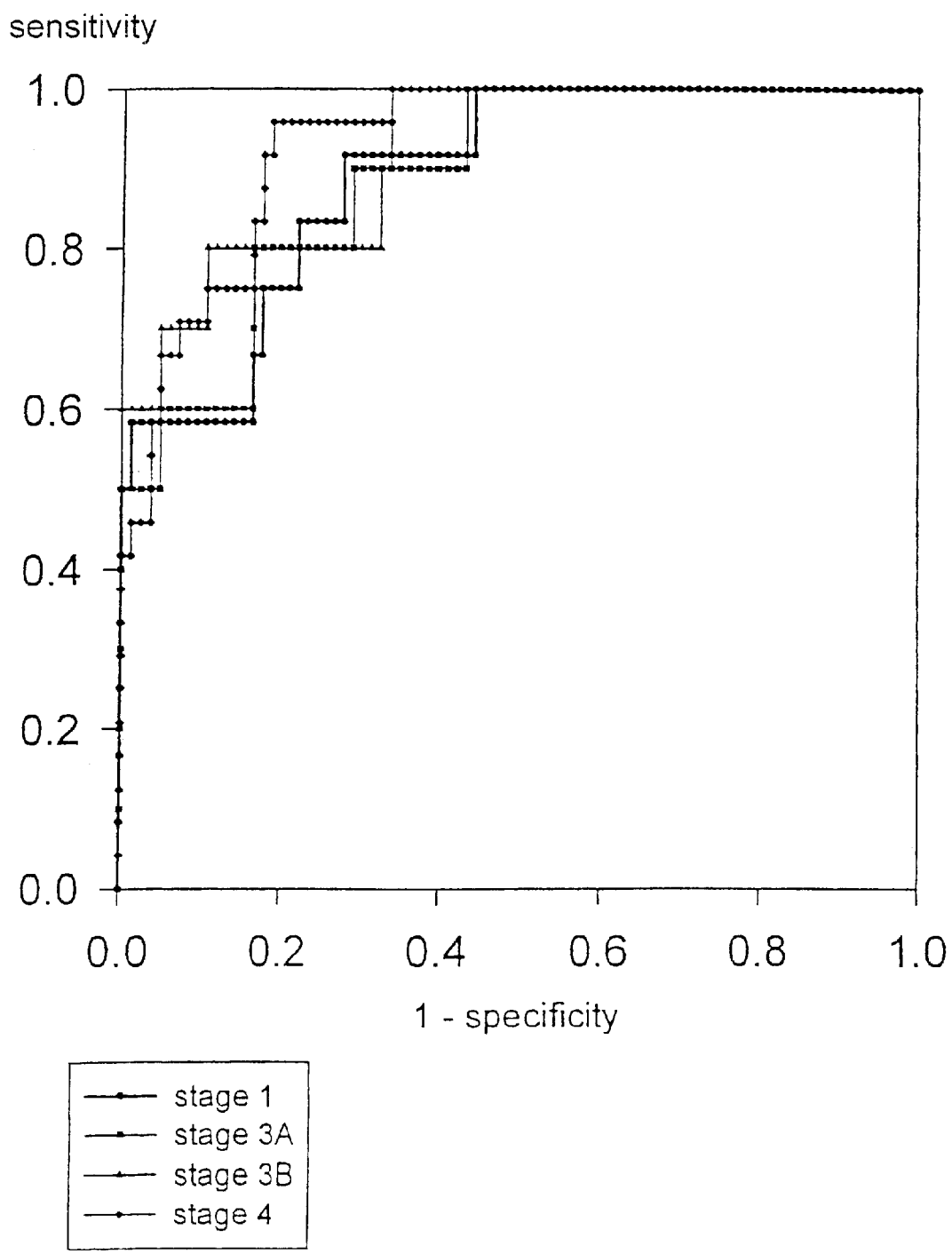

FIG. 48: Sensitivity and specificity of the breath test according to TNM staging of cancer FIG. 49: Sensitivity and specificity of the breath test according to the histological type of cancer.

Figure 50:
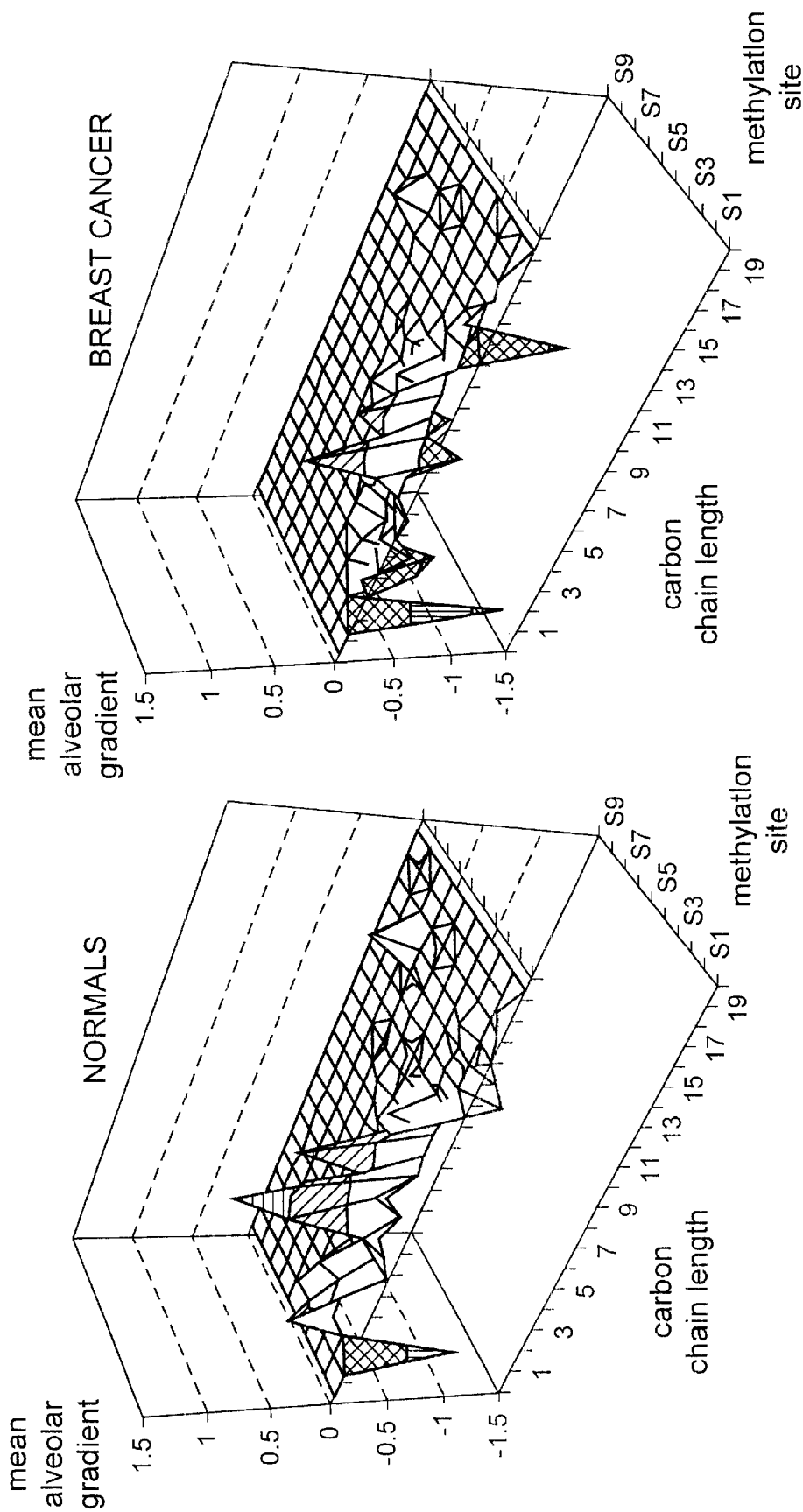

FIG. 50: Mean BMACs in women with and without breast cancer.

Figure 51:
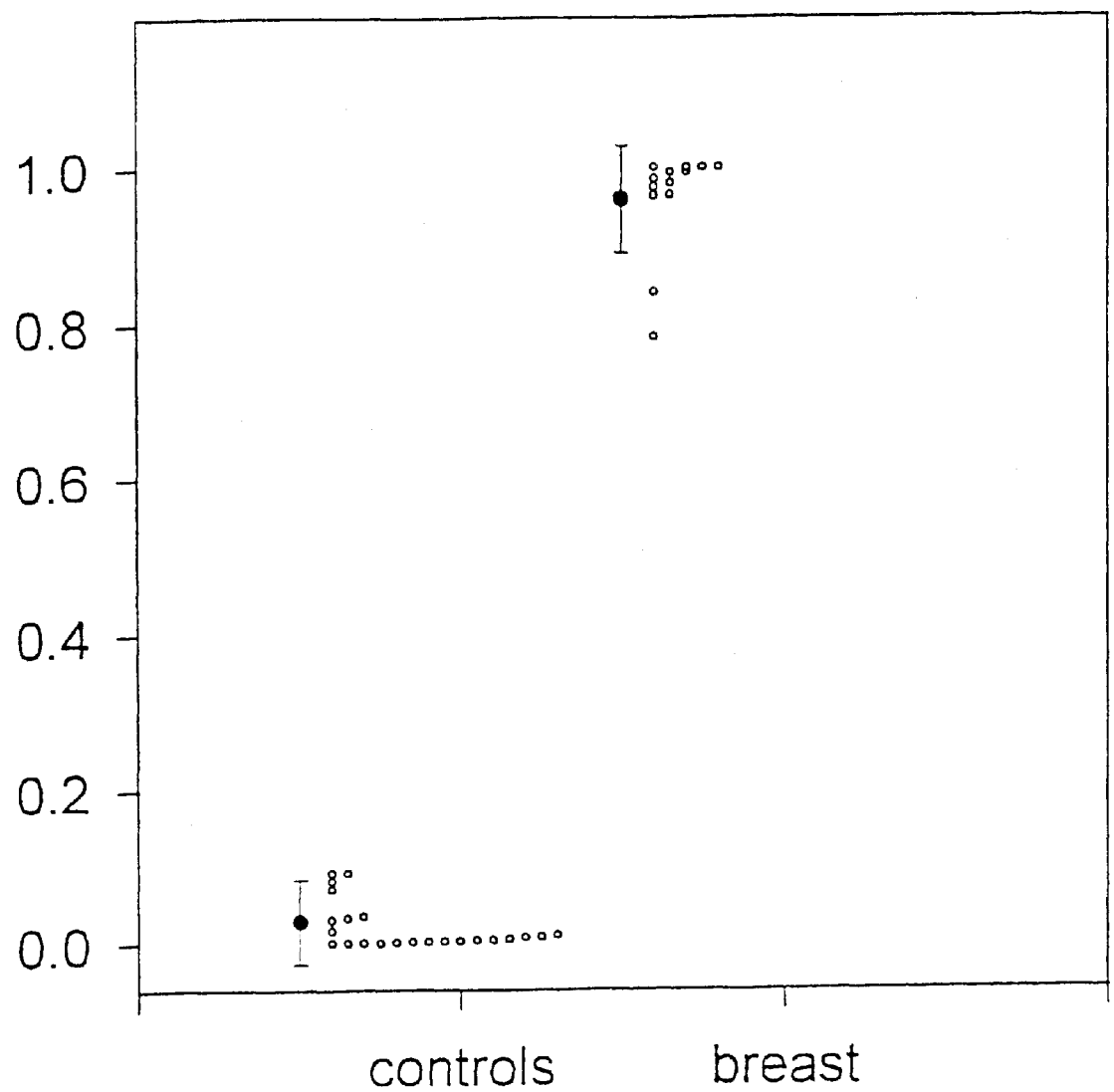

FIG. 51: Probability of breast cancer based upon BMAC.

DETAILED DESCRIPTION OF THE PREFERRED EMBODIMENTS OF THE INVENTION

As described above, the methods of collecting and analyzing alveolar breath are well-known to those skilled in the art. The present invention comprises interpretation of the analytical results and profiling them to determine the presence or absence of disease in a human.

The term "alkane" or "n-alkane" as used herein means a hydrocarbon of the formula

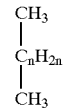

wherein n is an integer of 1 to 18.

The following examples demonstrate the manner and process for carrying out the invention and set forth the best mode contemplated by the inventor for practice of the invention.

The Apparatus for Breath VOC Collection and Analysis

The breath collection apparatus (BCA): This device has been described (Phillips, supra.). In summary, the BCA is a portable, microprocessor-controlled device with a heated breath reservoir which prevents condensation of water. Alveolar breath is pumped from the breath reservoir through a sorbent tube which captures the VOCs on activated carbon. In this study, modified sorbent tubes were employed containing 200 mg Carbotrap C (20/40 mesh) and 200 mg Carbopack B (60/80 mesh) (Supelco, Inc, Bellefonte, Pa.). The volume of the breath sample can be varied via a panel-mounted timer and flow meter, and the geometry of the system ensures that the sample comprises alveolar breath virtually uncontaminated by dead-space air.

Collection of a breath sample: Subjects breathed into the BCA through a disposable mouthpiece. The BCA presented minimal resistance to expiration because the wide-bore breath reservoir (1.0 inch dia) was open to the air at its far end. Samples could be collected even from elderly or bedridden patients without causing discomfort. The collection period was 2.0 min at 0.5 l/min, and two samples were collected: one of breath, and one of background room air.

Assay instrumentation and procedure: VOCs were desorbed from the sorbent tubes and concentrated in an automated thermal desorber (ATD 400, Perkin Elmer, Norwalk, Conn.), separated in a gas chromatoraph, and identified and quantitated in a mass spectrometer (HP6890 and mass selective detector 5973, Hewlett Packard, Palo Alto, Calif.). Sorbent tubes were loaded onto a carousel (capacity 50), checked for leaks, then purged with helium for 1.0 min to remove water vapor and air. An internal standard (0.25 ml 2 ppm 1-bromo-4-fluorobenzene, Supelco Inc, Bellefonte, Pa.) was added via the ATD 400 standard injection accessory. The sample was desorbed at 300° C. onto a 0° C. cold trap (low flow ATD 400 air monitoring trap) for 4 min (helium flow 50 ml/min, outsplit flow 2.0 ml/min). The cold trap was then heated rapidly to 300° C. and the desorbed sample was flushed through a fused silica transfer line (0.25 m.m. ID, 200° C. helium flow 1.25 ml/min) to the chromatography column (SPB-5 capillary column, 30 m×0.25 m.m.×0.25 um film thickness, Supelco Inc, Bellefonte, Pa.). Column temperatures were ramped as follows: 0° C. for 8 min, 4° C./min to 138° C., 0.10 min hold, 10° C./min to 210° C. 0.10 min hold, and 30 C°/min to 300° C., 0.25 min hold.

Data management: Data from each chromatographic peak, comprising retention time, chemical identity (as identified by Wiley 138 library), area under curve (AUC), and quality of fit, were automatically downloaded into a spreadsheet (Excel 4.0, Microsoft, Redmond, Wash.) and consolidated in a relational database (Paradox, Borland, Scotts Valley, Calif.). The alveolar gradient of each VOC was calculated as:

$$(AUC_{VOC\ in\ breath} - AUC_{VOC\ in\ air})/AUC_{internal\ standard}$$

The Kinetic Determinants of the Alveolar Gradient

FIG. 3 demonstrates the pathways which VOCs follow through different compartments of the body. Equilibration is rapid in the pulmonary alveoli, so that the concentration of a VOC in alveolar breath is determined by its concentration in pulmonary arterial blood, while the concentration of a VOC in room air determines its concentration in pulmonary venous blood. The body pool of VOCs is derived from two sources: pulmonary input (from room air) and extrapulmonary input (principally from synthesis in the body, although exogenous sources of VOCs such as foods, drugs, and percutaneous absorption may also contribute). VOCs leave the body pool by two routes: either by pulmonary output (in alveolar breath) or by extrapulmonary output (clearance by metabolism and/or excretion). The kinetics of a VOC in the body may also be modeled by the flow of water into and out of a common pool (FIG. 4).

Kinetic analysis demonstrates that the alveolar gradient of a VOC varies with the rate of synthesis of the VOC minus its rate of clearance from the body (see Appendix 1: Kinetic analysis of the determinants of the alveolar gradient). The polarity of the alveolar gradient indicates which of the two processes is predominant. If the alveolar gradient is positive, the rate of synthesis is greater than the rate of clearance; conversely, if the alveolar gradient is negative, then the rate of clearance is greater than the rate of synthesis. As an example, the mean alveolar gradient of the long-chain n-alkane tetradecane was positive, demonstrating that in vivo synthesis predominated over clearance. Conversely, the mean alveolar gradient of methylbenzene was negative, demonstrating that clearance was greater than in vivo synthesis. This was consistent with ingestion of methylbenzene as a pollutant of room air which was then cleared from the body by metabolism and excretion.

The Composition of Breath VOCs in Normal Humans

Despite numerous studies of pentane and several other breath VOCs, the range of composition of VOCs in normal human breath has not been well defined. Early studies reported substantial quantitative and qualitative differences amongst small groups of normal humans: concentrations of breath VOCs varied widely, and a number of VOCs were detectable in the breath of some subjects but not in others (Conkle J P, Camp B J and Welch B E: Trace composition of human respiratory gas, Arch Environ Health 1975; 30:290–295);

Barkley J. Bunch J. Bursey J T et al: Gas chromatography mass spectroscopy computer analysis of volatile halogenated hydrocarbons in man and his environment—a multimedia environmental study, Biomedical Mass Spectrometry 1980; 7(4): 139)–147). The composition of breath VOCs was investigated in normal humans (Example 1).

Human subjects: 50 normal human subjects were studied employing the method described above. They comprised 27 males (mean age 38.8 yr, SD=12.8) and 23 females (mean age 38.65 yr, SD=11.4).

Inter-individual variation in number of VOCs: The number of VOCs detected in each breath sample ranged from 157 to 241 (mean=204.2, SD=19.8, CV=9.7%.) (FIG. 1). 3481 different VOCs were observed at least once, 1753 with positive alveolar gradients and 1728 with negative alveolar gradients, but the majority of these were observed in only one subject. Only 27 VOCs were observed in all subjects (FIG. 2).

Inter-individual variation in frequency and abundance of VOCs: VOCs were ranked by the frequency with which they were observed in different subjects (Table 1, below) and by their relative abundance in the breath (Table 2, below).

Discussion: More than 200 different VOCs were observed in most breath samples, and more than 3000 different VOCs were observed at least once. These numbers probably represent an underestimate of the total number of VOCs in normal human breath, since the assay was limited to C4 to C20 VOCs within the trapping range of the sorbent traps. The majority of these VOCs were observed only once. The number of breath VOCs observed in more than one subject fell rapidly as the size of the group increased, and only a comparatively small number of commonly occurring VOCs were observed consistently in the majority of the population.

Several of the commonly occurring VOCs were derived from metabolic pathways that have been previously reported e.g. isoprene from the mevalonic acid pathway of cholesterol synthesis (Stone B G, Besse T J, Duane W C, Evans C D and DeMasster E G: Effect of regulating cholesterol biosynthesis on breath isoprene excretion in men; Lipids 1993;28:705–708, acetone from glucose metabolism, Stewart R D and Boettner E A: Expired-air acetone in diabetes mellitus; New England Journal of Medicine, 1964;270:1035–1038), and alkanes from OFR-mediated lipid peroxidation of fatty acids. However, the source of commonly occurring VOCs such as napthalene and 1-methylnapthalene is not yet known. They may be degradation products of steroids, but further studies are required to determine their origin.

The actual concentration of each VOC in molar or mass units was not determined because this would have required the construction of more than 3000 different standard curves, a very considerable undertaking. Instead, we determined the ratio of the area under curve (AUC) of the chromatographic peak of each VOC to the AUC of the internal standard. This value is a correlate of molar concentration, and it was used to estimate the abundance of each VOC in breath and air. The relative abundance of each VOC was then ranked by its alveolar gradient i.e. abundance in breath minus abundance in room air.

The results of this study (Example 1) accorded with previous reports that normal humans differ widely from one another in the composition of their breath VOCS, both qualitatively and quantitatively. However, it also demonstrated two points of similarity between individuals which have not been previously reported: First, the total number of breath VOCs in each individual did not vary widely within a fairly narrow range. Second, despite the large total number of different VOCs observed, there was a comparatively small "common core" of breath VOCs which was present in all subjects, and which was probably produced by metabolic processes common to most humans.

The Breath Alkane Profile in Normal Humans

This Example 2 investigated the composition of alveolar breath in normal humans in order to determine the detectable spectrum of alkanes and alkane derivatives with different carbon chain lengths, the variation in the alveolar gradients of these VOCs, and the frequency of their occurrence in breath and in air.

Materials and Methods

Breath collection apparatus (BCA) and assay: The method has been described in Example 1, supra.

Human subjects: Breath samples were collected from 50 normal volunteers comprising 27 males (mean age 38.8 yr, SD=12.8) and 23 females (mean age 38.65 yr, SD=11.4). All had fasted from the previous midnight and samples were collected between 7.00 am and 12.00 noon.

Analysis of data: The abundance of a VOC in breath or air was determined from the ratio $AUC_{voc}/AUC_{internal\ standard}$ where AUC was the area under curve of the VOC peak on the chromatogram. The alveolar gradient was determined as:

$$(AUC_{VOC\ in\ breath} - AUC_{VOC\ in\ air})/AUC_{internal\ standard}.$$

Results

The mean abundance of each VOC in breath and air, and its alveolar gradient are shown as these values varied with carbon chain length in alkanes (FIGS. 6–7), alkyl alcohols (FIGS. 8–9) and 2-methyl alkanes (FIGS. 10–11). The frequency with which each VOC was observed in samples of breath and air is also shown as a function of carbon chain length. Multiple t-tests revealed no significant differences between the alveolar gradients of alkanes, alkyl alcohols and 2-methyl alkanes in males and females.

Discussion n-alkanes ranging from C2 to C10 were detected in room air and in normal human breath. The absence of shorter or longer chain alkanes was probably due to the limited trapping range of the sorbent traps employed in this study. A distinctive and continuous profile of alveolar gradients was observed in alkanes of different chain lengths: mean values were negative from C4 to C11, and positive from C13 to C20 (FIGS. 6–7). These findings confirmed an earlier observation that the mean alveolar gradient of breath pentane was negative in normal humans (Phillips M. Sabas M. & Greenberg, J. supra.). The significance of this alveolar gradient profile may be inferred from analysis of VOC kinetics in the body:

$$\text{alveolar gradient} = C_{alveolar\ breath} - C_{room\ air} = (R_{synthesis} - R_{clearance})/RMV$$

where R=rate of movement of VOC (mol/min), C=concentration of VOC (mol/l), and RMV=respiratory minute volume (l/min) (Appendix 1). Hence, these findings are consistent with the conclusion that in normal humans, the rate of clearance of alkanes was greater than the rate of synthesis for C4 to C12 alkanes, while the rate of synthesis was greater than the rate of clearance for C12 to C20 alkanes. The rate of synthesis of an alkane is principally determined by OFR-mediated lipid peroxidation of PUFAs, while the rate of clearance is most likely determined by degradation via the cytochrome P450 system;

(Crosbie S J, Blain P G and Williams F M: Metabolism of n-hexane by rat liver and extrahepatic tissues and the effect of cytochrome P-450 inducers (Hum Exp Toxicol 1997; 16(3):131–137;

Scheller U, Zimmer T. Kargel E and Schunck W H: Characterization of the n-alkane and fatty acid hydroxylating cytochrome P450 forms 52A3 and 52A4, Arch Biochem Biophys 1996;328(2):245–54).

The frequency distribution of alkanes in breath and air (FIGS. 6–7) demonstrates that heptane was observed in all samples of room air but in 0% of alveolar breath samples. The most likely explanation is that inspired heptane was cleared from the body with high efficiency by metabolism and excretion, thereby reducing its concentration to undetectable levels in the pulmonary artery and the alveolar breath of 90% of the normal subjects. C5, C6, and C9 through C15 alkanes were present in nearly all samples of room air. These alkanes were probably derived from the breath of other humans. Further studies will be required to determine if this is a common characteristic of room air at other geographic sites. However, experience in our laboratory and elsewhere indicates that pentane can commonly be detected as a contaminant of room air when a sufficiently sensitive assay is employed (Cailleux A and Allain P: Is pentane a normal constituent of human breath? Free Radic Res Commun 1993;18 (6):323–7;

Phillips M. Sabas M. and Greenberg J: Alveolar gradient of pentane in normal human breath, Free Radical Research Communications 1994; 20(5):333–337).

Alkyl alcohols ranging from C2 to C18 were also detected in room air and alveolar breath, though they were less abundant than alkanes and were not observed as frequently (FIGS. 8–9). Ethanol was more abundant than any other alkyl alcohol, and its alveolar gradient was positive. Hence, endogenous synthesis of ethanol predominated over clearance. This finding is consistent with previous observations of endogenous ethanol in breath, where it may be a product of metabolism or bacterial fermentation in the intestine;

(Phillips M and Greenberg J: Detection of endogenous ethanol and other compounds in the breath by gas chromatography with on-column concentration of sample, Analytical Biochemistry, 1987;163:165–169). 2-methyl alkanes ranging from C3 to C20 were also observed in room air and breath (FIGS. 10–11). The origin of these VOCs is unclear; they may be derived from methylation of alkanes.

In conclusion, these findings demonstrate that normal human breath contains a wider spectrum of alkanes, alkyl alcohols and 2-methyl alkanes than has previously been reported. Profiles of the alveolar gradients indicate that the rate of clearance (mainly by cytochrome P450) exceeded the rate of synthesis (by OFR-mediated lipid peroxidation of PUFAs) for C4 to C12 alkanes, and the rate of synthesis exceeded the rate of clearance for C13 to C20 alkanes. These findings extend the spectrum of known breath markers of oxidative stress in humans.

The Breath Alkane Profile in Breast Cancer

Breath samples were collected from a group of women undergoing screening mammography. Breath and air samples were collected and analyzed in the manner described above. This non-random sample was intentionally skewed to include a relatively large number of women with breast cancer. 35 women were studied on the same day mammography was performed, with normal mammograms and 10 in whom breast cancer was detected for the first time. All diagnoses of breast cancer were subsequently confirmed by tissue biopsy. Mean alkane profiles were determined for alveolar breath (FIG. 12), room air (FIG. 13) and alveolar gradient (FIG. 14). All three curves were visibly different in women with and without breast cancer, and differences in a number of alkanes were statistically significant on t-testing. An unexpected and apparently paradoxical finding was the marked difference in composition of room air in the two groups. However, VOCs expired in the breath may modify the composition of room air, an observation which may be confirmed by the everyday experience of occupying the same room as a person with severe halitosis. The alveolar gradient curves (FIG. 14) were analyzed by logistic regression, and the posterior probability of breast cancer based upon the alkane profile alone was determined for each woman (FIG. 15). This demonstrated a clear separation between the two groups with no false positive or false negative results.

Interpretation: The breath alkane profile of alveolar gradients was displaced downwards in women with breast cancer. This is consistent with clearance predominating over synthesis. However, the increased amount of alkanes in room air was evidence for increased synthesis of alkanes. The most likely explanation is that both synthesis and clearance of alkanes are increased in women with breast cancer, but clearance is increased to a greater extent. Displacement of the breath alkane profile was sufficient to distinguish between women with and without breast cancer with 100% sensitivity and specificity. The breath alkane profile appears to provide a rational new biomarker of breast cancer. Breath testing might provide a clinically useful new method for the early detection of breast cancer. It could be employed in mass screening because it is simpler, safer, less painful and less expensive than screening mammography.

The Breath Alkane Profile in Ischemic Heart Disease

Part A

Breath tests were performed in eight patients with unstable angina documented by coronary angiography. Their mean breath alkane profile was displaced upwards from the mean profile observed in the normal controls, consistent with an increased predominance of synthesis over clearance of alkanes. The breath test was repeated in these patients during coronary angioplasty while the balloon was inflated, and the same changes were seen in a more exaggerated form (FIG. 16). The differences between the breath alkane profiles were sufficient to distinguish between the normal controls and the patients with unstable angina with 100% sensitivity and specificity (FIG. 17).

Part B

Breath tests were performed in 19 patients with acute onset chest pain in a hospital Emergency Department. All were subsequently admitted to a cardiac care unit for treatment and further evaluation with a comprehensive battery of tests including echocardiography, exercise electrocardiography, myocardial scintigraphy and Holter monitoring. The final diagnoses in the 19 patients were unstable angina in ten, and acute myocardial infarction in nine. The results of the breath test in all patients demonstrated that the mean breath alkane profile was displaced upwards from the mean profile observed in the normal controls, consistent with an increased predominance of synthesis over clearance of alkanes (FIG. 18). The differences between the breath alkane profiles were sufficient to distinguish between the normal controls and the patients with cardiac chest pain with 100% sensitivity and specificity (FIG. 19). In addition, the differences between the breath alkane profiles were sufficient to distinguish between the patients with unstable angina and acute myocardial infarction with 100% sensitivity and specificity (FIG. 20).

Interpretation: In the two separate pilot studies, breath tests of patients with cardiac chest pain yielded similar results: the mean breath alkane profile was displaced upwards from the mean profile observed in the normal controls, consistent with an increased predominance of synthesis over clearance of alkanes. This is consistent with myocardial ischemia causing increased OFR activity in myocardial cells. Displacement of the breath alkane profiles was sufficient to distinguish between the normal controls and the patients with cardiac chest pain with 100% sensitivity and specificity.

The Breath Alkane Profile and Alkyl Alcohol Profile in Heart Transplant Resection Experimental methods: Heart transplant recipients were studied at three academic program sites: Newark Beth Israel Medical Center, Newark, N.J., Mt. Sinai Medical Center, New York, and Columbia Presbyterian Medical Center, New York. 213 breath tests were performed in heart transplant patients on the same day as regular scheduled endomyocardial biopsy. Breath alkane and alkyl alcohol profiles were determined in all subjects employing the methods described above. The "gold standard" of heart transplant rejection was determined as follows: Two pathologists independently graded the degree of rejection in the endomyocardial biopsy without knowledge of each other's findings, employing a standard rating scale from 0 (no rejection) through Ia, Ib, II and IIIa (mild, moderate and severe rejection) (Billingham M E, Cary N R B, Hammond M E et al: A working formulation for the standardization of nomenclature in the diagnosis of heart and lung rejection: Heart rejection study group. J Heart Transplantation 1990; 9: 587–593). The criterion for concurrence of the two readings was that both pathologists agreed that the biopsy fell into the category of no treatment required (endomyocardial biopsy with rejection grades 0, Ia or Ib) or treatment required (endomyocardial biopsy with rejection grades II or III). Two sets of data—the breath alkane profile and the breath alkyl alcohol profile—were combined for statistical analysis by logistic regression, in order to determine the probability, based upon the breath test alone, that a patient should be assigned to the treatment or no-treatment group.

Results: All patients recruited for the research were able to donate a breath sample into the BCA, and none reported any discomfort or adverse effects from the breath collection procedure. In summary:
1. 213 breath samples and endomyocardial biopsies were obtained.
2. The pathologists concurred on 195 endomyocardial biopsies: no treatment required in 182 and treatment required in 13.
3. The breath alkane profiles are shown in FIG. 21 for three groups: normal controls (50), heart transplant recipients requiring no treatment, and heart transplant recipients requiring treatment.
4. The breath alkyl alcohol profiles for the same three groups are shown in FIG. 22.
5. Compared to normal controls, both the breath alkane profiles and the breath alkyl alcohol profiles were significantly elevated in the heart transplant recipients.
6. Amongst the heart transplant recipients, the following alkanes were significantly increased in the group requiring treatment compared to those requiring no treatment: decane, undecane and pentadecane ($p<0.05$, 2-tailed t-test).
7. Amongst the heart transplant recipients, the following alkyl alcohols were significantly increased in the group requiring treatment compared to those requiring no-treatment: hexadecanol and heptadecanol ($p<0.01$, 2-tailed t-test).
8. Logistic regression analysis of the breath alkane profiles combined with the breath alkyl alcohol profiles separated the heart transplant recipients requiring no treatment from those requiring treatment. The receiver operating characteristic (ROC) curve is shown in FIG. 23. At the shoulder of the curve, the breath test was 84.6% sensitive and 80.2% specific.

Conclusions
1. In heart transplant recipients, the combination of the breath alkane profile and the breath alkyl alcohol profile distinguished with high sensitivity and specificity between those with low-grade rejection requiring no treatment and those with higher grade rejection requiring treatment.
2. The difference between the two groups appeared to result from differences in the relative severity of oxidative stress.
3. Oxidative stress appeared to be increased in all heart transplant recipients, regardless of the state of rejection activity on the endomyocardial biopsy.

The Breath Alkane Profile in End Stage Renal Disease

Clinical study: Breath VOC samples were collected before and after hemodialysis in 40 patients with ESRD, and assayed by gas chromatography and mass spectroscopy using the methods described previously. The study was performed at the Richmond Kidney Center, Staten Island, N.Y. Breath samples were also studied in a control group of 50 healthy normal subjects (mainly physicians, nurses and staff at St. Vincent's Medical Center, Staten Island, N.Y.). All subjects had fasted overnight, and samples were collected between 7.00 am and 11.00 am.

Results of Clinical Study

The etiology of ESRD in these patients is shown in Table 3 a. Alkane profile: FIG. 24 shows the mean breath alkane profile in 50 normal controls (described previously), 40 ESRD patients prior to hemodialysis, and 33 of these patients after hemodialysis. The alveolar gradients of C5, C7, C8 and C9 alkanes were significantly higher in the ESRD patients than in the normals. However, there were no significant differences in the alkane profiles of ESRD patients between their pre- and post-hemodialysis values.

B. Other VOCs: Table 4 lists 38 VOCs which were significantly higher in ESRD patients than in normal controls ($p<0.05$). None of these VOCs were significantly reduced by hemodialysis. Table 5 lists 19 VOCs which were significantly lower in ESRD patients than in normal controls ($p<0.05$). Only one of these VOCs was significantly increased by hemodialysis.

Interpretation a. Alkane profile: The alkane profile is an indicator of oxidative stress induced by oxygen free radicals (OFR'S) (FIG. 25). These results indicate that oxidative stress is increased in patients with ESRD, and that it is not significantly reduced by hemodialysis. These findings are consistent with previous reports (8,10).

Significance: The breath alkane profile may provide new and non-invasive marker of the severity of the underlying pathology in chronic renal failure which is causing oxidative stress. This may provide a clinically useful new method for monitoring the effects of new treatments designed to reverse the underlying cause of renal failure.

B. VOCs increased in ESRD: Several VOCs were significantly increased in the pre-hemodialysis ESRD patients compared to normal controls. Apart from the alkanes and alkane derivatives (discussed above) these VOCs were predominantly benzene derivatives, which are known to be highly toxic. These VOCs may play a role in the increased morbidity and mortality of ESRD patients. The origin of these VOCs is not known. One possible source may be bacteria in the large bowel.

Significance: The breath VOC assay reveals toxic VOCs in ESRD patients which may explain, in part, their increased mortality. The breath test can monitor the effectiveness of any new treatment designed to reduce these toxic VOCs.

C. VOCs decreased in ESRD: Several VOCs were significantly decreased in the pre-hemodialysis ESRD patients compared to normal controls. Some of these VOCs may possibly be synthesized in the renal parenchyma.

Significance: The breath VOC assay for VOCs reduced in ESRD may provide a new and non-invasive marker of reduced renal function.

The Breathe Alkane Profile to Determine Aging

Methods: 50 normal humans were studied (age range 23 to 75, median 35). Volatile organic compounds (VOCs) in alveolar breath were captured on sorbent traps and assayed by gas chromatography and mass spectroscopy. Alveolar gradients (concentration in breath minus concentration in ambient room air) of alkanes were determined.

Results: C4 to C20 alkanes were observed in breath and room air. Their mean alveolar gradients were negative from C4 to C12 and positive from C13 to C20. The mean age of the older half of the group was significantly greater than the younger half (47.56 yrs vs 29.88 yrs, $p<0.0001$), and the mean alveolar gradients of four alkanes (C5, C6, C7 and C8) were significantly more positive in the older subjects ($p<0.05$). There were no significant differences between males and females.

The spectrum of alkanes in normal human breath contained apparent new markers of oxidative stress. The mean rate of clearance (via cytochrome P450) exceeded the mean rate of synthesis (by ROS-mediated oxidative stress) for C4–C12 alkanes, while synthesis was greater than clearance for C13–C20 alkanes. The elevated alkane profile in older subjects was consistent with an age-related increase in oxidative stress, though an age-related decline in alkane clearance rate may have contributed.

Oxygen is a paradoxical element: it supports aerobic life, yet it is also highly toxic. Aerobic organisms generate most of their energy by reducing molecular oxygen to water, with the addition of four electrons (1). This process also generates reactive oxygen species (ROS) which are highly toxic by-products. ROS inflict a constant barrage of peroxidative damage upon proteins, DNA, lipid membranes and other biologic molecules (2–4) (FIG. 26). This process has been implicated in cellular aging as well as cellular damage in several pathological processes (5–7). ROS are constantly manufactured in the body and cleared by antioxidant scavenging and enzymic degradation; the damage inflicted by uncleared ROS is termed oxidative stress.

The Breath Methylated Alkane Contour in Normal Humans

Collection of breath and air samples: The method has been described in Phillips M, Gleeson K, Hughes J M B, Greenberg J, Cataneo R N, Baker L and McVay W P: Volatile organic compounds in breath as markers of lung cancer: a cross-sectional study. Lancet 353:1930–33; 1999; and Phillips M: Method for the collection and assay of volatile organic compounds in breath. Analytical Biochemistry 247: 272–278; 1997, as well as U.S. Pat. No. 5,465,728 entitled "Breath Collection," and U.S. application Ser. No. 09/229,020 entitled "A Breath Test for the Detection of Various Diseases," all incorporated herein by reference. VOC's in breath and room air were collected with a breath collection apparatus (BCA), a portable microprocessor-controlled device. Subjects wore a nose clip while inspiring and expiring through a low-resistance disposable mouthpiece into a wide bore breath reservoir (1.0 inch dia) open to the atmosphere at its distal end. The breath reservoir was heated in order to prevent condensation of water. Alveolar breath was pumped from the breath reservoir through a sorbent trap where the breath VOCs were captured on activated carbon (200 mg Carbotrap C (20/40 mesh) and 200 mg Carbopack B (60/80 mesh) (Supelco, Inc, Bellefonte, Pa.). The geometry of the system ensured that the sample comprised alveolar breath virtually uncontaminated by dead-space air. The collection period was 2.0 min at 0.5 l/min, and VOCs in two separate 1.0 l samples were collected: one of breath, and one of background room air.

Breath VOC assay: The method has been described in Phillips M, Gleeson K, Hughes J M B, Greenberg J, Cataneo R N, Baker L and McVay W P: Volatile organic compounds in breath as markers of lung cancer: a cross-sectional study. Lancet 353:1930–33; 1999; and Phillips M: Method for the collection and assay of volatile organic compounds in breath. Analytical Biochemistry 247: 272–278; 1997, incoporated herein by reference. VOC's were desorbed from the sorbent trap heating it to 300° C. in an automated thermal desorber (ATD 400, Perkin Elmer, Norwalk, Conn., USA). A stream of helium flushed the VOC's onto a concentrator, a refrigerated sorbent trap maintained at 0° C. The concentrated sample of VOC's was then heated to 300° C., and the volatilized VOC's were separated by gas chromatography (GC), and identified and quantified by mass spectroscopy (MS).

Human subjects: Breath samples were collected between 7.00 am and 12.00 noon from 99 normal volunteers aged from 9 to 89 who had fasted from the previous midnight. Subjects sat for approximately 30 min prior to the collections of breath and air in order to allow time for equilibration between VOC's in room air and in the blood. Human research was approved by the institutional review board of St. Vincent's Medical Center, Staten Island, N.Y.

Analysis of data: The relative abundance of each alkane (C4 to C20) and its methylated derivatives were determined by the ratio of its chromatographic area under the curve (AUC) to the AUC of internal standard (0.25 ml 2 ppm 1-bromo-4-fluoro-benzene, Supelco). The alveolar gradient of each VOC was determined as the abundance in alveolar breath minus the abundance in room air. In each subject, a three dimensional breath methylated alkane contour (BMAC) was constructed by plotting the carbon skeleton length (x-axis) versus the methylation site (z-axis) versus the alveolar gradient (y-axis).

Results

The median age was used to split the group into younger and older halves (younger half: n=49, range 9–40, mean= 30.3 years; older half: n=50, range 40–89, mean=68.3 year; p<0.0001).

The mean BMACs are shown for all subjects, younger subjects and older subjects in FIGS. 2, 3 and 4 respectively. 25 of these VOCs were significantly different in the two groups (Table 1).

Smokers (n=11) were compared to age matched non-smokers; their mean BMACs are shown in FIGS. 5 and 6 respectively. From the above, it was found that:

1. The BMAC was developed as a new marker of oxidative stress in humans.
2. The mean BMAC in normal humans varied with age: 25 species of alkanes and methylated alkanes were significantly different in older and younger subjects. Since most of the compounds were increased in the older subjects, these differences may have been due to
   a. an increase in oxidative stress with age, or
   b. a decrease in metabolism by cytochrome p450 enzymes with age, or
   c. a combination of a and b These findings were consistent with previous reports of increased oxidative stress and breath pentane concentrations with age in normal humans. Zarling E J, Mobarhan S, Bowen P and Kamath S: Pulmonary pentane excretion increases with age in healthy subjects. Mech Ageing Dev 67(1–2): 141–7; 1993; Jones M, Shiel N, Summan M, Sharer N M, Hambleton G, Super M and Braganza J M: Application of breath pentane analysis to monitor age-related change in free radical activity. Biochem Soc Trans 21(4): 485S; 1993.

3. The mean BMAC in normal humans varied with smoking status. Compounds were both increased and decreased in the smokers, these differences were most likely due to a combination of:
   a. Increased clearance of alkanes and methylalkanes by cytochrome p450 enzymes induced smoking. This is consistent with previous reports that tobacco smoking is a potent inducer of cytochrome p450 enzymes. Zevin S and Benowitz N L: Drug interactions with tobacco smoking. An update. Clin Pharmacokinet 1999;36(6):425–38; Pasanen M and Pelkonen O: The expression and environmental regulation of P450 enzymes in human placenta. Crit Rev Toxicol 1994;24(3):211–29; Nebert D W, Petersen D D and Puga A: Human AH locus polymorphism and cancer: inducibility of CYP1A1 and other genes by combustion products and dioxin. Pharmacogenetics 1991;1 (2):68–78.
   b. Increased oxidative stress with smoking, which is also likely in view of previous reports linking smoking with oxidative stress Kalra J, Chaudhary A K and Prasad K: Increased production of oxygen free radicals in cigarette smokers. Int J Exp Pathol 1991;72(1):1–7; Bridges A B, Scott N A, Parry G J and Belch J J: Age, sex, cigarette smoking and indices of free radical activity in healthy humans. Eur J Med 1993;2(4):205–8; Church D F and Pryor W A: Free-radical chemistry of cigarette smoke and its toxicological implications. Environ Health Perspect 1985;64:111–26.

The Breath Methylated Alkane Contour in Heart Transplant Rejection

Testing for Oxidative Stress in Heart Transplant Rejection

More than 17,000 people now live with a transplanted heart in the United States. Source: United Network for Organ Sharing, Richmond, Va. Scientific Registry data. All of them require periodic screening for heart transplant rejection, but this condition is frequently difficult to detect. Clinical manifestations such as malaise, fatigue, dyspnea, edema, and anorexia are all relatively insensitive and non-specific; so too are non-invasive tests such as electrocardiography, echocardiography, thallium scintigraphy and magnetic resonance imaging. Hence, right ventricular endomyocardial biopsy remains the standard against which all other tests are compared Hosenpud J D: Noninvasive diagnosis of cardiac allograft rejection. Circulation 1991;85:368; Duquesnoy R J, Demetris A J: Immunopathology of cardiac transplant rejection. Curr Opinion Cardiol 1995; 10:155; Winters G L: The pathology of heart allograft rejection. Arch Pathol Lab Med 1991;115:226; Caves B C, Billingham M E, Stinson E B and Shumway N E: Serial transvenous biopsy of the transplanted human heart: improved management of acute rejection episodes. Lancet 1974;I:821; Winters G L, Loh E, Schoen F J: Natural history of focal moderate cardiac allograft rejection, Circulation 1995;91:1975. Endomyocardial biopsy is employed to identify allograft rejection or infection, and assess the efficacy of treatment. Post-operative biopsies are generally performed weekly for the first six weeks, biweekly until the third month, then monthly until the sixth month. Subsequent biopsies are scheduled on an individual basis. However, right ventricular endomyocardial biopsy is an invasive and comparatively expensive procedure which may result in complications including hematoma, infection, arrhythmia, ventricular perforation, and fistulas. This has stimulated research into alternative non-invasive tests for heart transplant rejection such as breath microanalysis. Sobotka P A, Gupta D K, Lansky D M, Costanzo M R and Zarling E J: Breath pentane is a marker of acute cardiac allograft rejection. J Heart Lung Transplant 1994; 13:224"9.

Breath tests for heart transplant rejection are based on two observations: First, allograft rejection is accompanied by oxidative stress, due to the increased production of reactive oxygen species (ROS) in the myocardium Coles J G; Romaschin A D; Wilson G J; Mickle D A; Dasmahapatra H; Martell M; Mehra A; Tsao P: Oxygen free radical-mediated lipid peroxidation injury in acute cardiac allograft rejection. Transplantation 1992; 54(1):175–8; Roza A M; Pieper G; Moore-Hilton G; Johnson C P; Adams M B: Free radicals in pancreatic and cardiac allograft rejection. Transplant Proc 1994 26(2):544–5). Second, ROS degrade cellular membranes by lipid peroxidation of polyunsaturated fatty acids (PUFAs), evolving alkanes and alkane derivatives which are excreted in the breath as volatile organic compounds (VOCs) (Kneepkens C M F, Ferreira C, Lepage G and Roy C C: The hydrocarbon breath test in the study of lipid peroxidation: principles and practice. Clin Invest Med 1992; 15(2):163–186; Kneepkens C M F, Lepage G, Roy C C. The potential of the hydrocarbon breath test as a measure of lipid peroxidation. Free Radic Biol Med 1994;17:127–60.) (FIG. 35). Animal studies have also demonstrated increased oxidative stress in allografts of heart and liver. Kuo P C; Alfrey E J; Krieger N R; Abe K Y; Huie P; Sibley R K; Dafoe D C: Differential localization of allograft nitric oxide synthesis: comparison of liver and heart transplantation in the rat model. Immunology 1996 April;87(4):647–53; Winlaw D S; Schyvens C G; Smythe G A; Du Zy; Rainer S P; Keogh A M; Mundy J A; Lord R S; Spratt P M; MacDonald P S: Urinary nitrate excretion is a noninvasive indicator of acute cardiac allograft rejection and nitric oxide production in the rat. Transplantation Nov 15, 1994;58(9):1031–6. The resulting chemical and anatomical disruption of membranes may progress to cellular dysfunction and death. VOC's produced by this process include alkanes (e.g. pentane) and alkane derivatives which are excreted in the breath where they may provide clinically useful markers of oxidative stress. The breath methylated alkane contour (BMAC) was employed to study breath markers of rejection in heart transplant patients undergoing endomyocardial biopsy.

Material and Methods

Human subjects: Characteristics of the subject population are shown in Table 2. 210 technically satisfactory breath VOC samples were collected from heart transplant recipients on the same day as regular scheduled endomyocardial biopsy. Patients were studied at three sites: Newark Beth Israel Medical Center, Newark, N.J. (n=24), Mt. Sinai Medical Center, New York, N.Y. (n=37), and Columbia Presbyterian Medical Center, New York, N.Y. (n=149). Twenty (20) age-matched normal controls were selected from a data base of fasting normal subjects studied at the Sisters of Charity Medical Center, St. Vincent's Campus, Staten Island, N.Y. (14). The research was approved by the institutional review boards of all participating institutions.

Breath collection and assay: The method has been described in Phillips M, Herrera J, Krishnan S, Zain M, Greenberg J and Cataneo R N: Variation in volatile organic compounds in the breath of normal humans, Journal of Chromatography B 629(1–2):75–88; 1999 and in Phillips M: Method for the collection and assay of volatile organic compounds in breath. Analytical Biochemistry 247: 272–278; 1997. In summary, a portable BCA was employed to capture the VOCs in 1.0 l breath onto a sorbent trap; VOCs in 1.0 l room air were captured on a separate sorbent trap. Subjects wore a nose clip while breathing in and out of the disposable mouthpiece of the BCA for 2.0 min. Light flap valves in the mouthpiece presented low resistance to respiration, and it was possible to collect breath samples without discomfort even from elderly patients and those suffering from pulmonary disease. All sorbent traps were sent to the laboratory for analysis of VOCs by ATD/GC/MS.

Grading of rejection: Endomyocardial biopsies were jointly evaluated by two pathologists who graded the degree of rejection employing a standard rating scale from 0 (no evidence of rejection) through Ia, Ib, II and IIIa. Billingham M E, Cary N R B, Hammond E H et al: A working formulation for the standardization of nomenclature in the diagnosis of heart and lung rejection. Heart rejection study group. Heart Transplant 1990;9:587.

Masking procedures: Sorbent traps were analyzed for VOCs in the laboratory by technical assistants who had no knowledge of the pathological findings. The pathologists reviewing the biopsies had no knowledge of the results of the breath test;

Analysis of data: All chromatograms of breath and air were automatically downloaded into computer-based spreadsheets, and then into a computer-based relational data base. The breath methylated alkane contour (BMAC) was determined in all subjects.

Results

Human subjects and endomyocardial biopsies: All human subjects recruited for the research were able to donate a breath sample into the BCA, and none reported any discomfort or adverse effects from the breath collection procedure. Two pathologists graded rejection in the endomyocardial (22.9%), Ib 14/210 (56.7%), II 23/210 (10.9%) and IIIa 7/210 (3.3%). Only one of the age-matched normal controls and three of the transplant recipients were smokers, so the potential effects of smoking were not analyzed separately.

Breath VOCs: Differences between heart transplant recipients and normals: The mean BMACs of heart transplant recipients with Grade 0 rejection (i.e. no histological evidence of rejection) and age-matched normal controls are shown in FIG. 36 and Table 3

Breath VOCs: Differences between heart transplant recipients with different grades of rejection: The mean BMACs of heart transplant recipients with Grade 0, Grade Ia and Ib, Grade II and Grade IIIa rejection are shown in FIG. 37 and Table 4.

Determination of sensitivity and specificity: The BMACs were analyzed by logistic regression in order to compare the results of the breath test in heart transplant recipients with no evidence of rejection (Grade 0) to those with any evidence of rejection (Grades Ia, Ib, II and IIIa). The probability of heart transplant rejection was calculated for each patient, and displayed in a scatter diagram (FIG. 38). The sensitivity and specificity of the breath test was determined from these values (FIG. 39). The BMAC identified Grade IIIa rejection with 100% sensitivity and 68.6% specificity, Grade II rejection with 73.9% sensitivity and 64.4% specificity, and Grade Ia and Ib rejection with 75.8% sensitivity and 64.4% specificity.

From the results of the study, the following conclusions can be drawn:

1. Oxidative stress was greater in heart transplant recipients than in age-matched normal controls.
2. Oxidative stress increased with the severity of heart transplant rejection.
3. The breath test was sensitive and specific for clinically significant rejection.

1. Oxidative Stress Was Greater in Heart Transplant Recipients than in Age-matched Normal Controls.

Compared to age-matched normal controls, the BMAC was significantly elevated in heart transplant recipients who had no microscopic signs of rejection in their endomyocardial biopsy. The differences were qualitatively similar to the differences observed between normal non-smokers and smokers (FIGS. 5 and 6). This finding is consistent with an abnormally high level of oxidative stress in the transplanted heart, possibly resulting from chronic subclinical inflammation and/or rejection. Oxidative stress has been proposed as a risk factor for coronary artery disease, but the linkage has not been convincingly proven. Runge M S: The role of oxidative stress in atherosclerosis: the hope and the hype. Trans Am Clin Climatol Assoc 1999;110:119–29; Hoeschen R J: Oxidative stress and cardiovascular disease. Can J Cardiol 1997; 13(11):1021–5. However, accelerated coronary artery disease is now the major cause of death in heart transplant recipients who have survived more than one year (Radovancevic B and Frazier O H: Heart transplantation: approaching a new century. Tex Heart Inst J 1999;26(1) :60–70; Deng M C, Tjan T D, Asfour B, Roeder N and Scheld H H: Transplant vasculopathy. Herz 1998;23 (3):197–201), and increased oxidative stress may play a role in its development.

2. Oxidative stress increased with the severity of heart transplant rejection.

Coenzyme Q10 is depleted in transplanted human hearts, and mitochondrial respiratory chain function and energy production vary with the histological severity of rejection (Gvozdjakova A, Kucharska J, Mizera S, Braunova Z, Schreinerova Z, Schramekova E, Pechan I and Fabian J: Coenzyme Q10 depletion and mitochondrial energy disturbances in rejection development in patients after heart transplantation. Biofactors 1999;9(2–4):301–6.), so it is possible that increased oxidative stress might have been caused by impaired mitochondrial function.

3. The breath test was sensitive and specific for clinically significant rejection.

In most heart transplant centers, only Grade III rejection is treated aggressively. The sensitivity and specificity of the breath test in in heart transplant recipients with Grade II and Grade III rejection was sufficiently high to serve as a screening test to identify those who required additional evaluation and treatment from those who did not. The test was non-invasive, safe, and highly acceptable to patients. Breath testing of heart transplant recipients could potentially reduce the number of endomyocardial biopsies performed every year, with a consequent reduction in patient morbidity and health-care costs.

The BMAC: A New Marker of Aging

Background: Power plants, biological or man-made, commonly produce toxic byproducts. Mammalian life is sustained by the energy produced in mitochondrial power plants which also convert oxygen to toxic and potentially lethal byproducts. Oxygen is the final acceptor of electrons in oxidative metabolism, but electron leakage from the mitochondria in the form of reactive oxygen species (ROS) inflicts oxidative stress, a constant barrage of oxidative damage to DNA, proteins, lipids and other biologically important molecules (Butterfield, 1998; 854:448–62). Oxidative stress has been implicated as a pathologic mechanism in aging and several diseases, but it has proved difficult to measure its intensity in vivo (Pryor, Free Radic Biol Med 1991;10:3–4). Various markers of oxidative stress have been proposed, including malonaldehyde and conjugated dienes in the blood, and hydrocarbons and hydrogen peroxide in the breath (Kneepkens C M F, et al Clin Invest Med 1992; 15(2):163). Volatile markers of oxidative stress have attracted attention because breath tests are intrinsically non-invasive and painless (Phillips M: Sci Amer1992; 267(1): 74–79). Increased breath alkanes, particularly ethane and pentane, have demonstrated increased oxidative stress in breast cancer, rheumatoid arthritis, heart transplant rejection, acute myocardial infarction, schizophrenia and bronchial asthma (Phillips M et al J Chrom B 1999; 729: 75–88). Breath ethane and pentane are of limited value in screening for these disorders because their sensitivity and specificity are poor.

However, oxidative stress appears to generate other degradation products which are excreted as volatile organic compounds (VOCs) in the breath (FIG. 40). Phillips has previously reported that longer chain alkanes and methylated alkanes can be detected in the breath of normal humans as well as in patients with lung cancer (Phillips M et al Lancet 1999; 353:1930–33) and that a spectrum of C4 to C20 alkanes, the breath alkane profile, increased significantly with age (Phillips M et al Free Rad Res (accepted for publication)). This study describes an extension of the breath alkane profile into a new three-dimensional display of apparent markers of oxidative stress, the breath methylated alkane contour (BMAC), and the variation of the BMAC with age in normal humans.

Clinical Study

Human subjects: Breath samples were collected between 7.00 am and 12.00 noon from 102 normal volunteers aged from 9 to 89 years who had fasted from the previous midnight. Subjects sat for approximately 20 min prior to the collections of breath and air in order to allow time for equilibration between VOCs in room air and in the blood. The institutional review board of the Sisters of Charity Medical Center, Staten Island, N.Y., approved the human research.

Analysis of data: The relative abundance (R.A.) of each alkane (C4 to C20) and its monomethylated derivatives were determined from the chromatographic area under the curve (AUC) and the AUC of an internal standard (IS) (0.25 ml 2 ppm 1-bromo-4-fluoro-benzene, Supelco) (R.A.$_{VOC}$=AUC$_{VOC}$/A$_{UC\ IS}$) The alveolar$_{gradient}$ of each VOC was determined as R.A.$_{breath}$–R.A.$_{room}$ air [Phillips, 1999 #23]. In each subject, a breath methylated alkane contour (BMAC) was constructed by plotting the carbon skeleton length (x-axis) versus the methylation site (z-axis) versus the alveolar gradient (y-axis).

Results: Subjects were separated into four quartiles by age. Breath data were pooled from subjects in each quartile in order to determine their mean alveolar gradients of alkanes and monomethylated alkanes. These values were displayed as the mean BMAC for each quartile (FIG. 41); significant differences between quartiles were determined with one-way ANOVA and a Neuman-Keuls post hoc test (Table 10). When subjects were matched for age, there were no significant differences between tobacco smokers and non-smokers; the only difference with sex was 4-methyloctane (greater in females than in males, $p<0.05$, 2-tailed t-test).

Conclusions

1. C4 to C20 alkanes and their monomethylated derivatives comprise a family of apparent new markers of oxidative stress.
2. The BMAC showed a progressive and significant elevation with age in normal humans, consistent with previous reports that aging is accompanied by increased oxidative stress.

The BMAC: A New Marker of Ischemic Heart Disease

Background: More than 3 million patients are hospitalized every year in the United States for chest pain. The cost is over $3 billion just for those found to be free of acute disease (Roberts R R, Zalenski R J, Mensah E K et al: JAMA 1997;278(20):1670–6). Many patients with acute chest pain but without myocardial infarction are admitted to specialized services to determine the cause of their pain (Hoekstra J W and Gibler W B: JAMA 1997;278(20):1701–2.). The main objective is to detect unstable angina, which is potentially life threatening. Evaluation of these patients is frequently extensive and expensive, entailing a comprehensive battery of tests such as echocardiogaphy, exercise electrocardiography (ECG), myocardial scintigraphy and Holter monitoring. Employing such a battery of tests, Fruergaard et al evaluated 204 patients with acute chest pain but without myocardial infarction. They found the commonest etiology was gastro-esophageal disease, followed by ischemic heart disease and chest wall syndrome. The high risk subset comprised less than a third of all diagnoses (Fruergaard P, Laundbjerg J, Hesse B et al: Eur Heart J 1996;17(7):1028–34). McCullough et al determined that the practice of hospital admission for patients with chest pain and essentially normal ECGs was not cost favorable, at $1.7 million dollars per life saved (McCullough P A, Ayad O, O'Neill W W and Goldstein J A: Clin Cardiol 1988;21(1):22–6). Despite these and other well-documented studies, patients with acute chest pain but without myocardial infarction are commonly hospitalized because physicians are generally reluctant to discharge a patient if there is a risk of unstable angina and sudden death.

There is a clinical and an economic need for a diagnostic test which could differentiate between the high-risk patient with cardiac chest pain who could benefit from hospitalization, and the low-risk patient with non-cardiac chest pain who could be safely discharged from the hospital and evaluated as an out-patient. A breath test could potentially provide this information because myocardial oxygen free radical activity is increased in ischemic heart disease. Weitz et al reported that breath pentane was significantly increased in 10 patients with acute myocardial infarction compared to 10 healthy controls (Weitz Z W, Birnbaum A J, Sobotka P A, Zarling E J and Skosey J L: Lancet 1991;337:933–35.). However, these results were called into question by a subsequent study from the same institution which found no significant differences in breath pentane between patients with acute myocardial infarction, stable angina and normal controls (Mendis S, Sobotka P A and Euler D E: Free Radic Res 1995;23(2):117–22.).

Clinical study: This study was performed at St. Vincent's Medical Center, New York City. The research was approved by the institutional review board, and all patients gave their signed informed consent to participate. Breath tests were performed in 30 patients with unstable angina documented by coronary angiography. The breath test was then repeated in these patients during coronary angioplasty while the balloon was still inflated. BMACs were determined as described above, and compared in these patients and in 38 age-matched normal controls. BMACs in normals and patients with unstable angina were compared by logistic regression in order to determine the probability of heart disease based upon the breath test alone.

Results: The mean BMACs in age-matched normals and patients with unstable angina (before and during coronary angioplasty) are shown in FIG. 42. There were significant differences between age-matched normals and patients with unstable angina (before coronary angioplasty) in the mean abundance of components of the BMAC (Table 11). The probability of unstable angina based upon logistic regression analysis of the BMAC is shown in FIG. 43.

Conclusions

1. There were significant differences between components of the BMAC in patients with unstable angina and in age-matched normal controls.
2. These differences were consistent with increased oxidative stress in unstable angina.
3. Components of the mean BMAC in patients with unstable angina were further increased during subsequent coronary angioplasty, consistent with increased oxidative stress during this procedure. However, this finding might have been influenced by breathing oxygen during the procedure.
4. The differences in BMAC between patients with unstable angina and age-matched normal controls were sufficient to distinguish the two groups with 100% sensitivity and specificity.
5. The BMAC could provide a clinically useful new test to identify patients with cardiac chest pain.

The BMAC: A New Marker of Renal Failure

Background: Clinicians who come into contact with patients with chronic renal failure are familiar with the classic odor of uremic breath. It has been variously described as "fishy", "ammoniacal" and "fetid". Schreiner and Maher in their review of uremia described it as ammoniacal, comparing it to the smell of stale urine (Schreiner G E and Maher J F: Uremia: Biochemistry, pathogenesis and treatment. Springfield, Ill., C C Thomas 1961, p 335.). Since the introduction of early dialysis in chronic renal failure, the debilitated patient with a foul mouth due to ulceration and bacterial overgrowth is seldom seen. However, a consistent fishlike odor is still noticeable in patients with end stage renal disease (ESRD), suggesting that it is systemic in origin rather than from bacteria in the mouth. In 1963, Simenhoff et al reported increased levels of dimethylamine in the blood, cerebrospinal fluid and brain of patients with severe uremia (Simenhoff M L, Asatoor M L, Milne M D et al: Clin Sci 1963;25:65–77). They extended this research with analysis of breath of uremic patients, employing GC (Simenhoff M L, Burke J F, Saukkonen J J, Ordinario A T and Doty R: N Engl J Med 1977;297:132–135.). They found increased concentrations of secondary and tertiary amines, dimethylamine and trimethylamine. Both were significantly reduced by hemodialysis as well as by treatment with nonabsorbable antibiotics. They concluded that these VOCs were responsible in part for the classic fishy odor in uremic breath, and arose from bacterial overgrowth in the intestine.

In addition, a number of recent studies have demonstrated increased oxidative stress in chronic renal failure using non-volatile markers in blood (Hasselwander O, Young I S: Free Radic Res 1998; 29(1): 1–11, Simic-Ogrizovic S et al: Transpl Int 1998; 11 supp 1: S125–9, Fiorillo C et al: Clin Chem Lab Med 1998; 36(3): 149–53). We undertook a clinical study in order to determine if the BMAC and other VOCs in breath were increased in ESRD, and the effects of hemodialysis on these compounds.

Clinical study: A group of 40 patients with end-stage renal disease (ESRD) requiring periodic hemodialysis was studied at the Richmond Kidney Center, Staten Island, N.Y. Breath samples were collected before and after hemodialysis, and the BMAC and other VOCs were determined. The control group comprised age-matched normals. The research was approved by the institutional review board of St. Vincent's Medical Center, Staten Island, N.Y., and all patients gave their signed informed consent to participate. BMACs in normal controls and pre-hemodialysis patients were compared by logistic regression.

Figure 45:
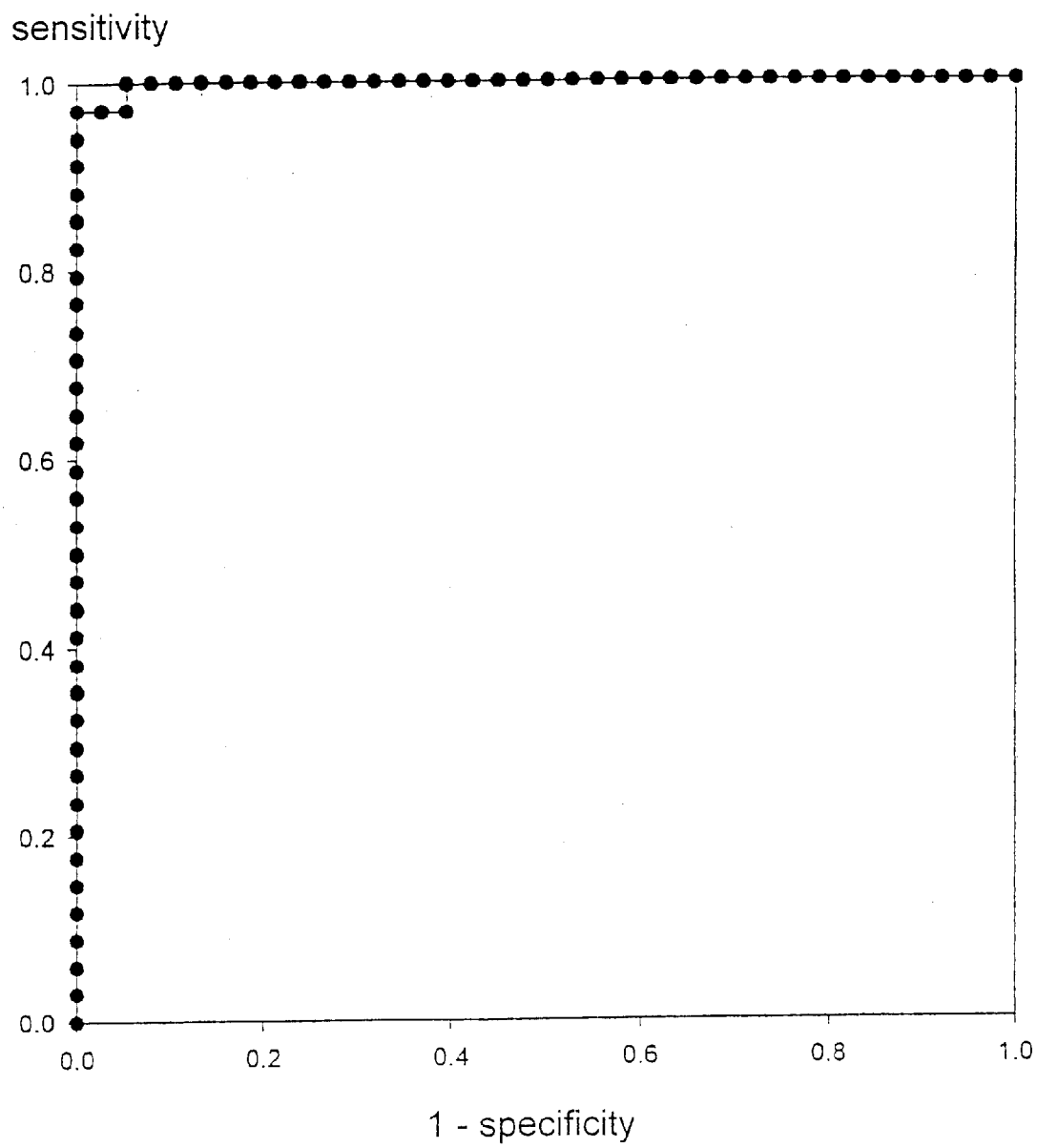

Results: The causes of ESRD in the studied patients are shown in Table 12. Mean BMACs in age-matched normals and ESRD patients before and after hemodialysis are shown in FIG. 44. Logistic regression analysis of the mean BMACs in age-matched normals and ESRD patients before hemodialysis separated the two groups with high sensitivity and specificity; the ROC curve is shown in FIG. 45. Only one component of the BMAC changed significantly with hemodialysis (4-methylnonane p<0.05). VOCs that were significantly increased and decreased in pre-hemodialysis ESRD patients (compared to age-matched normals) are shown in Table 13. Only one was significantly altered by hemodialysis (1,1-biphenyl,2,2'-diethyl-).

Conclusions
1. The mean BMAC was significantly higher in pre-hemodialysis ESRD patients than in age-matched normals, consistent with previous reports of increased oxidative stress.
2. The BMAC identified patients with ESRD with 100% sensitivity and 98% specificity
3. Hemodialysis significantly altered only one component of the BMAC, suggesting that it did not have a major impact on oxidative stress in ESRD patients.pre-hemodialysis ESRD patients (compared to age-matched normals)
4. Several other VOCs were significantly higher or lower in pre-hemodialysis ESRD patients than in age-matched normals.
5. The-BMAC and other VOCs in breath are significantly affected by ESRD and my provide clinically useful new markers of the severity of chronic renal failure.

The BMAC: A New Marker of Lung Cancer
Background: Lung cancer: Incidence and Prevalence Primary carcinoma of the lung is the leading cause of cancer death in the United States. Every year, the disease affects nearly 100,000 males and 50,000 females. Most of them die within a year of diagnosis. The peak incidence of lung cancer occurs between age 55 to 65. In high risk patients (males aged over 45 years who smoke more than 40 cigarettes a day), the prevalence of asymptomatic lung cancer is 4 to 8 case per 1000 persons, while the incidence found at follow-up screening is 4 new cases of lung cancer per 1000 persons per year. The incidence is increasing: the age-adjusted lung cancer has doubled every 15 years (Minna J D: Chap 90 in Harrison's Principles of Internal Medicine. 14th ed. Eds. Fauci A S, et al. McGraw Hill, New York 1998.). No clinically useful test for the early detection of lung cancer is currently available. Most cases of lung cancer are not detected until the disease is comparatively advanced, when it causes symptoms arising from local or metastatic growth. However, there is evidence that early detection of lung cancer might help reduce mortality. Compared to patients with metastatic disease, patients with supposedly localized disease at the time of diagnosis have better 5-year survival rates: 30% in males and 50% in females. Although these primary tumors were detected at a comparatively early stage, clinically silent and undetected metastases were present in the majority. There is therefore an urgent clinical need for a screening test which can detect lung cancer in its earliest stages before metastasis has occurred. Unfortunately, prospective screening with frequent radiography and sputum cytology has yielded disappointing results, yielding no difference in the survival rates between screened and non-screened groups of smoking males 45 years of age or older. This failure of traditional technology has stimulated research into new diagnostic tests for lung cancer, such as breath tests, which might permit earlier diagnosis and improve mortality and morbidity.

The rationale for a breath test for cancer of the lung and other organs is based on two well-documented phenomena: first, reactive oxygen species (ROS) are associated with carcinogenesis, and second, ROS promote the excretion of hydrocarbons in the breath (FIG. 40). Therefore, breath hydrocarbons might provide a marker of increased OFR activity during the development of cancer. Previous studies have reported apparent volatile markers of lung cancer in the breath (Gordon S M, Szidon J P, Krotoszynski B K, Gibbons R D and O'Neill H J: Clin Chem 1985;31:1278–82. O'Neill H J, Gordon S M, O'Neill M H, Gibbons R D and Szidon J P: Clin Chem 1988;34(8):1613–1618. Preti G, Labows J N, Kostelc J G, Aldinger S and Daniele R: J Chromatog. Biomed App1988;432:1–11). Phillips performed a pilot study of breath testing in 108 patients undergoing bronchoscopy for evaluation of a suspicious chest x-ray, and identified a combination of 22 VOCs in breath which identified lung cancer with high sensitivity and specificity. These VOCs comprised a combination of benzene derivatives, alkanes, and methylated alkanes (Phillips M, Gleeson K, Hughes J M B, Greenberg J, Cataneo R N, Baker L and Mcvay W P: Lancet 1999; 353:1930–33.). The following clinical study was performed in order to validate these findings and to evaluate the BMAC as a marker of lung cancer.

Clinical Study

Clinical sites: Patients were recruited from the pulmonary services at five academic medical centers: Charing Cross Hospital, Imperial College, London, UK, Penn State Geisinger Medical Center, Hershey, Pa., Columbia Presbyterian Medical Center, New York, N.Y., New York University Medical Center, New York, N.Y., and St. Vincent's Medical Center, New York, N.Y. Breath samples were collected on the same day as bronchoscopy, and analyzed in the manner described above in order to generate a BMAC for each subject. All patients gave their signed informed consent to participate, and the research was approved by the institutional review board at each site.

Patient recruitment: Criteria for inclusion in the study were age 18 or older, history of abnormal chest x-ray, bronchoscopy and biopsy scheduled for further evaluation, and the patient was willing to give written informed consent to participate in the research. The criterion for exclusion from the study was a history of previously diagnosed cancer of any site.

Analysis of data: Patients were divided into two groups: those with and those without lung cancer, as shown on the biopsy obtained at bronchoscopy. Using logistic regression, the components of the BMAC were analyzed to differentiate between the patients in each group, and to determine the probability of lung cancer in each individual. In addition, these data were analyzed according to TNM staging of cancer, and the histological type of cancer.

Figure 49:
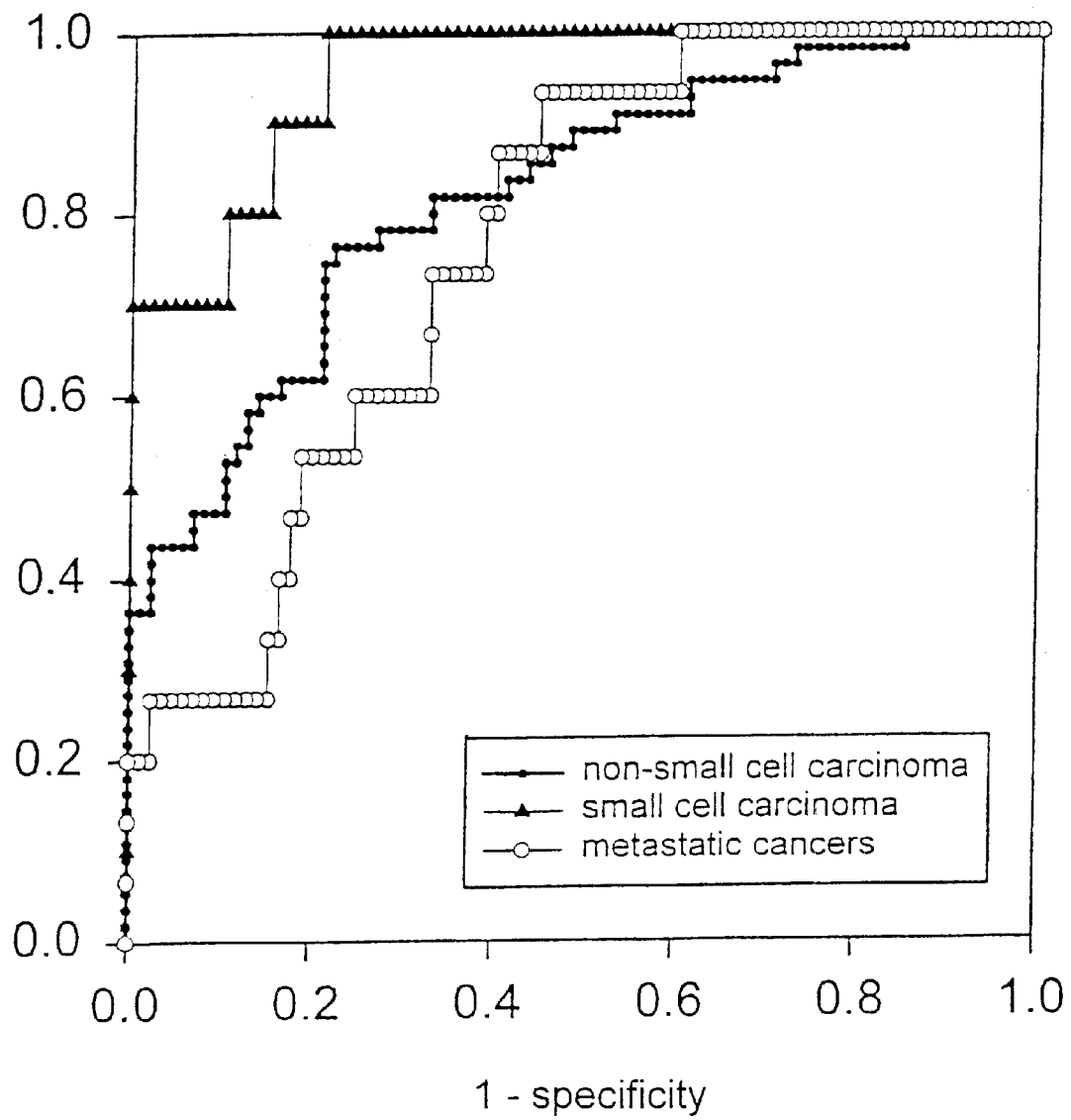

Results: Patient and tumor characteristics are shown in Table 14. Mean BMACs for patients with and without lung cancer are shown in FIG. 46. Mean BMACs for patients with metastatic lung cancer, small cell carcinoma and non-small cell carcinoma are shown in FIG. 47. ROC curves showing sensitivity and specificity of the breath test according to TNM staging of cancer and the histological type of cancer are shown in FIGS. 48 and 49 respectively.

Conclusions
1. The breath test was sensitive and specific for lung cancer.
2. Sensitivity and specificity were highest in Stage 1 cancer (>95% and 80% respectively), confirming the results of the pilot study.
3. Sensitivity and specificity were highest for non-small cell carcinoma, followed by small cell carcinoma and metastatic cancers respectively.
4. Alveolar gradients of components of the BMAC were generally lower in cancer patients, consistent with increased metabolic clearance and/or excretion. This suggests a possible mechanism for the result: increased clearance of VOCs by induced cytochrome p450 activity. This is similar to the results observed in patients with breast cancer.

The BMAC: A New Marker of Breast Cancer

Background: Breast cancer is a common disease which now affects approximately one in every ten women in the United States. Early detection by periodic screening mammography can reduce mortality by 20–30% (Henderson, chap 319, Harrison's Principles Int Med, 13$^{th}$ ed, McGraw Hill, New York, 1994). However, mammography is expensive, frequently requires painful breast compression, entails exposure to radiation, and generates false-positive results in one third of all women screened over a 10 year period (Elmore J G: N Engl J Med 1998;338: 1089–96). There is a clinical need for a screening test for breast cancer which is at least as sensitive and specific as mammography, but is simpler, safer, less painful and less expensive.

There are previous studies of breath testing in breast cancer. Hietanen et al studied 20 women with histologically proven breast cancer and a group of age and sex-matched controls (Hietanen et al: Eur J Clin Nutr 1994; 48: 575–86). Mean breath pentane concentration in the cancer patients was significantly higher than in the controls. They did not report concentrations of pentane in ambient air, nor the alveolar gradients of pentane. Ebeler et al studied tumor-bearing transgenic mice and found that they expired significantly more formaldehyde per unit metabolic size than control mice (Ebeler S E: J Chromatogr B Biomed Sci Appl 1997;702:211–5)

Other studies indicate a potential role for screening for breast cancer with a breath test for the BMAC. The cytochrome P450 (CYP) system comprises a group of mixed function oxidase enzymes which metabolize drugs and other xenobiotics. This system also metabolizes alkanes to alcohols (e.g. n-hexane to 213 and 3-hexanol) (Crosbie S J, Blaine P G and Williams F M: Hum Exp Toxicol 1997; 16(3):131–7). Rats treated with a potent cytochrome P-450 inhibitor exhibited a ten-fold increase in hexane and other breath VOCs with no increase in hepatic lipid peroxidation, demonstrating the significance of this pathway for VOC clearance (Mathews J M, Raymer J H, Etheridge A S, Velez Gr and Bucher J R: Toxicol Appl Pharmacol 1997; 146(2): 255–60.). Studies in normal animals initially suggested that the liver was the major site of clearance of alkanes from the body by cytochrome P450 metabolism (Burk-R J; Ludden-T M; Lane-J M: Gastroenterology. 1983 84(1): 138–42). However, recent studies have demonstrated that cytochrome P450 metabolism is not confined to the liver. Metabolism of alkanes to alcohols has also been observed in lung, brain and skeletal muscle microsomes expressing cytochrome P450 2E1 or 2B6 (Crosbie S J, Blaine P G and Williams F M: Hum Exp Toxicol 1997; 16(3):131–7). The cytochrome P450 system is also present in human breast tissue. Murray et al reported that cytochrome P450 CYP1B1 was expressed in cancers of breast as well as other tissues (Murray G I, Taylor M C, McFadyen M C, McKay J A, Greenlee W F, Burke M D and Melvin W T: Cancer Res 1997;57(14):3026–31.). Huang et al detected activity of the xenobiotic-metabolizing CYP1, CYP2 and CYP3 subfamilies of cytochrome P450 in human breast tissue (Huang Z, Fasco M J, Figge H L, Keyomarsi K and Kaminsky L S: Drug Metab Dispos 1996;24(8):899–905). They observed:" . . . When normal and tumor tissues were from the same individuals, higher amplification occurred in normal tissues . . . The machinery of possible in situ bioactivation of xenobiotics and modification of therapeutic drugs is thus present in human breast tissue".

Taken together, these studies demonstrate:
1. Alkanes are metabolized in vivo by cytochrome P450 enzymes
2. Cytochrome P450 enzymes are present in normal and neoplastic human breast tissues
3. Breast cancer induces increased cytochrome P450 activity in normal breast tissue
4. Breast cancer may therefore induce increased metabolism of alkanes Clinical study: Breath samples were collected from a group of women undergoing screening mammography at Regional Imaging and Therapeutic Radiology Service PC, Staten Island. All gave their signed informed consent and the research was approved by the institutional review board of St. Vincent's Medical Center of Richmond. Breath and air samples were collected and analyzed in the manner described above, and the BMAC was determined in all subjects. This non-random sample was intentionally skewed to include a relatively large number of women with breast cancer. 36 women were studied on the same day mammography was performed: 23 with normal mammograms and 13 in whom breast cancer was detected for the first time. All diagnoses of breast cancer were subsequently confirmed by tissue biopsy.

Results: The mean BMACs for the women with and without breast cancer are shown in FIG. 50. The mean BMAC was significantly depressed in the cancer group. Individual BMACs were analyzed by logistic regression to determine the probability of breast cancer based upon the breath test. FIG. 51 shows the scatter diagram of the probability of breast cancer as shown by the breath test in women with and without breast cancer.

Conclusions
1. The breath test identified all the women with breast cancer with no false positive or false negative results.
2. This finding is consistent with known pathophysiogical mechanisms i.e. increased ROS activity in the breast cancer resulted in increased production of alkanes which induced cytochrome p450 activity in breast and liver. As a result, there was increased clearance of alkanes and monomethylated alkanes in ambient room air, resulting in a depression of the BMAC.
3. The breath test appeared to provide a sensitive and specific screening test for breast cancer.

The BMAC appears to provide a new and highly sensitive marker of oxidative stress. As such, it may have a role in a number of diseases for primary screening, as well as to monitor the efficacy of treatment.

Tables Related to BMAC's

Table 6: Alkanes and methylalkanes significantly increased in older normals: 2-tailed t-tests comparing the compounds shown in FIGS. 3 and 4, demonstrating the statistical significance of the differences between younger and older normal humans.

Table 7: Characteristics of subject population. A number of the heart transplant recipients were studied more than once, on different occasions at least one month apart. There was no significant difference between the ages of the heart transplant recipients and the normal controls.

Table 8 Alkanes and methylalkanes in heart transplant recipients: Grade 0 rejection versus age-matched normal controls. 2-tailed t-tests were employed to compare the compounds shown in FIG. 36 demonstrating the statistical significance of the differences between heart transplant recipients with Grade 0 rejection and age-matched normal controls.

Table 9: Alkanes and methylalkanes in heart transplant recipients: Grade IIIa rejection versus Grade 0 rejection. 2-tailed t-tests were employed to compare the compounds shown in FIG. 37 demonstrating the statistical significance of the differences between heart transplant recipients with Grade IIIa rejection compared to those with Grade 0 rejection.

Table 10: Significant changes in components of the BMAC with age: The mean BMACs shown in FIG. 41 were compared with one-way ANOVA and a Neuman-Keuls post hoc test, and significant differences between quartiles are shown.

Table 11: Significantly different VOCS in patients with unstable angina and in age-matched normal controls. VOCs are ranked by significance of 2-tailed t-test.

Table 12: Causes of ESRD in patients studied

Table 13: VOCs other than BMAC that were significantly different in ESRD (pre-hemodialysis) compared to age-matched normals.

Table 14: Patient and tumor characteristics.

TABLE 1

BREATH VOCs RANKED BY FREQUENCY OF OCCURRENCE

| VOC | Mean alveolar gradient | % subjects |
|---|---|---|
| 50 most frequently occurring VOCs with positive alveolar gradients | | |
| isoprene | 60.34 | 100 |
| Benzene, (1-methylethenyl)- | 4.77 | 100 |
| Naphthalene | 4.07 | 100 |
| 2,5-Cyclohexadiene-1,4-dione, 2,6-bis(1,1-dimethylethyl)- | 0.61 | 100 |
| Naphthalene, 1-methyl- | 0.54 | 100 |
| Butane, 2-methyl- | 0.33 | 100 |
| Tetradecane | 0.23 | 100 |
| Pentadecane | 0.13 | 100 |
| Dodecane | 0.02 | 100 |
| Benzothiazole | 0.93 | 98 |
| 1,1'-Biphenyl, 2,2'-diethyl- | 0.69 | 98 |
| Ethane, 1,1,1-trichloro- | 0.12 | 98 |
| Tridecane | 0.10 | 98 |
| Styrene | 1.00 | 96 |
| Benzene, 1-methyl-4-(1-methylethyl)- | 0.01 | 96 |
| Ethanone, 1 phenyl- | 1.49 | 94 |
| Acetone | 27.91 | 92 |
| Benzenemethanol, .alpha.,.alpha.-dimethyl- | 20.39 | 92 |
| beta-Myrcene | 0.05 | 92 |
| Phenol, 2,6-bis(1,1-dimethylethyl)-4-methyl- | 0.34 | 90 |
| 1H-Indene, 2,3-dihydro-1,6-dimethyl- | 0.01 | 84 |
| 1,1'-Biphenyl | 0.06 | 78 |

TABLE 1-continued

BREATH VOCs RANKED BY FREQUENCY OF OCCURRENCE

| VOC | Mean alveolar gradient | % subjects |
|---|---|---|
| Ethene, tetrachloro- | 7.70 | 76 |
| 2,5 Cyclohexadiene-1,4-dione, 2,5 bis(1,1-dimethylpropyl)- | 0.24 | 74 |
| Octane, 2.0 dimethyl- | 0.02 | 74 |
| Benzoic acid, 4-ethoxy-, ethyl ester | 0.30 | 70 |
| Pentane, 3 methylene- | 0.28 | 70 |
| (1,1 (licyclopentyl)-2-one | 2.63 | 68 |
| (llmonene | 1.79 | 68 |
| Hexane, 2,2,5 trimethyl- | 0.36 | 66 |
| (1H Indene, 2,3-dihydro-4,6-dimethyl- | 0.15 | 64 |
| 2 Butene, 2,3 dimethyl- | 0.25 | 64 |
| Benzene, 1 bromo-3-fluoro- | 0.12 | 64 |
| Naphthalene, 2,7-dimethyl- | 0.09 | 64 |
| Naphthalene, 2 methyl- | 0.32 | 64 |
| Hexadecane, 2,6,10,14-tetramethyl- | 0.16 | 62 |
| 2 beta Pinene | 0.58 | 60 |
| Acetic acid | 2.63 | 60 |
| Propanoic acid, 2 methyl-, 1-(1,1-dimethylethyl)-2-methyl-1,3-propanediyl ester | 0.21 | 60 |
| 1,2 Benzenedicarboxylic acid, diethyl ester | 0.06 | 58 |
| Endobornylacetate | 0.42 | 58 |
| Benzene, (3 methyl-2 butenyl)- | 0.13 | 56 |
| Naphthalene, 1 ethyl- | 0.05 | 56 |
| Naphthalene, 2 ethyl- | 0.00 | 56 |
| Benzene, 1 ethyl 4-(1-methylethyl)- | 0.02 | 54 |
| Benzene, butyl- | 0.41 | 54 |
| Cyclohexene | 0.05 | 54 |
| Naphthalene, 1,6 dimethyl- | 0.11 | 54 |
| Honanal | 0.32 | 54 |
| 2 Propenoic acid, 2 methyl-, 1,2-ethanediylbis(oxy-2,1-ethanediyl) ester | 12.47 | 52 |
| Octadecane | 0.27 | 52 |
| Octane, 2,5 dimethyl- | 0.10 | 52 |
| 50 most frequently occurring VOCs with negative alveolar gradients | | |
| Benzene | −0.48 | 100 |
| Benzene, 1-ethyl-2-methyl- | −10.09 | 100 |
| Benzene, ethyl- | −1.73 | 100 |
| Benzene, methyl- | −7.27 | 100 |
| Benzene, propyl- | −1.72 | 100 |
| Cyclohexane, methyl- | −0.75 | 100 |
| Decane | −0.28 | 100 |
| Heptane | −1.25 | 100 |
| Heptane, 2-methyl- | −0.89 | 100 |
| Heptane, 3-methyl- | −0.83 | 100 |
| Hexane | −0.79 | 100 |
| Hexane, 3 methyl- | −1.02 | 100 |
| Nonane | −0.44 | 100 |
| Pentane, 2,3,4-trimethyl- | −0.26 | 100 |
| Pentane, 2-methyl- | −0.43 | 100 |
| Pentane, 3-methyl- | −0.59 | 100 |
| Propane, 2-methoxy-2-methyl | −9.44 | 100 |
| Undecane | −0.52 | 100 |
| alpha-Pinene, (-)- | −0.06 | 98 |
| Cyclohexane, ethyl- | −0.33 | 98 |
| Cyclopentane, methyl- | −1.25 | 98 |
| Decanal | 0.00 | 98 |
| 1-Pentene, 2-methyl- | −0.21 | 96 |
| Benzene, 1,2,3,5-tetramethyl- | −0.51 | 96 |
| Pentane, 2,3,3-trimethyl- | −0.10 | 96 |
| 1H-Indene, 2,3-dihydro-4,7-dimethyl- | −0.29 | 94 |
| Benzaldehyde | −0.31 | 94 |
| Camphene | −0.20 | 94 |
| Cyclopentane, 1,3-dimethyl-, cis- | −0.31 | 94 |
| Cyclopentane, ethyl- | −0.29 | 94 |
| Cyclopentene | −0.13 | 94 |
| 1H-Indene, 2,3-dihydro-5-methyl- | −0.30 | 92 |
| Benzene, 1,2,4-trimethyl- | −6.89 | 92 |
| Benzene, 1,3-dimethyl- | −5.38 | 92 |
| Benzene, 1-methyl-3-propyl- | −0.21 | 92 |
| Butane | −0.52 | 92 |
| Octane, 3 methyl- | −0.26 | 92 |
| Benzene, 1,2,3,4-tetramethyl- | −0.22 | 90 |

TABLE 1-continued

BREATH VOCs RANKED BY FREQUENCY OF OCCURRENCE

| VOC | Mean alveolar gradient | % subjects |
|---|---|---|
| Cyclohexane, 1,3-dimethyl, cis- | −0.31 | 90 |
| Hexane, 2-methyl- | −1.48 | 90 |
| 2-Hexene, (E)- | −0.27 | 88 |
| Benzene, (1-methylethyl)- | −0.76 | 88 |
| Benzene, 1,4-dimethyl- | −4.95 | 88 |
| Benzene, 1-ethyl-2,3-dimethyl- | −0.53 | 88 |
| Butane, 2,3-dimethyl- | −0.10 | 88 |
| Benzene, 1,3,5-trimethyl- | −2.44 | 86 |
| Benzene, 4-ethyl-1,2-dimethyl- | −0.71 | 86 |
| Heptane, 2,4-dimethyl- | −0.05 | 86 |
| Heptane, 2,5-dimethyl- | −0.20 | 84 |
| Hexane, 2,4-dimethyl- | −0.99 | 82 |

TABLE 2

BREATH VOCs RANKED BY ABUNDANCE

| VOC | Mean alveolar gradient | % subjects |
|---|---|---|
| *50 VOCs with highest mean positive alveolar gradients* | | |
| 4,5-Dimorpholino-2-methoxy-6-phenylpyrimidine | 655.61 | 4 |
| (-1,4 D2)-15,16-Dimethoxyethythrinan-7,8-dion-enol | 162.20 | 2 |
| Cyclohexanol, 5-methyl-2-(1-methylethyl)- | 75.83 | 4 |
| Isoprene | 60.34 | 100 |
| Methanol | 28.90 | 2 |
| Acetone | 27.91 | 92 |
| Benzenemethanol, .alpha.,.alpha.-dimethyl- | 20.39 | 92 |
| 1 Menthalone | 13.64 | 20 |
| licosane, 9-octyl- | 12.60 | 2 |
| 2H-1,4 Benzodiazepin-2-one, 7-chloro-1,3-dihydro-5-phenyl-1-(trimethylsilyl)- | 12.49 | 16 |
| 2 Propenoic acid, 2-methyl-, 1,2-ethanediylbis(oxy-2,1-ethanediyl) ester | 12.47 | 52 |
| Menthol | 7.82 | 2 |
| Ethene, tetrachloro- | 7.70 | 76 |
| (1)-Menthylacetate | 6.92 | 2 |
| 1,8 Cineole | 6.39 | 14 |
| Oxetane, 2 ethyl-3-methyl- | 5.02 | 6 |
| Benzene, (1-methylethenyl)- | 4.77 | 100 |
| Pyrazine, 2 ethyl-3-methyl- | 4.11 | 2 |
| Naphthalene | 4.07 | 100 |
| 111 1,2,4-Triazol-3 amine | 3.79 | 18 |
| Propanoic acid, 2-methyl-, 3-hydroxy-2,4,4-trimethylpentyl ester | 3.72 | 2 |
| Cyclopropane, (1-methylethyl)- | 3.59 | 2 |
| Methane, trichlorofluoro- | 3.45 | 40 |
| 2 Methyl 5 propylpyrazine | 3.18 | 2 |
| Benzene, (2-methl-1-methylenepropyl)- | 3.11 | 4 |
| Cyclopentanone | 3.07 | 34 |
| Cyclohexane, methoxy- | 2.81 | 4 |
| *50 VOCs with the highest mean negative alveolar gradients* | | |
| (1,1'-Bicyclopentyl)-2-one | 2.63 | 68 |
| Acetic acid | 2.63 | 60 |
| Butanoic acid, butyl ester | 2.44 | 2 |
| 2 Propeneoic acid, 2-metyl-, 1,2-ethanediyl ester | 2.39 | 48 |
| Acetic acid, (bis[trimethylsilyl]oxy(phosphinyl)-, trimethylsilyl ester | 2.28 | 40 |
| Ilnourea | 2.16 | 4 |
| Cyclopentane, (1 methylethyl)- | 2.15 | 2 |
| 1,3,7-Octatriene, 3,7-dimethyl- | 2.13 | 2 |
| 2 (1-Methylpropyl)pyrazine | 2.09 | 2 |
| Hexadecanoic acid, 1-methylethyl ester | 2.08 | 4 |
| Inalool | 2.06 | 12 |
| 1 uran, 2 butyltetrahyudro- | 1.95 | 6 |
| Cyclohexanol, 2-amino-, cis- | 1.93 | 6 |
| 1,3 Propanediol, 2-methyl-2-propyl- | 1.91 | 36 |

TABLE 2-continued

BREATH VOCs RANKED BY ABUNDANCE

| VOC | Mean alveolar gradient | % subjects |
|---|---|---|
| 1,E-1 1,2-13-Hexadecatriene | 1.85 | 2 |
| 9 Homonoradamant-9-ene | 1.85 | 2 |
| Peroxydihydrocostunolide | 1.83 | 4 |
| Heneicosane | 1.80 | 8 |
| di limonene | 1.79 | 68 |
| Pyrazine, 2,3 dimethyl- | 1.77 | 2 |
| 1 Propene, 1-(methylthiol-, (E)- | 1.75 | 18 |
| 1 Propanol, 2,2-dimethyl- | 1.73 | 2 |
| Biscyclo(4 1 0)heptane, 3,7,7-trimethyl- | 1.71 | 2 |
| 2 Propanol | −61.41 | 28 |
| 1-Propene | −27.15 | 2 |
| Benzene, 1-ethyl-2-methyl- | −10.09 | 100 |
| Propane, 2-methoxy-2-methyl- | −9.44 | 100 |
| Oxtane, 3,4-dimethyl- | −8.91 | 2 |
| Benzene, methyl- | −7.27 | 100 |
| Cyclohexene, 1-methyl-4-(1-methylethenyl)-, (R)- | −7.17 | 58 |
| Benzene, 1,2,4-trimethyl- | −6.89 | 92 |
| 4-Penten-2-ol | −6.42 | 2 |
| Benzene, 1,3-dimethyl- | −5.38 | 92 |
| 3-Butenoic acid | −5.34 | 2 |
| Benzene, 1,4-dimethyl- | −4.95 | 88 |
| 2-Chloro-4-(4-methoxyphenyl)-6-(4-nitrophenyl) pyrimidine | −4.30 | 18 |
| Pentane | −3.95 | 44 |
| Cyclohexanol, 5-methyl-2-(1-methylethyl)-, (1.alpha.,2.beta.,5.alpha.)-(.+−.)- | −3.30 | 2 |
| Hexanol-4-D2 | −2.85 | 4 |
| 1 Butene, 2-methyl- | −2.72 | 78 |
| Octane, trimethyl- | −2.68 | 2 |
| Benzene, 1,3,5-trimethyl- | −2.44 | 86 |
| Ethanone, 1-(3-ethylcyclobutyl)- | −2.31 | 2 |
| Pyrrolidine | −2.24 | 6 |
| Xylene | −2.14 | 32 |
| Octane | −2.02 | 74 |
| 1,4-Dihydropyran | −1.82 | 2 |
| Undecane, 3,5-dimethyl- | −1.75 | 6 |
| Benzene, 1-methyl-2-propyl- | −1.75 | 76 |
| alpha-Ylangene | −1.73 | 2 |
| Benzene, ethyl- | −1.73 | 100 |
| Benzene, propyl- | −1.72 | 100 |
| Methane, dichloro- | −1.71 | 10 |
| 1-Butene, 2,3-dimethyl- | −1.69 | 48 |
| 1,2-Pentadiene | −1.65 | 2 |
| Benzene, 1-methyl-4-propyl- | −1.60 | 10 |
| Phosphonic acid, diphenyl ester | −1.60 | 2 |
| Heptadecane, 9-octyl- | −1.58 | 4 |
| 1 Octadecene | −1.54 | 4 |
| Bicyclol3.2.1loci-ene, 3-methyl-4-methylene- | −1.51 | 2 |
| Pentane, 2,2,3,4-tetramethyl- | −1.51 | 26 |
| 4-Heptanone, 3-methyl- | −1.48 | 4 |
| Hexane, 2-methyl- | −1.48 | 90 |
| 3 Iodo-thiophene-2-caboxamide | −1.47 | 2 |
| IR Methyl-2T-phenylcyclopropane | −1.41 | 6 |
| Benzene, 1,2,3-trimethyl- | −1.39 | 56 |
| Palmitic acid, 2-(trimethylsiloxy)ethyl ester | −1.34 | 2 |
| beta-Ocimene-x | −1.32 | 8 |
| 4-Hydroxy-2-isopropyl-4,7-dimethyl-1(4H)-naphthalenone | −1.31 | 2 |
| 7 Azabicyclo[4 1 0]heptane, 3-methyl- | −1.31 | 2 |
| 4,7 Diphenyl-6-hydroxymethyl-1,2,5-oxadiazolo(3,4-c)pyridine | −1.27 | 2 |
| Benzene, 2-ethyl-1,3-dimethyl- | −1.26 | 54 |
| 2 Butanol, 3-methyl- | −1.26 | 2 |

APPENDIX 1

Kinetic Analysis of Determinants of the Alveolar Gradient

Let $R$ = rate of movement of VOC (mol/min)

$C$ = concentration of VOC (mol/min)

RMV = respiratory minute volume (l/min)

At equilibrium $R_{\text{into body}} = R_{\text{out of body}}$ $R_{\text{pulmonary input}} - R_{\text{extra pulmonary input}} = R_{\text{pulmonary output}} + R_{\text{clearance}}$ $R_{\text{extra pulmonary input}} - R_{\text{clearance}} = R_{\text{pulmonary output}} - R_{\text{pulmonary input}}$ $= (C_{\text{alveolar breath}} - C_{\text{room in}}) \times \text{RMV}$ i.e. alveolar gradient $= C_{\text{alveolar breath}} - C_{\text{room in}}$ $= \dfrac{(R_{\text{extra pulmonary input}} - R_{\text{clearance}})}{\text{RMV}}$ For a VOC synthesized in body and not ingested from extra pulmonary sources $R_{\text{extra - pulmonary input}} = R_{\text{synthesis}}$ Hence alveolar gradient $= \dfrac{(R_{\text{synthesis}} - R_{\text{clearance}})}{\text{RMV}}$

TABLE 3

| Cause of ESRD | no. patients |
|---|---|
| diabetes | 14 |
| hypertension | 5 |
| glomerular disease | 2 |
| nephrotic syndrome | 2 |
| chronic interstitial nephritis | 1 |
| nephritis | 1 |
| lithium toxicity | 1 |
| ruptured abdominal aorta aneurysm | 1 |
| myeloma | 1 |
| amyloidosis | 1 |
| benign prostatic hypertrophy | 1 |
| bilateral renal artery stenosis | 1 |
| nephrosclerosis | 1 |
| polycystic kidney disease | 1 |
| unknown | 7 |
| Total | 40 |

TABLE 4

VOCs INCREASED IN ESRD PATIENTS

| | mean AG normal | mean AG pre-dialysis | p 2-sided | no patients | mean AG post-dialysis | p 2-sided |
|---|---|---|---|---|---|---|
| Benzene, propyl- | −1.719 | −0.042 | <0.0001 | 40 | 0.033 | NS |
| Heptane, 3-methyl- | −0.826 | −0.053 | <0.0001 | 39 | −0.017 | NS |
| Benzene, 1-ethyl-2-methyl- | −10.093 | −0.351 | <0.0001 | 40 | 0.316 | NS |
| Benzene, methyl- | −7.266 | 0.300 | <0.0001 | 40 | 0.654 | NS |
| Heptane, 2-methyl- | −0.894 | −0.055 | <0.0001 | 39 | 0.090 | NS |
| Benzene, (1-methylethyl)- | −0.570 | −0.051 | <0.0001 | 36 | −0.098 | NS |
| Benzene, ethyl- | −1.727 | 0.027 | <0.0001 | 40 | 0.112 | NS |
| Cyclohexane, ethyl- | −0.328 | −0.033 | <0.0001 | 40 | 0.054 | NS |
| Hexane, 2,4-dimethyl- | −0.810 | 0.036 | <0.0001 | 23 | −0.046 | NS |
| Hexane, 3-methyl- | −1.025 | 0.047 | <0.0001 | 40 | 0.087 | NS |
| Heptane | −1.246 | 0.027 | <0.0001 | 40 | 0.247 | NS |
| Cyclopentane, ethyl- | −0.269 | −0.023 | <0.0001 | 39 | 0.023 | NS |
| Propane, 2-methoxy-2-methyl- | −9.438 | 3.369 | <0.0001 | 39 | 0.554 | NS |
| Cyclopentene | −0.123 | 0.060 | <0.001 | 30 | 0.043 | NS |
| Hexane, 2-methyl- | −1.332 | 0.059 | <0.001 | 30 | 0.129 | NS |
| Benzene, 1,2,4-trimethyl- | −6.336 | −0.257 | <0.001 | 40 | −0.024 | NS |
| Cyclopentane, methyl- | −1.221 | 0.007 | <0.01 | 40 | 0.084 | NS |
| Benzene, 1,4-dimethyl- | −4.360 | 0.088 | <0.01 | 32 | −0.142 | NS |
| Benzene, 1-ethyl-2,3-dimethyl- | −0.466 | 0.130 | <0.01 | 30 | −0.273 | NS |
| Cyclohexane, 1,3-dimethyl-, cis- | −0.279 | −0.050 | <0.01 | 37 | −0.092 | NS |
| Benzene, 1-ethyl-2,4-dimethyl- | −0.707 | 0.140 | <0.01 | 24 | 0.001 | NS |
| Benzene, 1,2,3,5-tetramethyl- | −0.486 | 0.085 | <0.01 | 32 | 0.228 | NS |
| Benzene, 1,3-dimethyl- | −4.951 | −0.765 | <0.01 | 29 | −0.214 | NS |
| Nonane | −0.439 | −0.052 | <0.05 | 40 | 0.055 | NS |
| Cyclohexene, 1-methyl-4-(1-methylethenyl)-, (R)- | −4.159 | 0.736 | <0.05 | 28 | −0.046 | NS |
| Cyclopentane, 1,3-dimethyl-, cis- | −0.289 | 0.053 | <0.05 | 33 | −0.014 | NS |
| Cyclohexane, 1,3-dimethyl-, trans- | −0.144 | 0.049 | <0.05 | 25 | 0.019 | NS |
| 2-Heptanone | −0.105 | −0.019 | <0.05 | 29 | −0.053 | NS |
| Benzene, 4-ethyl-1,2-dimethyl- | −0.610 | 0.001 | <0.05 | 31 | 0.039 | NS |
| Pentane, 2,4-dimethyl- | −0.138 | 0.077 | <0.05 | 24 | 0.040 | NS |
| 1H-indene, 2,3-dihydro-1-methyl- | −0.314 | 0.054 | <0.05 | 23 | 0.099 | NS |
| 1H-indene, 2,3-dihydro-5-methyl- | −0.276 | 0.167 | <0.05 | 32 | 0.032 | NS |
| Cyclohexane, 1,2-dimethyl-, trans- | −0.092 | −0.009 | <0.05 | 21 | −0.010 | NS |
| 1-Pentene, 2-methyl- | −0.204 | 0.064 | <0.05 | 25 | 0.108 | NS |
| 1H-indene, 2,3-dihydro-4,7-dimethyl- | −0.269 | 0.001 | <0.05 | 24 | 0.076 | NS |

TABLE 4-continued

VOCs INCREASED IN ESRD PATIENTS

|  | mean AG normal | mean AG pre-dialysis | p 2-sided | no patients | mean AG post-dialysis | p 2-sided |
|---|---|---|---|---|---|---|
| Benzaldehyde | −0.295 | −0.065 | <0.05 | 26 | −0.015 | NS |
| Cyclohexane, propyl- | −0.143 | 0.017 | <0.05 | 22 | −0.020 | NS |
| Octane, 3-methyl- | −0.241 | −0.089 | <0.05 | 31 | −0.064 | NS |

TABLE 5

VOCs DECREASED IN ESRD PATIENTS

|  | mean AG normal | mean AG pre-dialysis | p 2-sided | no patients | mean AG post-dialysis | p 2-sided |
|---|---|---|---|---|---|---|
| Ethanone, 1-phenyl- | 1.404 | −0.006 | <0.0001 | 26 | 0.166 | NS |
| Benzenemethanol, .alpha., .alpha.-dimethyl- | 18.760 | 0.817 | <0.0001 | 24 | 2.276 | NS |
| Naphthalene | 4.073 | 0.335 | <0.001 | 39 | 0.473 | NS |
| 1,1'-Biphenyl, 2,2'-diethyl- | 0.678 | −0.003 | <0.001 | 40 | 0.516 | <0.05 |
| Cyclohexanone | 0.089 | −2.000 | <0.001 | 33 | −1.054 | NS |
| Benzothiazole | 0.910 | 0.219 | <0.001 | 40 | 0.193 | NS |
| 2-Butanone | 0.009 | −0.139 | <0.01 | 27 | −0.022 | NS |
| 2,5-Cyclohexadiene-1,4-dione, 2,6-bis(1,1-dimethylethyl)- | 0.606 | 0.109 | <0.01 | 39 | 0.192 | NS |
| Benzoic acid, 4-ethoxy-, ethyl ester | 0.213 | 0.055 | <0.01 | 22 | 0.161 | NS |
| 2-Cyclohexen-1-one | 0.024 | −0.091 | <0.01 | 25 | −0.120 | NS |
| Acetone | 25.677 | 8.828 | <0.01 | 40 | 11.907 | NS |
| Benzene, (1-methylethenyl)- | 4.775 | 1.272 | <0.01 | 33 | 1.179 | NS |
| 1,1'-Biphenyl | 0.047 | 0.004 | <0.05 | 25 | 0.014 | NS |
| Acetic acid, [bis[(trimethylsilyl)oxy]phosphinyl]-, trimethylsilyl ester | 0.913 | 0.123 | <0.05 | 24 | −0.042 | NS |
| (1,1'-Biscyclopentyl)-2-one | 1.791 | −0.147 | <0.05 | 25 | −0.177 | NS |
| 2-Cyclohexen-1-one, 2-methyl-5-(1-methylethenyl)- | 0.078 | −0.060 | <0.05 | 22 | 0.042 | NS |
| Ethanol, 2-butoxy- | 0.006 | −3.847 | <0.05 | 21 | −2.412 | NS |
| Hexadecane, 2,6,10,14-tetramethyl- | 0.099 | −0.005 | <0.05 | 24 | −0.048 | NS |
| Heptane, 2,2,4,6,6-pentamethyl- | 0.101 | −0.196 | <0.05 | 32 | 0.008 | NS |

TABLE 6

Alkanes and methylalkanes significantly increased in older normals p < 0.00001 decane, 3-methyl
heptane, 3-methyl p < 0.0001 dodecane, 6-methyl
heptane
octane
heptane, 2-methyl
octane, 3-methyl
hexane, 3-methyl
hexane, 2-methyl p < 0.001 decane, 2-methyl
nonane, 2-methyl
hexane
decane, 5-methyl p < 0.01 nonane
tetradecane, 5-methyl
undecane, 5-methyl
undecane
tridecane, 3-methyl p < 0.05 octane, 4-methyl
heptadecane
pentane, 2-methyl
decane
octane, 2-methyl
butane, 2-methyl
dodecane

TABLE 7

Characteristics of subjects

|  | Normal controls | Heart transplant recipients |
|---|---|---|
| Total no. | 20 | 126 |
| no. breath samples | 20 | 210 |
| no. endomyocardial biopsies - |  | 210 |
| Mean age (SD) |  |  |
| Males | 50.6 (9.9) | 52.3 (12.0) |
| Females | 50.4 (12.3) | 54.9 (9.33) |
| Sex (m/f) | 12/8 | 107/19 |

TABLE 8

Alkanes and methylalkanes significantly increased in heart transplant recipients VOCs are ranked in decreasing order of statistical significance
(p < 0.05 for all, on 2-tailed t-test)

decane, 5-methyl
eicosane, 3-methyl
heptane, 2-methyl
heptane, 3-methyl
hexane, 2-methyl
nonadecane, 3-methyl
nonane, 5-methyl
octane, 3-methyl
pentane, 3-methyl
tetradecane, 3-methyl
heptane
hexane
octane
tetradecane

TABLE 9

Alkanes and methylalkanes in heart transplant recipients:
Grade IIIa rejection versus Grade 0 rejection.

VOCs are ranked in decreasing order of statistical significance
(p < 0.05 for all, on 2-tailed t-test)

heptadecane, 3-methyl
heptadecane, 7-methyl
octadecane, 2-methyl
octadecane, 5-methyl
pentadecane, 5-methyl
tetradecane, 4-methyl
tridecane, 4-methyl

TABLE 11

Significantly different VOCS in patients with unstable
angina and in age-matched normal controls.

VOCs are ranked by significance of 2-tailed t-test.

Heptadecane
<0.01
Dodecane, 6-methyl
<0.01
Pentadecane, 6-methyl
<0.05
Tetradecane, 5-methyl
<0.05
Octane
<0.05
Undecane, 4-methyl
<0.05
Nonane, 2-methyl
<0.05
Decane, 3-methyl
<0.05
Nonane, 3-methyl
<0.05
Pentane, 3-methyl
<0.05

TABLE 12

Causes of ESRD in patients studied

| | |
|---|---|
| diabetes mellitus | 14 |
| hypertension | 5 |
| glomerular disease | 2 |
| nephrotic disease | 2 |
| nephrotic syndrome | 2 |
| chronic interstitial nephritis | 1 |
| nephritis | 1 |

TABLE 10

Alkanes and monomethylalkanes: significant differences between quartiles

| | quartile 1 vs quartile 2 | quartile 1 vs quartile 3 | quartile 1 vs quartile 4 | quartile 2 vs quartile 3 | quartile 2 vs quartile 4 | quartile 3 vs quartile 4 |
|---|---|---|---|---|---|---|
| pentane, 2-methyl | | | | | <0.05 | |
| hexane | | | <0.05 | | <0.01 | |
| hexane, 2-methyl | | | <0.05 | <0.05 | <0.01 | |
| hexane, 3-methyl | | | <0.05 | <0.05 | <0.001 | |
| heptane | | | <0.01 | <0.05 | <0.001 | |
| heptane, 2-methyl | | | <0.05 | <0.01 | <0.001 | |
| heptane, 3-methyl | | | <0.01 | <0.01 | <0.001 | |
| octane | | <0.05 | <0.01 | <0.01 | <0.001 | |
| octane, 3-methyl | | | <0.01 | <0.01 | <0.001 | <0.05 |
| octane, 4-methyl | <0.05 | <0.05 | <0.05 | | | |
| nonane | | | | <0.01 | <0.01 | |
| nonane, 2-methyl | | <0.05 | <0.01 | <0.05 | <0.05 | |
| decane, 2-methyl- | | | <0.001 | | <0.001 | <0.05 |
| decane, 3-methyl- | | <0.01 | | <0.001 | <0.001 | |
| decane, 5-methyl- | | <0.05 | <0.05 | <0.05 | <0.05 | |
| undecane | | | | <0.05 | <0.01 | |
| undecane, 5-methyl | | <0.05 | <0.05 | | | |
| dodecane, 5-methyl- | | <0.01 | <0.01 | <0.01 | <0.01 | |
| tridecane, 2-methyl | | | <0.05 | | <0.05 | <0.05 |
| tridecane, 3-methyl | | | | | | |
| tetradecane, 5-methyl | | <0.01 | <0.01 | | | |
| heptadecane | | <0.01 | | | | <0.05 |

TABLE 12-continued

Causes of ESRD in patients studied

| | |
|---|---|
| lithium toxicity | 1 |
| ruptured aortic aneurysm | 1 |
| myeloma | 1 |
| amyloidosis | 1 |
| benign prostatic hypertrophy | 1 |
| bilateral renal artery stenosis | 1 |
| nephrosclerosis | 1 |
| polycystic kidney disease | 1 |
| unknown | 1 |
| Total | 40 |

TABLE 13

VOCs other than BMAC that were significantly different in ESRD (pre-hemodialysis) compared to age-matched normals

VOCs increased in ESRD $p < 0.0001$ benzene, propyl
heptane, 3-methyl-
benzene, 1-ethyl-2-methyl-
benzene, methyl
heptane, 2-methyl-
benzene, (1-methylethyl)-
benzene, ethyl-
cyclohexane, ethyl-
hexane, 2,4-dimethyl-
hexane, 3-methyl-
heptane
cyclopentane, ethyl-
propane, 2-methoxy-2-methyl- $p < 0.001$ cyclopentene
hexane, 2-methyl-
benzene, 1,2,4-trimethyl $p < 0.01$ cyclopentane, methyl-
benzene, 1,4-dimethyl-
benzene, 1-ethyl-2,3-dimethyl-
cyclohexane, 1,3-dimethyl-, cis-
benzene, 1-ethyl-2,4-dimethyl-
benzene, 1,2,3,5-tetramethyl-
benzene, 1,3-diethyl- $p < 0.05$ nonane
cyclohexene, 1-methyl-4-(methylethenyl)-, (R)-
cyclopentane, 1,3-dimethyl-,cis-
cyclohexane, 1,3-dimethyl-,trans
2-heptanone
benzene, 4-ethyl-1,2-dimethyl-

TABLE 13-continued

VOCs other than BMAC that were significantly different in ESRD (pre-hemodialysis) compared to age-matched normals pentane, 2,4-dimethyl-
1H-indene,2,3-dihydro-1-methyl
1H-indene,2,3-dihydro-5-methyl
cyclohexane, 1,2-dimethyl-,trans
1-pentene, 2-methyl-
1H-indene,2,3-dihydro-4,7-dimethyl
benzaldehyde
cyclohexane, propyl-
octane, 3-methyl-

VOCs decreased in ESRD $p < 0.0001$ ethanone, 1-phenyl-
benzenemethanol, alpha, alpha-dimethyl- $p < 0.001$ naphthalene
1,1'-biphenyl, 2,2'-diethyl-
cyclohexanone
benzothiazole $p < 0.01$ 2-butanone
2,5-cyclohexadiene-1,4-dione, 2,6-bis(1,1-dimethylethyl)-
benzoic acid, 4-ethoxy-,ethyl ester
2-cyclohexen-1-one
acetone
benzene, (1-methylethenyl-)

$p < 0.05$ 1,1'-biphenyl
acetic acid (bis(trimethylsilyl)oxy)phosphinyl)-,trimethylsilyl ester
(1,1'-bicyclopentyl)-2-one
2-cyclohexen-1-one,2-methyl-5-(1-methylethyl)-
ethanol, 2-butoxy-
hexadecane, 2,6,10,14-tetramethyl
heptane, 2,2,4,6,6-pentamethyl-

TABLE 14

Patient and tumor characteristics

| | | |
|---|---|---|
| No. patients studied | | 169 |
| Biopsy findings: | cancer | 85 |
| | No cancer | 84 |

| | Tobacco smoking | | | | Age | Sex | |
|---|---|---|---|---|---|---|---|
| | Smokers | ex-smokers | non-smoker | unknown | range | F/M | Total |
| No cancer | 21 | 36 | 24 | 3 | 25–89 | 45/39 | 84 |
| Cancer: non small cell | 18 | 29 | 3 | 5 | 50–96 | 16/39 | 55 |
| small cell | 3 | 4 | 0 | 3 | 51–89 | 4/6 | 10 |
| metastatic | 4 | 7 | 3 | 1 | 48–82 | 11/4 | 15 |

TABLE 14-continued

Patient and tumor characteristics

| | | | | | | |
|---|---|---|---|---|---|---|
| No. patients studied | | | 169 | | | |
| Biopsy findings: | | cancer | 85 | | | |
| | | No cancer | 84 | | | |
| Tobacco smoking | | | | Age | Sex | |
| Smokers | ex-smokers | non-smoker | unknown | range | F/M | Total |
| Undetermined | 3 | 1 | 1 | 0 | 56–74 | 1/4 | 5 |
| Total | 49 | 77 | 31 | 12 | 25–96 | 77/92 | 169 |

I claim:

1. A process for determining the presence or absence of aging in a mammal which comprises:

collecting a representative sample of alveolar breath from the mammal;

collecting a representative sample of ambient air; analyzing the samples of breath and air to determine content of n-alkanes having 2 to 20 carbon atoms inclusive;

calculating the alveolar gradients of the n-alkanes having 2 to 20 carbon atoms, inclusive, in the breath sample in order to determine the alkane profile; and comparing the alkane profile to baseline alkane profiles calculated for mammals;

the finding of differences in the alkane profile from the baseline alkane profile being indicative of the presence of aging.

2. The process of claim 1 wherein the mammal is a human.

3. The process of claim 1 further comprising:

analyzing the samples of breath and air to determine the methylation site, if any of n-alkanes having 3 to 20 carbon atoms, inclusive;

wherein determining the alkane profile further comprises calculating the alveolar gradients of methylated alkanes having 3 to 20 carbon atoms, inclusive, in the breath sample in order to determine a second component in the alveolar profile; and comparing the alkane profile to baseline alkane profiles calculated for mammals;

the finding of differences in the alkane profile from the baseline alkane profile being indicative of the presence of aging.

4. The process of claim 3 wherein the mammal is human.

* * * * *